(12) United States Patent
Nantermet et al.

(10) Patent No.: US 7,678,783 B2
(45) Date of Patent: Mar. 16, 2010

(54) MACROCYCLIC TERTIARY AMINE BETA-SECRETASE INHIBITORS FOR THE TREATMENT OF ALZHEIMER'S DISEASE

(75) Inventors: Philippe G. Nantermet, Lansdale, PA (US); Hemaka A. Rajapakse, Wyncote, PA (US); Harold G. Selnick, Ambler, PA (US); Stacey Lindsley, Schwenksville, PA (US); Keith P. Moore, North Wales, PA (US); Shawn J. Stachel, Perkasie, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 71 days.

(21) Appl. No.: 11/667,913

(22) PCT Filed: Nov. 14, 2005

(86) PCT No.: PCT/US2005/040984

§ 371 (c)(1),
(2), (4) Date: May 16, 2007

(87) PCT Pub. No.: WO2006/055434

PCT Pub. Date: May 26, 2006

(65) Prior Publication Data

US 2008/0269302 A1    Oct. 30, 2008

Related U.S. Application Data

(60) Provisional application No. 60/628,830, filed on Nov. 17, 2004, provisional application No. 60/653,036, filed on Feb. 15, 2005.

(51) Int. Cl.
*A01N 43/00* (2006.01)
*A61K 31/33* (2006.01)
*C07D 513/00* (2006.01)

(52) U.S. Cl. ...................... 514/183; 540/455
(58) Field of Classification Search ............ None
See application file for complete search history.

(56) References Cited

U.S. PATENT DOCUMENTS 6,333,410 B1  12/2001  Chari et al.
6,525,074 B2   2/2003  deSolms et al.
7,109,217 B2   9/2006  Coburn et al.
2006/0058278 A1   3/2006  Coburn et al.
2006/0149092 A1   7/2006  Nantermet et al.
2006/0161020 A1   7/2006  Coburn et al.
2006/0293380 A1  12/2006  Nantermet et al.
2007/0037784 A1   2/2007  Coburn et al.

FOREIGN PATENT DOCUMENTS

WO    WO 03/106405       12/2003
WO    WO 2005/005374      1/2005
WO    WO 2005/051914      6/2005
WO    WO 2005/065195      7/2005
WO    WO 2005/103020     11/2005
WO    WO 2005/103043     11/2005
WO    WO 2006/015621      2/2006
WO    WO 2006/057983 A1   6/2006

OTHER PUBLICATIONS

De Stooper et al. Nature, 1999, 402, 471-472.*
Coburn,et al., J Med Chem, 2004, 47:6117-6119.
Stachel, et al., J Med Chem, 2004, 47: 6447-6450.
October 12, 2009 EPO Communication from counterpart European Appln. No. 05825640.5.

* cited by examiner

*Primary Examiner*—James O Wilson
*Assistant Examiner*—Noble Jarrell
(74) *Attorney, Agent, or Firm*—William Kronatin; John C. Todaro

(57) ABSTRACT

The present invention is directed to macrocyclic tertiary amine compounds represented by general formula (I)

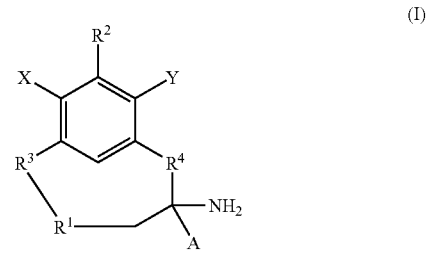

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

10 Claims, No Drawings

MACROCYCLIC TERTIARY AMINE BETA-SECRETASE INHIBITORS FOR THE TREATMENT OF ALZHEIMER'S DISEASE

CROSS REFERENCE TO RELATED APPLICATIONS

This application claims priority under 35 U.S.C. §119(e) of U.S. provisional application Ser. Nos. 60/628,830, filed Nov. 17, 2004 and U.S. provisional application Ser. No. 60/653,036, filed Feb. 15, 2005.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to the field of compounds which are inhibitors of the activity of the β-secretase enzyme, and to the use of the compounds for the treatment of diseases in which the β-secretase enzyme is involved, such as Alzheimer's disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and SAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most APP, is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to novel macrocyclic tertiary amine compounds represented by general formula (I)

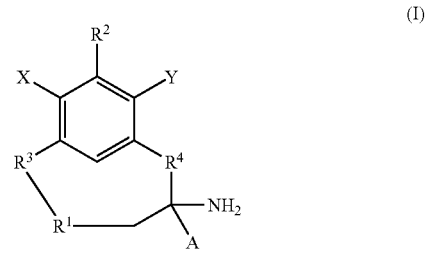

(I)

and pharmaceutically acceptable salts thereof, and individual enantiomers and diastereomers thereof, which are useful as inhibitors of the β-secretase enzyme.

The invention is also directed to pharmaceutical compositions which include an effective amount of a compound of formula (I), or pharmaceutically acceptable salts thereof, and individual enantiomers and diastereomers thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

The present invention is directed to compounds of formula (I):

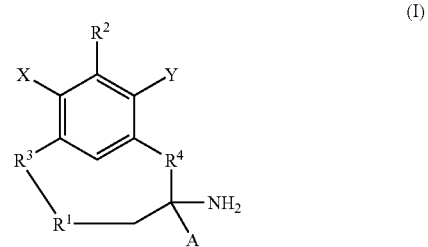

(I)

and pharmaceutically acceptable salts thereof, and individual enantiomers and diastereomers thereof, wherein:

X and Y are selected from the group consisting of
  (1) hydrogen,
  (2) —$C_{1-3}$ alkyl,
  (3) halogen, and
  (4) cyano;

A is selected from the group consisting of
  (1) hydrogen,
  (2) —$C_{1-10}$ alkyl,
  (3) —$C_{2-10}$ alkenyl, and
  (4) —$C_{2-10}$ alkynyl, wherein said alkyl, alkenyl or alkynyl is unsubstituted or substituted with one or more
(a) halo,
(b) —$C_{3-8}$ cycloalkyl,
(c) —OH,
(d) —CN,
(e) —O—$C_{1-10}$ alkyl,
(f) —$C_{6-10}$ aryl, or
(g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said aryl and heteroaryl groups are unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(vii) —$C_{2-10}$ alkynyl, or
(viii) —$C_{3-8}$ cycloalkyl;

$R^1$ is selected from the group consisting of
(1) —$C_{6-10}$ arylene, or
(2) heteroarylene selected from the group consisting of divalent pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said arylene or heteroarylene is unsubstituted or substituted with one or more
(a) halo,
(b) —$C_{1-10}$ alkyl,
(c) —$C_{2-10}$ alkenyl,
(d) —$C_{2-10}$ alkynyl,
(e) —OH,
(f) —CN,
(g) —O—$C_{1-10}$ alkyl, or
(h) —$C_{3-8}$ cycloalkyl;

$R^2$ is selected from the group consisting of:
(1) ($R^5$—$SO_2$)N($R^6$)—, wherein $R^5$ is
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
(g) —$NR^7R^8$,
wherein said alkyl, alkenyl, alkynyl, cycloalkyl, aryl and heteroaryl is unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(vii) —$C_{2-10}$ alkynyl,
(viii) —$C_{3-8}$ cycloalkyl,
(ix) —$C_{6-10}$ aryl, or
(x) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said aryl and heteroaryl is unsubstituted or substituted with one or more
(A) halo,
(B) —OH,
(C) —CN,
(D) —O—$C_{1-10}$ alkyl,
(E) —$C_{3-8}$ cycloalkyl,
(F) —$C_{1-10}$ alkyl,
(G) —$C_{2-10}$ alkenyl, or
(H) —$C_{2-10}$ alkynyl;

$R^6$ is selected from the group consisting of
(a) hydrogen,
(b) —$C_{1-10}$ alkyl,
(c) —$C_{2-10}$ alkenyl,
(d) —$C_{2-10}$ alkynyl,
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said alkyl, alkenyl, alkynyl, aryl or heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{6-10}$ aryl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;
wherein said cycloalkyl, aryl or heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) —$C_{6-10}$ aryl,
or $R^5$ and $R^6$ may be linked to form a group —$CH_2(CH_2)_pCH_2$—;
(2) —$C_{6-10}$ aryl, wherein said aryl is unsubstituted or substituted with one or more
(i) halo,
(ii) —OH,
(iii) —CN,
(iv) —O—$C_{1-10}$ alkyl,
(v) —$C_{3-8}$ cycloalkyl, (vi) —$C_{1-10}$ alkyl,
(vi) —$C_{6-10}$ aryl, or (3) 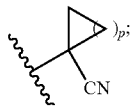

(4) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{1-10}$ alkyl,
(vii) —C(=O)—O—$C_{1-10}$ alkyl,
(viii) —C(=O)—OH, and
(ix) —C(=O)—$NR^cR^d$,
(x) —$NR^cR^d$, wherein $R^c$ and $R^d$ are selected from the group consisting of
(A) hydrogen, and
(B) —$C_{1-10}$ alkyl;
(5) hydrogen;
(6) —$CF_3$; and
(7) —O—$SO_2$—$R^9$;

$R^3$ is selected from the group consisting of (1) 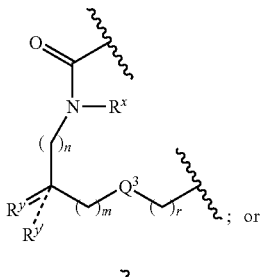; or (2) 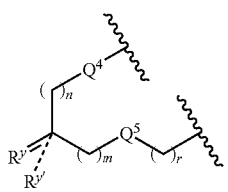

wherein $R^x$ is selected from the group consisting of
(a) hydrogen,
(b) —$C_{1-6}$ alkyl,
(c) —$C_{0-3}$ alkylene-$C_{3-8}$ cycloalkyl,
(d) —$C_{0-3}$ alkylene-$C_{6-10}$ aryl
and said Rx alkyl, alkylene, cycloalkyl and aryl groups are unsubstituted or substituted with one or more
(i) halo,
(ii) —$C_{1-10}$ alkyl,
(iii) —OH,
(iv) —CN, or
(v) —O—$C_{1-10}$ alkyl,
and if the dotted line leading to $R^y$ is absent, then $R^y$ is selected from the group consisting of
(a) hydrogen,
(b) —$C_{1-10}$ alkyl,
(c) —$C_{2-10}$ alkenyl,
(d) —$C_{2-10}$ alkynyl,
(e) —$C_{3-8}$ cycloalkyl,
(f) —$C_{0-6}$ alkylene-$C_{6-10}$ aryl, or
(g) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said $R^y$ alkyl, alkylene, alkenyl, alkynyl, cycloalkyl and heteroaryl groups are unsubstituted with one or more
(i) halo,
(ii) —$C_{1-10}$ alkyl,
(iii) —OH,
(iv) —CN, or
(v) —O—$C_{1-10}$ alkyl,
and $R^{y'}$ is selected from the group consisting of
(a) hydrogen, and
(b) —$CH_3$,
and if the dotted line leading to $R^y$ represents a bond, then $R^{y'}$ is absent and $R^y$ is selected from the group consisting of
(a) =CH—$C_{1-10}$ alkyl,
(b) =CH—$C_{0-6}$ alkylene-$C_{6-10}$ aryl, or
(c) =$CH_2$
wherein said alkyl, alkylene, cycloalkyl, aryl or heteroaryl $R^y$ groups are unsubstituted or substituted with one or more
(i) halo,
(ii) —$C_{1-10}$ alkyl,
(iii) —OH,
(iv) —CN, or
(v) —O—$C_{1-10}$ alkyl, or
(vi) —$C_{3-8}$ cycloalkyl;

$Q^3$, $Q^4$ and $Q^5$ are selected from the group consisting of
(a) —$CH_2$
(b) —O—, and
(c) —NH—;

$R^4$ is —$(CH_2)_n$-$Q^2$-$(CH_2)_m$, wherein $Q^2$ is selected from the group consisting of
(1) —O—,
(2) —NH—,
(3) —O—C(=O)—,
(4) —C(=O)—O—,
(5) —NHC(=O)—,
(6) —C(=O)—NH—,
(7) —CH=CH—,
(8) —C(=O)—,
(9) —$(CH_2)_q$—,

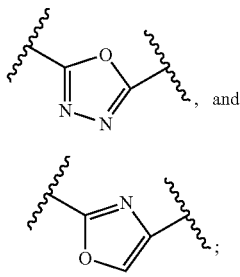

(10)

, and (11)

R⁷ and R⁸ are selected from the group consisting of
(1) —$C_{1-10}$ alkyl, and
(2) —$C_{0-3}$ alkyne-$C_{6-10}$ aryl,
wherein said alkyl, alkylene and aryl is unsubstituted or substituted with one or more
(a) halo,
(b) —$C_{1-10}$ alkyl,
(c) —OH,
(d) —CN,
(e) —O—$C_{1-10}$ alkyl, or
(f) —$C_{3-8}$ cycloalkyl;

R⁹ is selected from the group consisting of
(1) —$C_{1-10}$ alkyl, and
(2) —$C_{0-3}$ alkylene-$C_{6-10}$ aryl,
wherein said alkyl, alkylene and aryl is unsubstituted or substituted with one or more
(a) halo,
(b) —$C_{1-10}$ alkyl,
(c) —OH,
(d) —CN,
(e) —O—$C_{1-10}$ alkyl, or
(f) —$C_{3-8}$ cycloalkyl, or
R⁹ is NR⁷R⁸;

m is 0, 1 or 2;

n is 0, 1 or 2;

p is 1, 2, 3, 4 or 5;

q is 2, 3, 4 or 5; and r is 0, 1 or 2.

In a preferred embodiment of the compounds of formula (I), X and Y are both hydrogen.

In another preferred embodiment of the compounds of formula (I), R¹ is unsubstituted or substituted —$C_{6-10}$ arylene, preferably unsubstituted phenylene.

In another preferred embodiment of the compounds of formula (I), R⁴ is —$(CH_2)_n$-$Q^2$-$(CH_2)_m$, wherein $Q^2$ is selected from the group consisting of
(1) —O—,
(2) —O—C(═O)—,

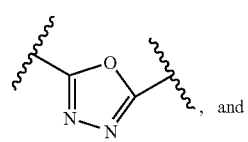

(3)

, and

-continued

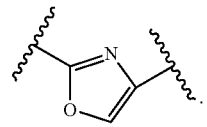

(4)

In this embodiment, n and m are preferably each 1.

In one embodiment of the compounds of formula (I), R³ is as depicted in paragraph (1) below:

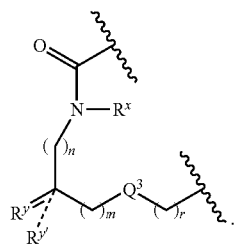

In this embodiment, $R^x$ is preferably hydrogen. In this embodiment, if the dotted line leading to $R^y$ is absent, $R^y$ is preferably selected from the group consisting of
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{0-6}$ alkylene-$C_{6-10}$ aryl, or
(f) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said alkyl, alkylene, alkenyl, alkynyl, cycloalkyl, aryl or heteroaryl are unsubstituted or substituted with one or more
(i) halo,
(ii) —$C_{1-10}$ alkyl,
(iii) —OH,
(iv) —CN,
(v) —O—$C_{1-10}$ alkyl, or
(vi) —$C_{3-8}$ cycloalkyl;
and $R^{y'}$ is preferably hydrogen.

In this embodiment, if the dotted line leading to $R^y$ represents a bond, then $R^y$ is preferably selected from the group consisting of
(a) ═CH—$C_{1-10}$ alkyl, or
(b) ═CH—$C_{0-6}$ alkylene-$C_{6-10}$ aryl,
wherein said alkyl, alkylene, aryl or heteroaryl groups are unsubstituted or substituted with one or more
(i) halo,
(ii) —$C_{1-10}$ alkyl,
(iii) —OH,
(iv) —CN, or
(v) —O—$C_{1-10}$ alkyl, or
(vi) —$C_{3-8}$ cycloalkyl.

In this embodiment, $Q^3$ is preferably —O— or —CH$_2$, m is preferably 1, and n and r are each preferably 0.

Preferably, $R^x$ and $R^y$ are not both hydrogen.

In another embodiment of the compounds of formula (I), $R^3$ is as depicted in paragraph (2) below:

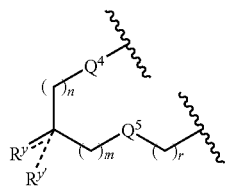

In this embodiment, if the dotted line leading to $R^y$ is absent, $R^y$ is preferably selected from the group consisting of
- (a) —C$_{1-10}$ alkyl,
- (b) —C$_{2-10}$ alkenyl,
- (c) —C$_{2-10}$ alkynyl,
- (d) —C$_{3-8}$ cycloalkyl,
- (e) —C$_{0-6}$ alkylene-C$_{6-10}$ aryl, or
- (f) —C$_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  - wherein said alkyl, alkenyl, alkynyl, cycloalkyl, aryl or heteroaryl are unsubstituted or substituted with one or more
    - (i) halo,
    - (ii) —C$_{1-10}$ alkyl,
    - (iii) —OH,
    - (iv) —CN, or
    - (v) —O—C$_{1-10}$ alkyl, or
    - (vi) —C$_{3-8}$ cycloalkyl,
  - and $R^{y'}$ is hydrogen.

In this embodiment, if the dotted line leading to $R^y$ represents a bond, then $R^y$ is preferably selected from the group consisting of
- (a) =CH—C$_{1-10}$ alkyl, or
- (b) =CH—C$_{0-6}$ alkylene-C$_{6-10}$ aryl,
  - wherein said alkyl, alkylene, aryl or heteroaryl groups are unsubstituted or substituted with one or more
    - (i) halo,
    - (ii) —C$_{1-10}$ alkyl,
    - (iii) —OH,
    - (iv) —CN,
    - (v) —O—C$_{1-10}$ alkyl, or
    - (vi) —C$_{3-8}$ cycloalkyl.

In this embodiment, preferably $Q^4$ is —O— or —CH$_2$— and $Q^5$ is —O— or —CH$_2$—. Preferably, n and m are each 1, and r is preferably 0.

In preferred embodiments of the compounds of formula (I), A is selected from the group consisting of
- (1) hydrogen, and
- (2) —C$_{1-10}$ alkyl,
  - wherein said alkyl is unsubstituted or substituted with one or more
    - (a) halo,
    - (b) —C$_{3-8}$ cycloalkyl,
    - (c) —CN
    - (d) —O—C$_{1-10}$ alkyl,
    - (e) phenyl, or
    - (f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl.

In a more preferred embodiment of the compounds of the formula (I), A is —C$_{1-10}$ alkyl (preferably methyl), wherein said alkyl is unsubstituted or substituted with one or more halo (preferably fluoro).

In a preferred embodiment of the compounds of formula (I), $R^2$ is selected from the group consisting of $(R^5$—SO$_2)$N$(R^6)$—, wherein $R^5$ is —C$_{1-6}$ alkyl, wherein said alkyl is unsubstituted or substituted with one or more
- (i) halo,
- (ii) —OH,
- (iii) —CN,
- (iv) —O—C$_{1-6}$ alkyl, or
- (v) —C$_{1-6}$ alkyl, $R^6$ is selected from the group consisting of
- (a) hydrogen,
- (b) —C$_{1-6}$ alkyl, or
- (c) —C$_{6-10}$ aryl,
  - wherein said alkyl and aryl is unsubstituted or substituted with one or more
    - (i) halo,
    - (ii) —OH,
    - (iii) —CN,
    - (iv) —O—C$_{1-6}$ alkyl,
    - (v) —C$_{1-6}$ alkyl, or $R^5$ and $R^6$ are linked to form a group —CH$_2$(CH$_2$)$_p$CH$_2$—.

Another preferred $R^2$ group is —C$_{6-10}$ aryl, unsubstituted or substituted as described above. Preferred aryl groups are phenyl groups, unsubstituted or substituted with cyano. A preferred $R^2$ substituent is shown below:

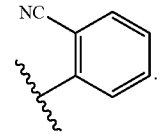

Another preferred $R^2$ substituent is

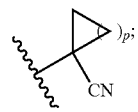

wherein p is 1, 2 or 3.

Another preferred $R^2$ substituent is heteroaryl, either unsubstituted or substituted as described above. A preferred heteroaryl group is furanyl or oxazolyl, either unsubstituted or substituted as described above. A preferred furanyl or oxazolyl substituent is depicted below:

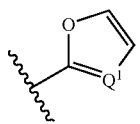

wherein $Q^1$ is selected from the group consisting of
(a) N, and
(b) C—$R^b$, wherein $R^b$ is selected from the group consisting of
  (i) —CN, and
  (ii) —C(=O)—O—$C_{1-10}$ alkyl,
  (iii) —C(=O)—OH, and
  (iv) —C(=O)—$NR^cR^d$,
  (v) —$NR^cR^d$, wherein $R^c$ and $R^d$ are selected from the group consisting of
    (A) hydrogen, and
    (B) —$C_{1-10}$ alkyl.

Another embodiment of the present invention is directed to compounds of formula (II):

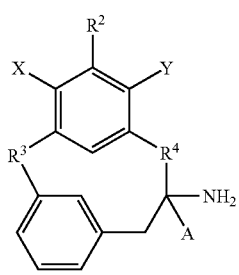

(II)

wherein A, X, Y, $R^2$, $R^3$ and $R^4$ are as defined above, and pharmaceutically acceptable salts thereof, and individual enantiomers and diastereomers thereof.

In a preferred embodiment of the compounds of formula (II), X and Y are both hydrogen.

In another preferred embodiment of the compounds of formula (II), $R^4$ is —$(CH_2)_n$-$Q^2$-$(CH_2)_m$—, wherein $Q^2$ is selected from the group consisting of
(1) —O—,
(2) —O—C(=O)—,

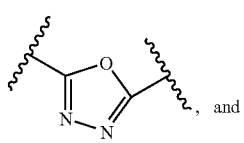

(3)

, and

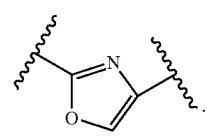

(4)

.

In this embodiment, n and m are preferably each 1.

In one embodiment of the compounds of formula (II), $R^3$ is as depicted in paragraph (1) below:

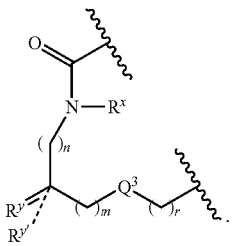

In this embodiment, $R^x$ is preferably hydrogen. In this embodiment, if the dotted line leading to $R^y$ is absent, $R^y$ is preferably selected from the group consisting of
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{0-6}$ alkylene-$C_{6-10}$ aryl, or
(f) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  wherein said alkyl, alkylene, alkenyl, alkynyl, cycloalkyl, aryl or heteroaryl are unsubstituted or substituted with one or more
    (i) halo,
    (ii) —$C_{1-10}$ alkyl,
    (iii) —OH,
    (iv) —CN, or
    (v) —O—$C_{1-10}$ alkyl, or
    (vi) —$C_{3-8}$ cycloalkyl,
  and $R^{y'}$ is preferably hydrogen.

In this embodiment, if the dotted line leading to $R^y$ represents a bond, then $R^y$ is preferably selected from the group consisting of
(a) =CH—$C_{1-10}$ alkyl, or
(b) =CH—$C_{0-6}$ alkylene-$C_{6-10}$ aryl,
  wherein said alkyl, alkylene, aryl or heteroaryl groups are unsubstituted or substituted with one or more
    (i) halo,
    (ii) —$C_{1-10}$ alkyl,
    (iii) —OH,
    (iv) —CN,
    (v) —O—$C_{1-10}$ alkyl, or
    (vi) —$C_{3-8}$ cycloalkyl.

In this embodiment, $Q^3$ is preferably —O— or —$CH_2$—, m is preferably 1, and n and r are preferably each 0.

In another embodiment of the compounds of formula (II), $R^3$ is as depicted in paragraph (2) below:

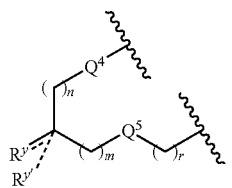

In this embodiment, if the dotted line leading to $R^y$ is absent, $R^y$ is preferably selected from the group consisting of
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{0-6}$ alkylene-$C_{6-10}$ aryl, or
(f) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said alkyl, alkylene, alkenyl, alkynyl, cycloalkyl, aryl or heteroaryl are unsubstituted or substituted with one or more
(i) halo,
(ii) —$C_{1-10}$ alkyl,
(iii) —OH,
(iv) —CN,
(v) —O—$C_{1-10}$ alkyl, or
(vi) —$C_{3-8}$ cycloalkyl,
and $R^{y'}$ is preferably hydrogen.

In this embodiment, if the dotted line leading to $R^y$ represents a bond, then $R^y$ is preferably selected from the group consisting of
(a) =CH—$C_{1-10}$ alkyl, or
(b) =CH—$C_{0-6}$ alkylene-$C_{6-10}$ aryl,
wherein said alkyl, alkylene, aryl or heteroaryl groups are unsubstituted or substituted with one or more
(i) halo,
(ii) —$C_{1-10}$ alkyl,
(iii) —OH,
(iv) —CN, or
(v) —O—$C_{1-10}$ alkyl, or
(vi) —$C_{3-8}$ cycloalkyl.

In this embodiment, preferably $Q^4$ is —O— or —$CH_2$— and $Q^5$ is —O— or —$CH_2$—. Preferably, n and m are each 1 and r is preferably 0.

In preferred embodiments of the compounds of formula (II), A is selected from the group consisting of
(1) hydrogen, and
(2) —$C_{1-10}$ alkyl,
wherein said alkyl is unsubstituted or substituted with one or more
(a) halo,
(b) —$C_{3-8}$ cycloalkyl,
(c) —CN
(d) —O—$C_{1-10}$ alkyl,
(e) phenyl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl.

In a more preferred embodiment of the compounds of formula (II), A is —$C_{1-10}$ alkyl (preferably methyl), wherein said alkyl is unsubstituted or substituted with one or more halo (preferably fluoro).

In a preferred embodiment of the compounds of formula (I), $R^2$ is selected from the group consisting of ($R^5$—$SO_2$)N($R^6$)—, wherein $R^5$ is —$C_{1-6}$ alkyl, wherein said alkyl is unsubstituted or substituted with one or more (i) halo,
(ii) —OH,
(iii) —CN,
(iv) —O—$C_{1-6}$ alkyl, or
(v) —$C_{1-6}$ alkyl,
$R^6$ is selected from the group consisting of
(a) hydrogen,
(b) —$C_{1-6}$ alkyl, or
(c) —$C_{6-10}$ aryl,
wherein said alkyl and aryl is unsubstituted or substituted with one or more
(i) halo,
(ii) —OH,
(iii) —CN,
(iv) —O—$C_{1-6}$ alkyl,
(v) $C_{1-6}$ alkyl,
or $R^5$ and $R^6$ may be linked to form a group —$CH_2(CH_2)_pCH_2$—.

Another preferred $R^2$ group is —$C_{6-10}$ aryl, unsubstituted or substituted as described above. Preferred aryl groups are phenyl groups, unsubstituted or substituted with cyano. A preferred $R^2$ substituent is shown below:

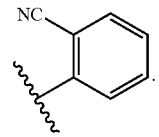

Another preferred $R^2$ substituent is

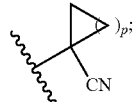

wherein p is 1, 2 or 3.

Another preferred $R^2$ substituent is heteroaryl, either unsubstituted or substituted as described above. Preferred heteroaryl groups include furanyl or oxazolyl, either unsubstituted or substituted as described above. A preferred furanyl or oxazolyl substituent is depicted below:

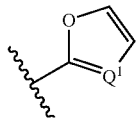

wherein $Q^1$ is selected from the group consisting of
(a) N, and
(b) C—$R^b$, wherein $R^b$ is selected from the group consisting of
(i) —CN, and
(ii) —C(=O)—O—$C_{1-10}$ alkyl,
(iii) —C(=O)—OH, and
(iv) —C(=O)—$NR^cR^d$,
(v) —$NR^cR^d$, wherein $R^c$ and $R^d$ are selected from the group consisting of
(A) hydrogen, and
(1) —$C_{1-10}$ alkyl.

Another embodiment of the present invention is directed to compounds of the formula (III)

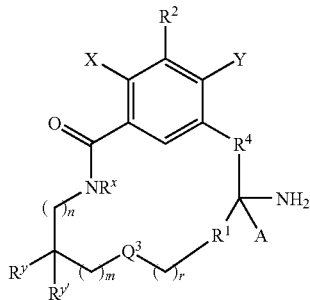

(III)

wherein A, X, Y, $R^1$, $R^2$, $R^4$, $R^x$, $R^y$, $R^{y'}$ $Q^3$, m, n and r are as defined above, and pharmaceutically acceptable salts thereof, and individual enantiomers and diastereomers thereof.

In a preferred embodiment of the compounds of formula (III), X and Y are both hydrogen.

In another preferred embodiment of the compounds of formula (III), $R^4$ is $-(CH_2)_n-Q^2-(CH_2)_m$, wherein $Q^2$ is selected from the group consisting of
(1) —O—,
(2) —C(=O)—,

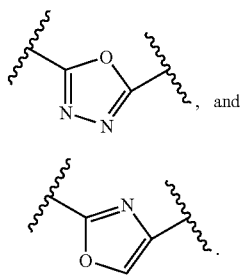

(3)

, and (4)

.

In this embodiment, n and m are preferably each 1.

In preferred embodiments of the compounds of formula (II), A is selected from the group consisting of
(1) hydrogen, and
(2) —$C_{1-10}$ alkyl,
wherein said alkyl is unsubstituted or substituted with one or more
(a) halo,
(b) —$C_{3-8}$ cycloalkyl,
(c) —CN,
(d) —O—$C_{1-10}$ alkyl,
(e) phenyl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl.

In a more preferred embodiment of the compounds of formula (III), A is —$C_{1-10}$ alkyl (preferably methyl), wherein said alkyl is unsubstituted or substituted with one or more halo (preferably fluoro).

In a preferred embodiment of the compounds of formula (III), $R^2$ is selected from the group consisting of ($R^5$—$SO_2$)N($R^6$)—, wherein $R^5$ is —$C_{1-6}$ alkyl, wherein said alkyl is unsubstituted or substituted with one or more
(i) halo,
(ii) —OH,
(iii) —CN,
(iv) —O—$C_{1-6}$ alkyl, or
(v) —$C_{1-6}$ alkyl,
$R^6$ is selected from the group consisting of
(a) hydrogen,
(b) —$C_{1-6}$ alkyl, or
(c) —$C_{6-10}$ aryl, or
wherein said alkyl or aryl is unsubstituted or substituted with one or more
(i) halo,
(ii) —OH,
(iii) —CN,
(iv) —O—$C_{1-6}$ alkyl,
(v) —$C_{1-6}$ alkyl,
or $R^5$ and $R^6$ may be linked to form a group —$CH_2(CH_2)_pCH_2$—.

Another preferred $R^2$ group is —$C_{6-10}$ aryl, unsubstituted or substituted as described above. Preferred aryl groups are phenyl groups, unsubstituted or substituted with cyano. A preferred $R^2$ substituent is shown below:

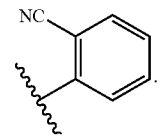

Another preferred $R^2$ substituent is

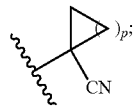

wherein p is 1, 2 or 3.

Another preferred $R^2$ substituent is heteroaryl, either unsubstituted or substituted as described above. Preferred heteroaryl groups include furanyl and oxazolyl, either unsubstituted or substituted as described above. A preferred furanyl or oxazolyl substitutent is depicted below:

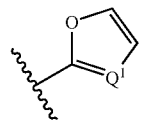

wherein $Q^1$ is selected from the group consisting of
(a) N, and
(b) C—$R^b$, wherein $R^b$ is selected from the group consisting of
(i) —CN, and
(ii) —C(=O)—O—$C_{1-10}$ alkyl,
(iii) —C(=O)—OH, and
(iv) —C(=O)—$NR^cR^d$, (v) —NR$^c$R$^d$, wherein R$^c$ and R$^d$ are selected from the group consisting of
  (A) hydrogen, and
  (B) —C$_{1-10}$ alkyl.

Another embodiment of the present invention is directed to compounds of the formula (IV):

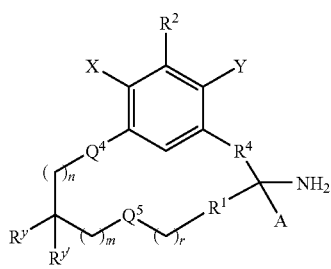

wherein A, X, Y, R$^1$, R$^2$, R$^4$, R$^y$, R$^{y'}$ Q$^4$, Q$^5$, m, n and r are as defined above, and pharmaceutically acceptable salts thereof, and individual enantiomers and diastereomers thereof.

In a preferred embodiment of the compounds of formula (IV), X and Y are both hydrogen.

In another preferred embodiment of the compounds of formula (IV), R$^4$ is —(CH$_2$)$_n$-Q$^2$-(CH$_2$)$_m$, wherein Q$^2$ is selected from the group consisting of
  (1) —O—,
  (2) —O—C(=O)—,

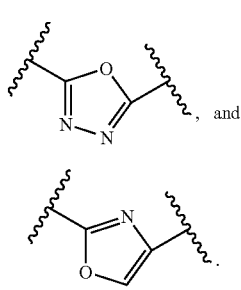

In this embodiment, n and m are preferably each 1.

In preferred embodiments of the compounds of formula (IV), A is selected from the group consisting of
  (1) hydrogen, and
  (2) —C$_{1-10}$ alkyl,
  wherein said alkyl is unsubstituted or substituted with one or more
    (a) halo,
    (b) —C$_{3-8}$ cycloalkyl,
    (c) —CN,
    (d) —O—C$_{1-10}$ alkyl,
    (e) phenyl, or
    (f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl.

In a more preferred embodiment of the compounds of formula (IV), A is —C$_{1-10}$ alkyl (preferably methyl), wherein said alkyl is unsubstituted or substituted with one or more halo (preferably fluoro).

In a preferred embodiment of the compounds of formula (IV), R$^2$ is selected from the group consisting of (R$^5$—SO$_2$)N(R$^6$)—, wherein R$^5$ is —C$_{1-6}$ alkyl, wherein said alkyl is unsubstituted or substituted with one or more
  (i) halo,
  (ii) —OH,
  (iii) —CN,
  (iv) —O—C$_{1-6}$ alkyl, or
  (v) —C$_{1-6}$ alkyl,
R$^6$ is selected from the group consisting of
  (a) hydrogen,
  (b) —C$_{1-6}$ alkyl, or
  (c) —C$_{6-10}$ aryl,
    wherein said alkyl and aryl is unsubstituted or substituted with one or more
      (i) halo,
      (ii) —OH,
      (iii) —CN,
      (iv) —O—C$_{1-6}$ alkyl,
      (v) —C$_{1-6}$ alkyl,
  or R$^5$ and R$^6$ may be linked to form a group —CH$_2$(CH$_2$)$_p$CH$_2$—.

Another preferred R$^2$ group is —C$_{6-10}$ aryl, unsubstituted or substituted as described above. Preferred aryl groups are phenyl groups, unsubstituted or substituted with cyano. A preferred R$^2$ substituent is shown below:

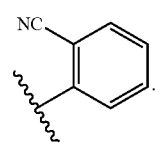

Another preferred R$^2$ substituent is

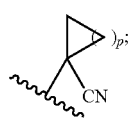

wherein p is 1, 2 or 3.

Another preferred R$^2$ substituent is heteroaryl, either unsubstituted or substituted as described above. Preferred heteroaryl groups include furanyl or oxazolyl, either unsubstituted or substituted as described above. A preferred furanyl or oxazolyl substituent is depicted below:

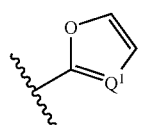

wherein Q$^1$ is selected from the group consisting of
  (a) N, and
  (b) C—R$^b$, wherein R$^b$ is selected from the group consisting of
    (i) —CN, and
    (ii) —C(=O)—O—C$_{1-10}$ alkyl,
    (iii) —C(=O)—OH, and (iv) —C(=O)—NR$^c$R$^d$,
(v) —NR$^c$R$^d$, wherein R$^c$ and R$^d$ are selected from the group consisting of
(A) hydrogen, and
(B) —C$_{1-10}$ alkyl.

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., C$_{1-10}$ alkyl means an alkyl group having from one to ten carbon atoms). Preferred alkyl groups for use in the invention are C$_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkylene," by itself or as part of another substituent, means a saturated straight or branched chain divalent hydrocarbon radical having the number of carbon atoms designated. The term "C$_0$ alkylene" means a bond.

As used herein, the term "cycloalkyl," by itself or as part of another substituent, means a saturated cyclic hydrocarbon radical having the number of carbon atoms designated (e.g., C$_{3-8}$ cycloalkyl means a cycloalkyl group having from three to eight carbon atoms). Exemplary cycloalkyl groups include cyclopropyl, cyclobutyl, cyclopentyl, cyclohexyl and the like.

As used herein, the term "alkenyl," by itself of as part of another substituent, means a straight or branched chain hydrocarbon radical having a single carbon-carbon double bond and having the number of carbon atoms designated (e.g., C$_{2-10}$ alkenyl means an alkenyl group having from one to ten carbon atoms). Preferred alkenyl groups for use in the invention are C$_{2-6}$ alkenyl groups, having from two to six carbon atoms. Exemplary alkenyl groups include ethenyl, n-propenyl, isopropenyl, butenyl, and the like.

As used herein, the term "alkynyl", by itself or as part of another substituent, means a saturated straight or branched chain hydrocarbon radical having the number of carbon atoms designated (e.g., C$_{2-10}$ alkynyl means an alkynyl group having from two to ten carbon atoms). Preferred alkynyl groups for use in the invention are C$_{2-6}$ alkynyl groups, having from two to six carbon atoms. Exemplary alkynyl groups include ethynyl and propynyl.

As used herein, the term "aryl," by itself or as part of another substituent, means an aromatic or cyclic radical having the number of carbon atoms designated (e.g., C$_{6-10}$ aryl means an aryl group having from six to ten carbons atoms). The term "aryl" includes multiple ring systems as well as single ring systems. Preferred aryl groups for use in the invention include phenyl and naphthyl.

As used herein, the term "arylene," by itself or as part of another substituent, means a divalent aromatic or cyclic radical. having the number of carbon atoms designated (e.g., C$_{6-10}$ arylene means an arylene group having from six to ten carbons atoms). The term "arylene" includes multiple ring systems as well as single ring systems. Preferred arylene groups for use in the invention include phenylene and naphthylene.

As used herein, the term "heteroaryl," by itself or as part of another substituent, means an aromatic cyclic radical having at least one ring heteroatom (O, N or S). The term "heteroaryl" includes multiple ring systems as well as single ring systems. Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, benzimidazolyl, quinolinyl, isoquinolinyl, tetrazolyl, indazolyl, napthyridinyl, triazolyl, oxazolyl, oxadiazolyl, thiazolyl, thiadiazolyl, isoxazolyl, tetrahydroquinolinyl, tetrahydroisoquinolinyl and dihydroindolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "heteroarylene," by itself or as part of another substituent, means an aromatic cyclic divalent radical having at least one ring heteroatom (O, N or S).

The term "halo" or "halogen" includes fluoro, chloro, bromo and iodo.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of formulas (I) to (IV), the carbon to which A and R$^4$ are bonded is a chiral carbon. As a result, the compounds of formulas (I)-(IV) may be present as racemates, or in the stereochemically pure (R) or (S) forms. The present invention encompasses all such isomeric forms.

The (R) and (S) configurations for compounds of formula (I) are depicted below:

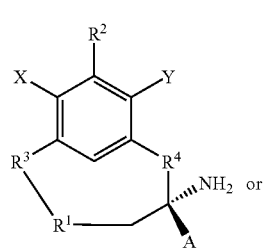

(R)

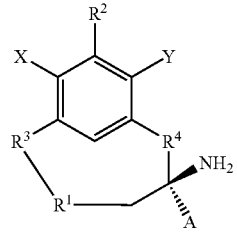

(S)

The (R) configuration (as depicted above) is preferred.

In the compounds of formula (III) and (IV), and the compounds of (I) and (II) when the dotted line leading to $R^y$ is absent, the carbon to which $R^y$ is bonded is chiral. As a result, the compounds of the invention may be present as racemates, or in the stereochemically pure (R) or (S) forms. The present invention encompasses all such isomeric forms.

The (R) and (S) configurations for compounds of formula (III) are depicted below:

(R)

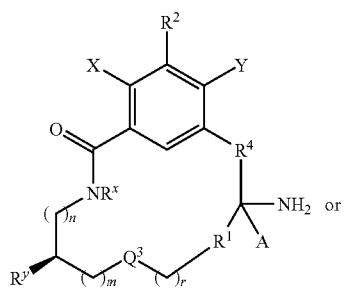

(S)

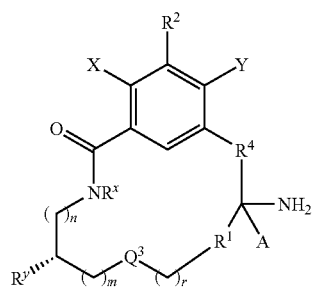

As will be understood by persons of ordinary skill in the art, some of the compounds of the invention may be present as racemates, or as diastereomers (R,S), (R,R), (S,R), and (S,S).

The compounds of the present invention are prepared by the methods outlined in Schemes 1.1 to 4.10, below, and the intermediates and examples herein.

Scheme 1.1, describes the preparation of hydroxyl derivatives of type 1.1a, their triflate analogs 1.1b and 1.1c. Starting from glycine Schiff base, more elaborated bromides of type 1.1d and 1.1e can be prepared.

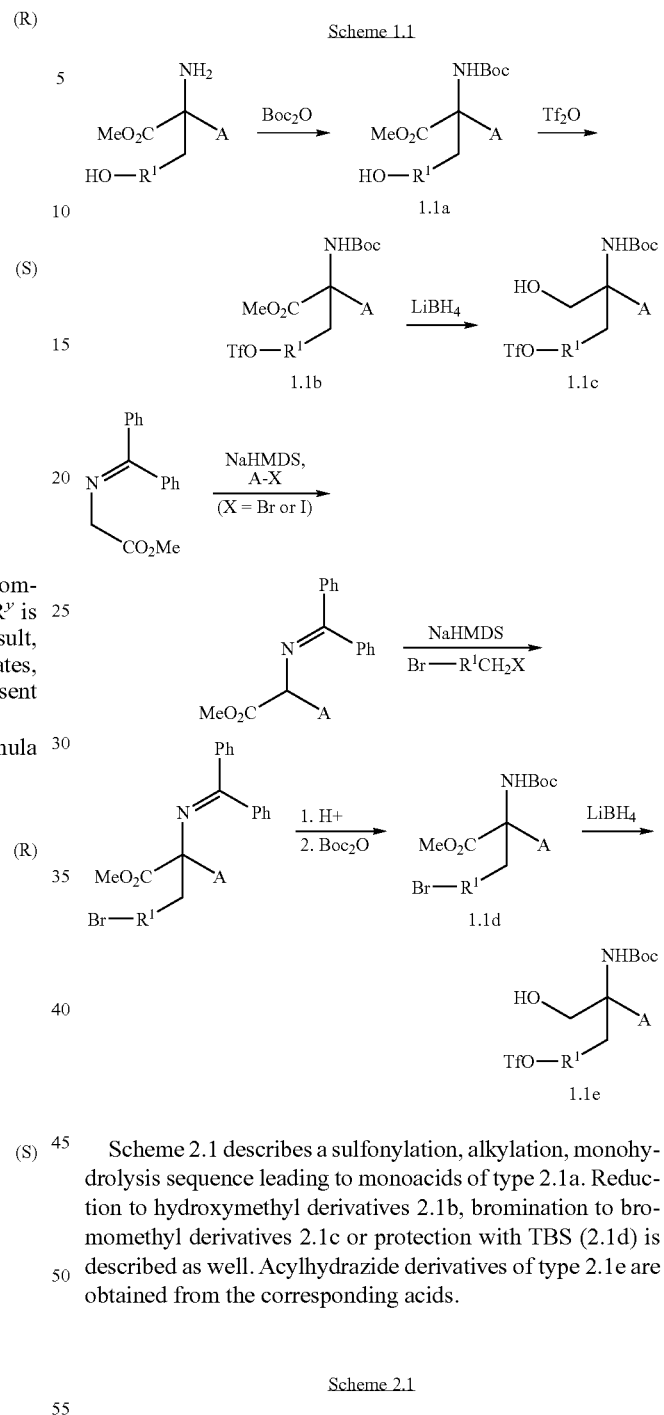

Scheme 2.1 describes a sulfonylation, alkylation, monohydrolysis sequence leading to monoacids of type 2.1a. Reduction to hydroxymethyl derivatives 2.1b, bromination to bromomethyl derivatives 2.1c or protection with TBS (2.1d) is described as well. Acylhydrazide derivatives of type 2.1e are obtained from the corresponding acids.

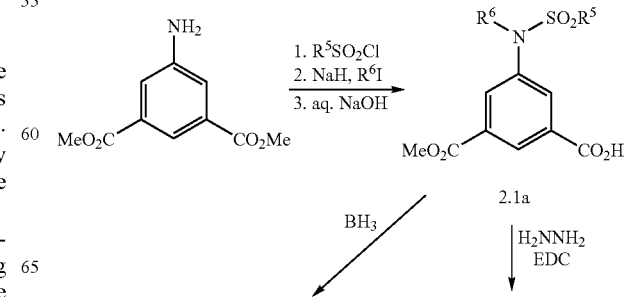

-continued

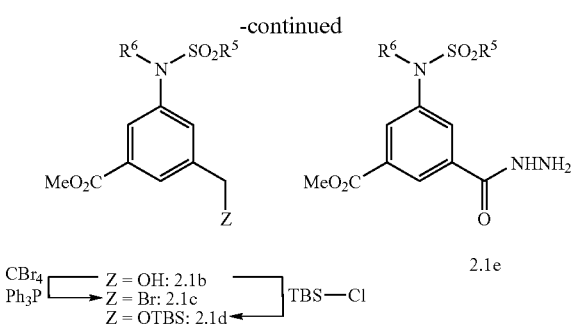

Scheme 2.2 describes very similar preparation as in scheme 2.1 with the incorporation of a tert-butyl ester that can be removed under non-hydrolytic conditions. Alternate mode of alkylation/sulfonylation is also represented.

Scheme 2.3 is similar to schemes 2.1 and 2.2, with the incorporation of an aryl bromide useful to introduce various aryl groups, sulfonamides and heterocycles later in the syntheses or early on as described in the 2$^{nd}$ part of the scheme.

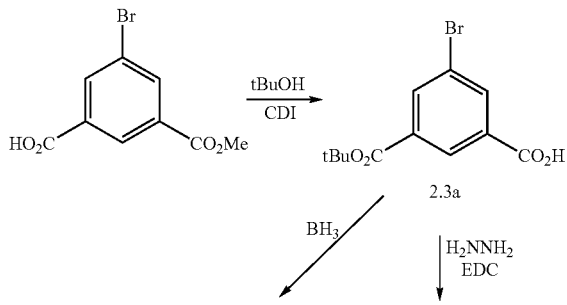

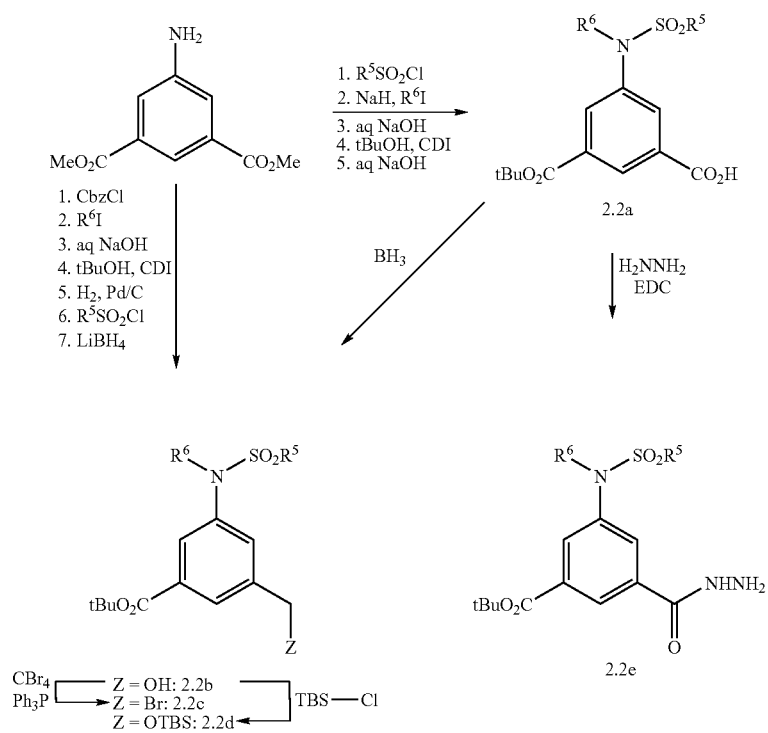

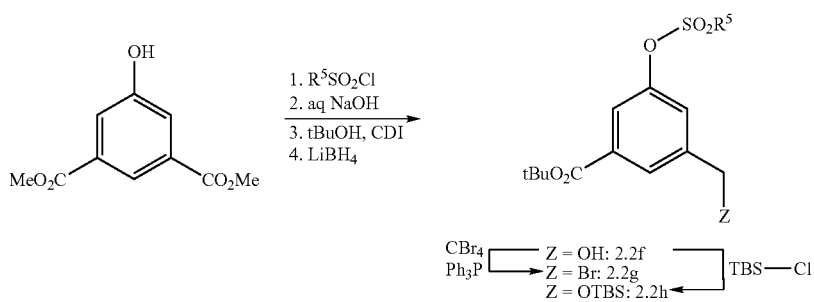

-continued

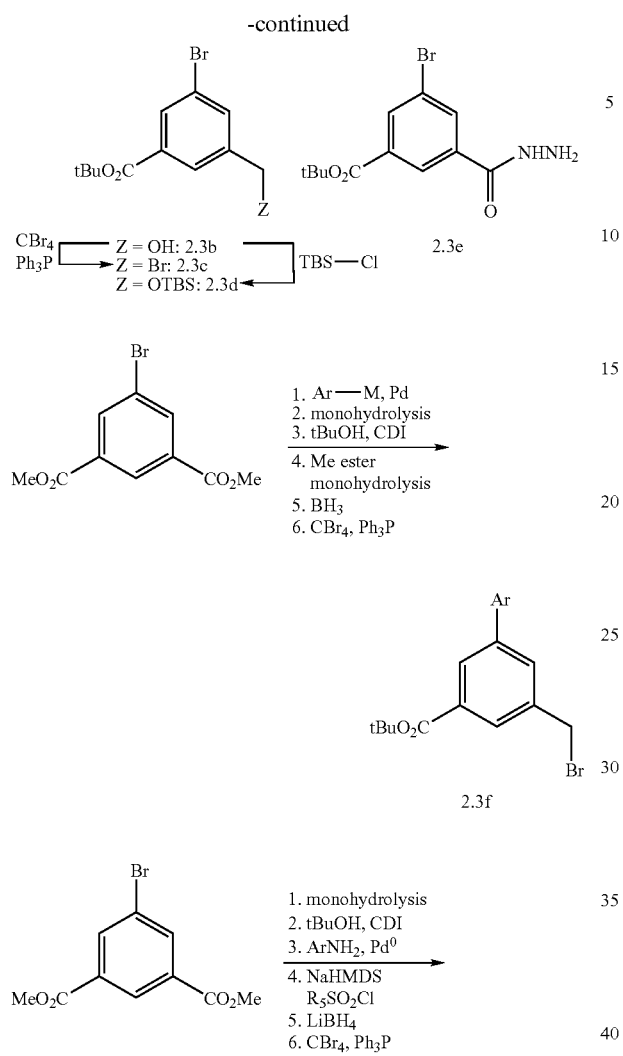

Scheme 2.4 describes the preparation of similar intermediates that display cyano-spirocyclic groups to replace the alkyl-sulfonamides described in schemes 2.1 and 2.2.

Scheme 2.4

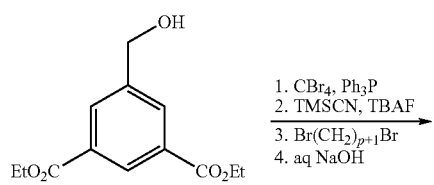

-continued

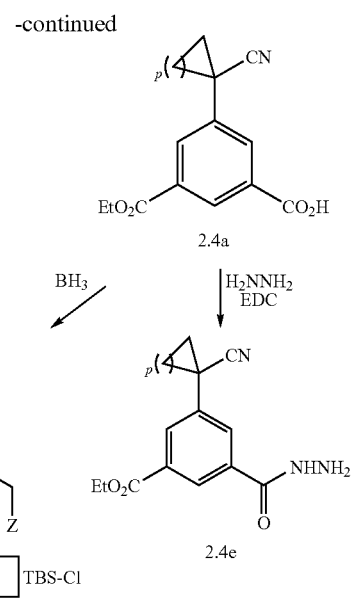

Scheme 2.5 describes the preparation of phenols of type 2.5b and 2.5d, along with their triflate derivatives of type 2.5c and 2.5e.

Scheme 2.5

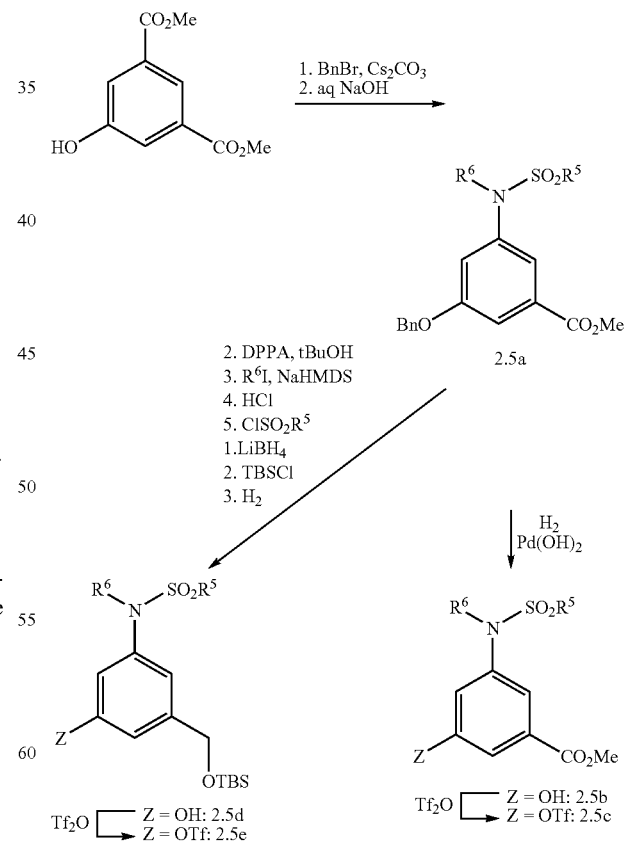

Scheme 3.1 and 3.2 illustrate the preparation of carboxylic acids of type 3.1-2a and alcohols of type 3.1-2c.

Scheme 3.1
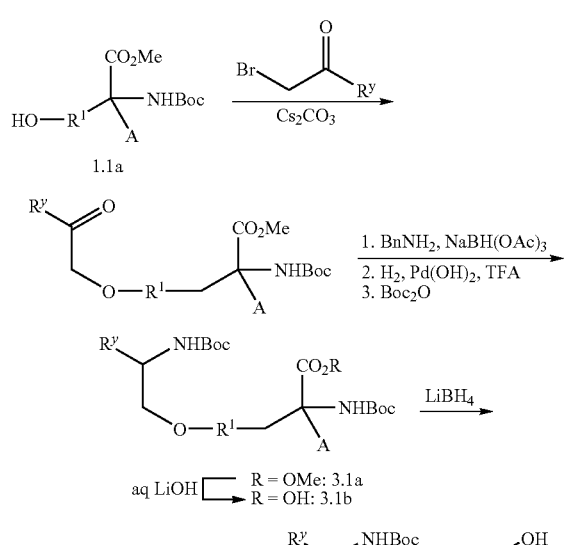
Scheme 3.2
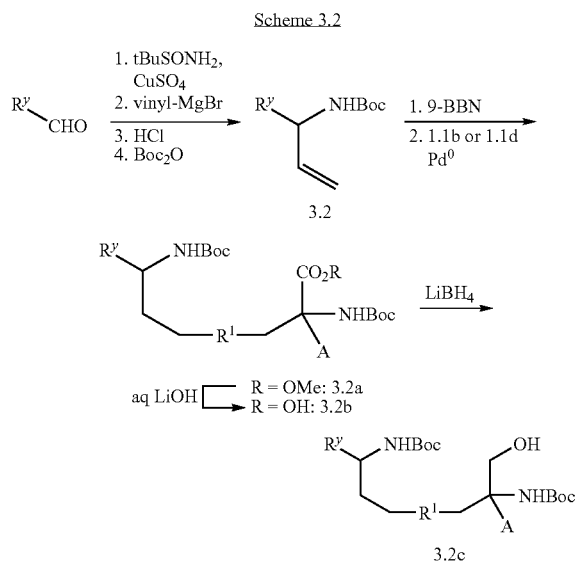
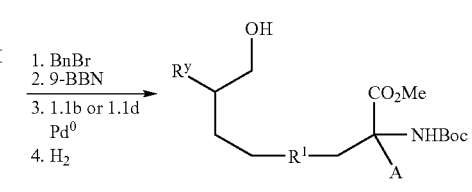
Schemes 3.3, 3.4, and 3.5 describe the preparation of esters of types 3.3-5a
Scheme 3.3
Scheme 3.4
Scheme 3.5
Schemes 4.1-10 illustrate the assembly of various intermediates and their final elaboration to macrocycles.
Scheme 4.1
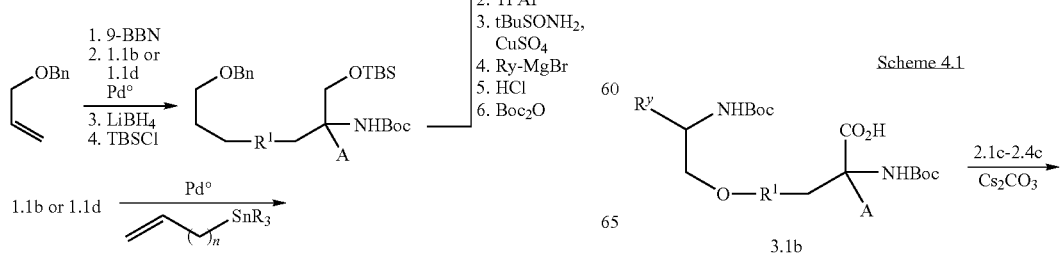

-continued
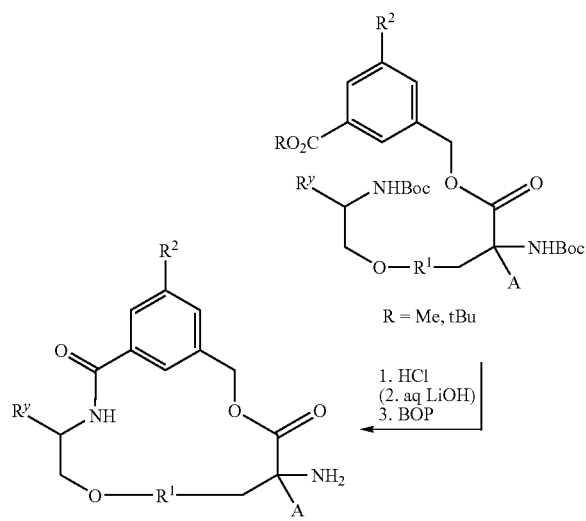
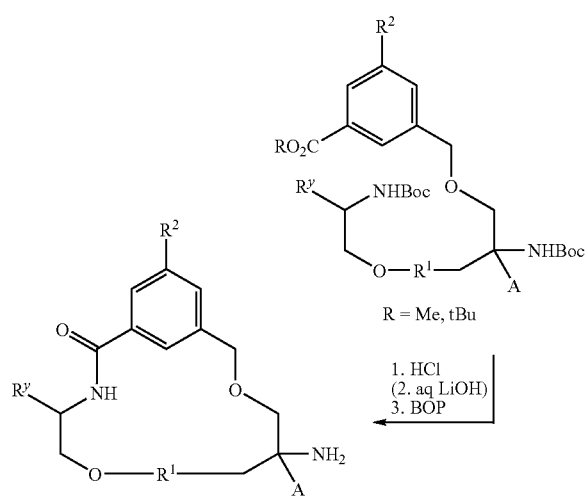
Scheme 4.2
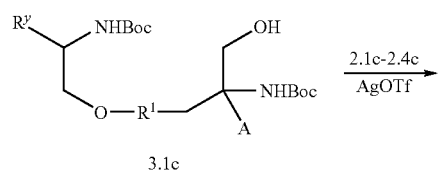
-continued
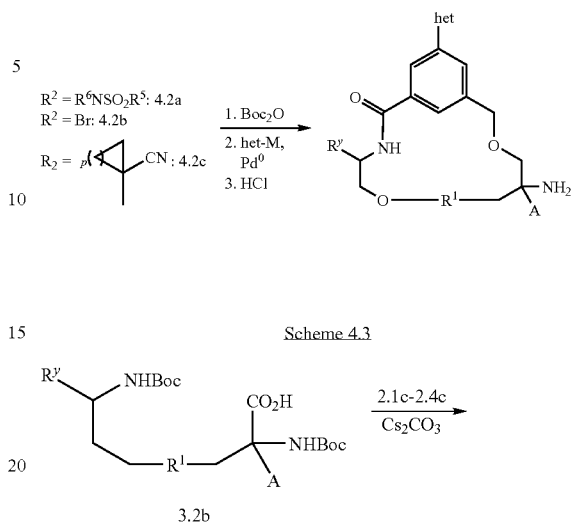
Scheme 4.3
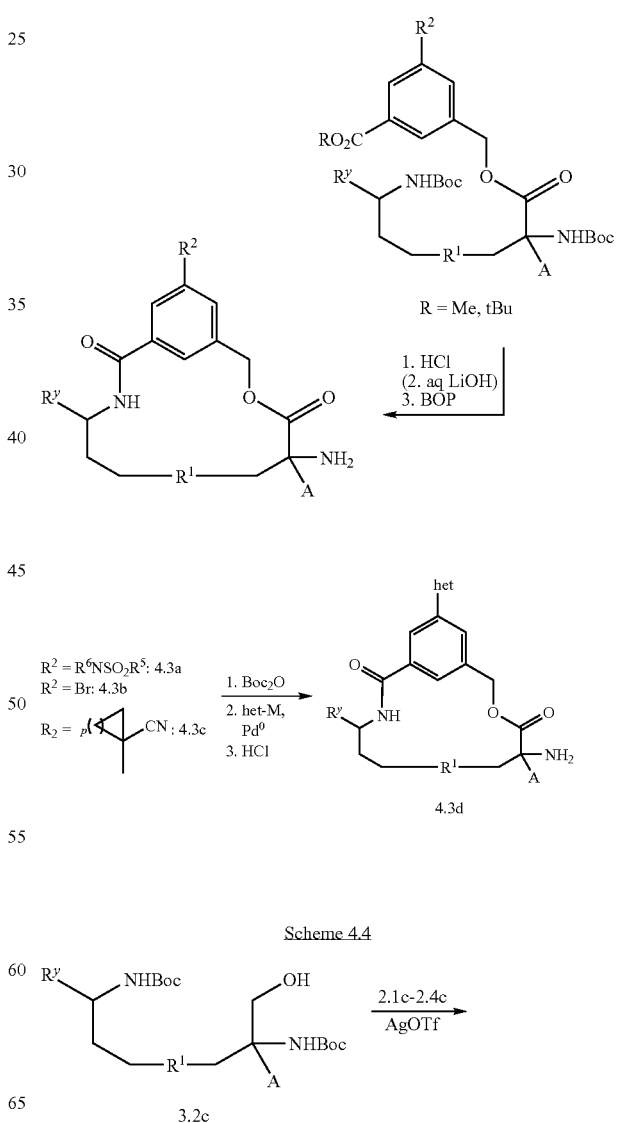
Scheme 4.4

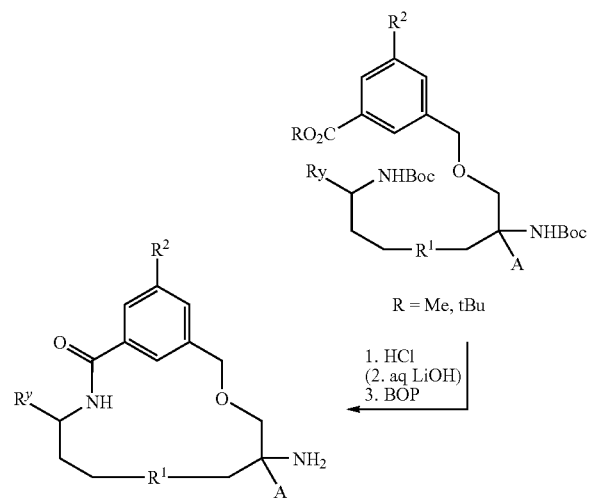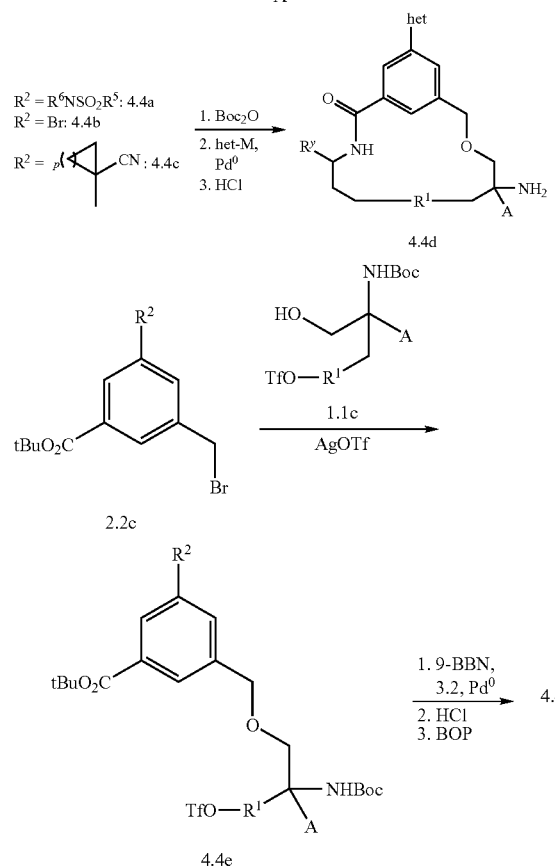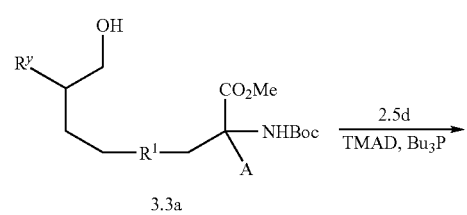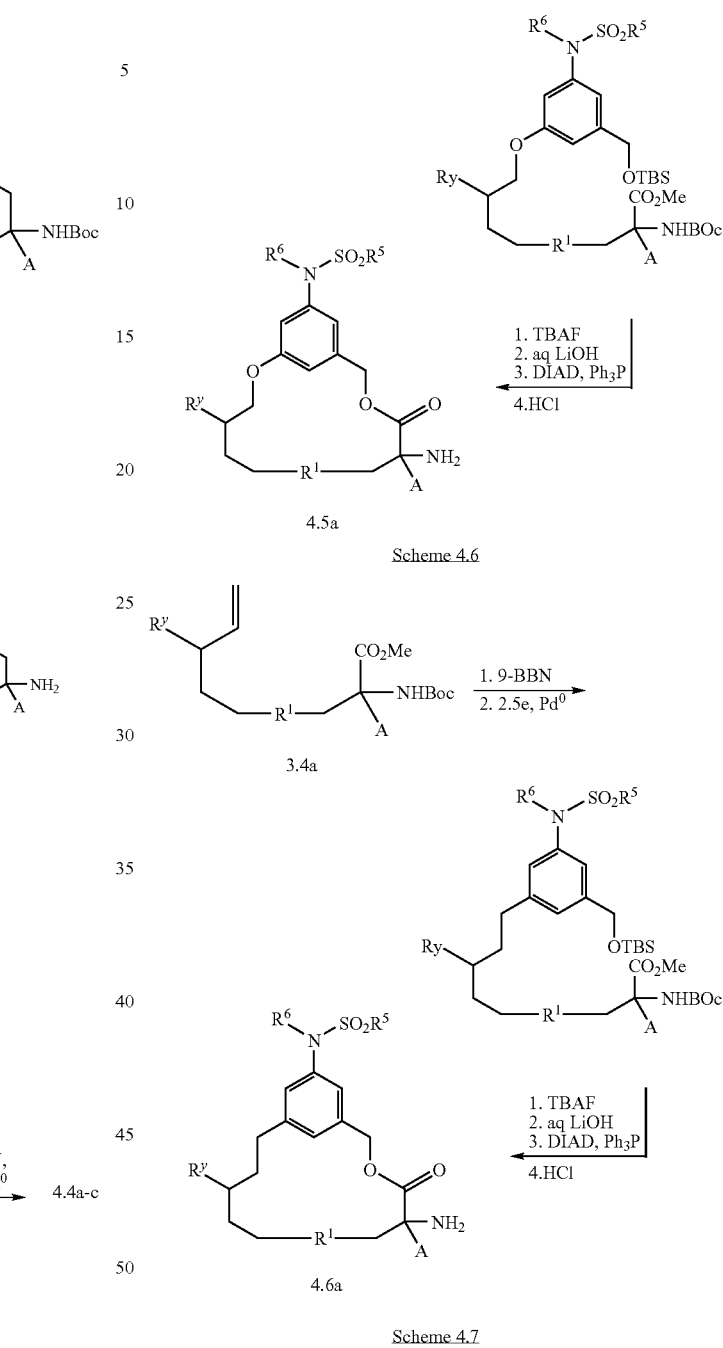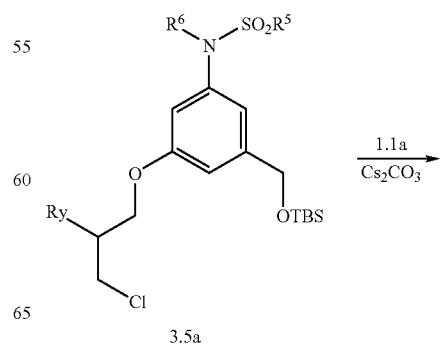

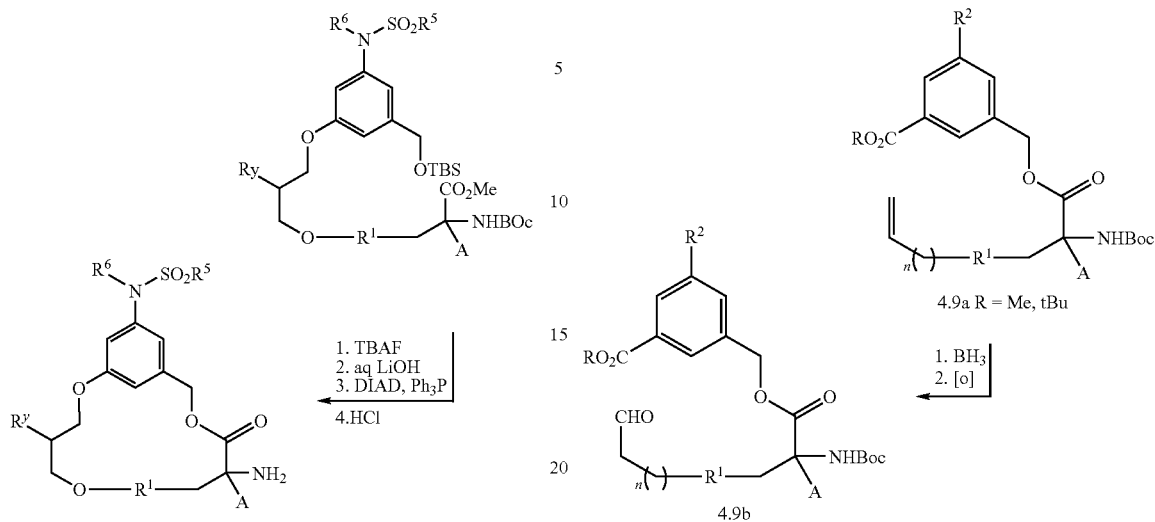
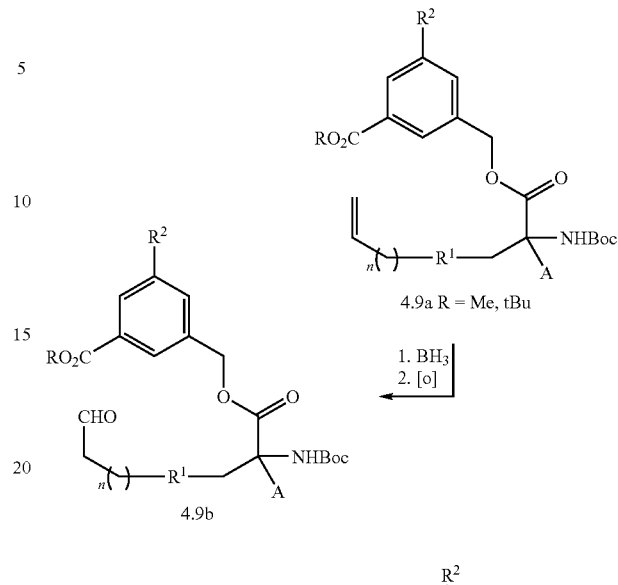
Scheme 4.8
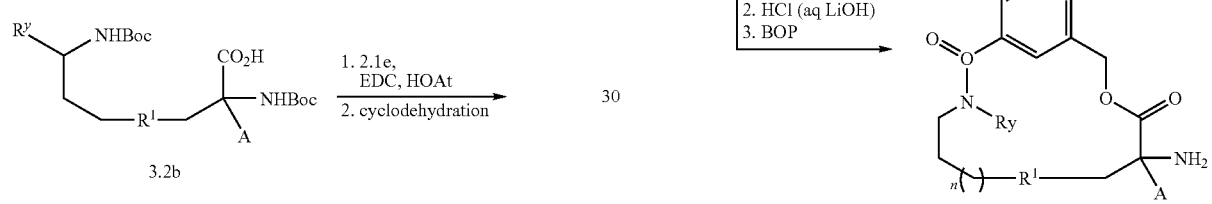
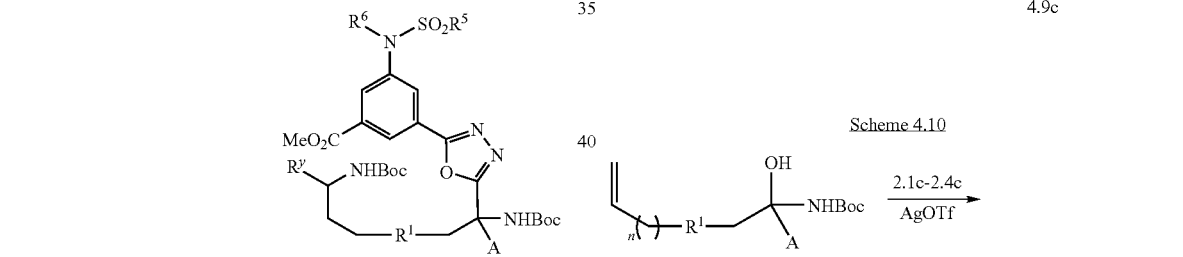
Scheme 4.9
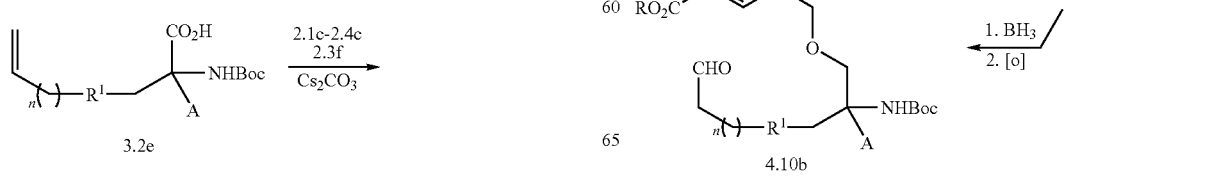
Scheme 4.10
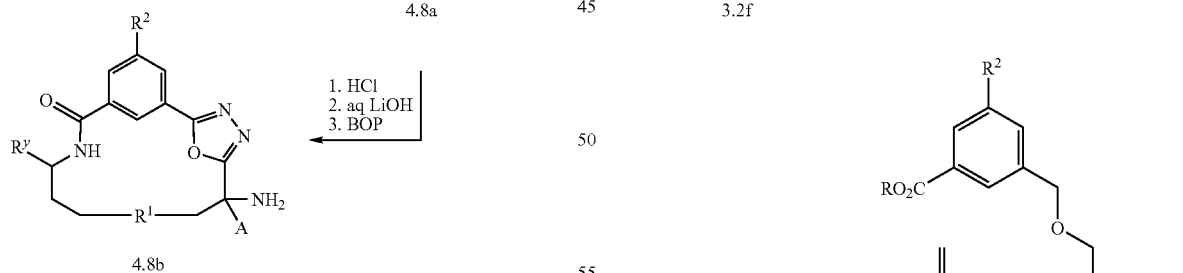

-continued

1. Ry-NH₂, NaBH(OAc)₃
2. HCl (aq LiOH)
3. BOP

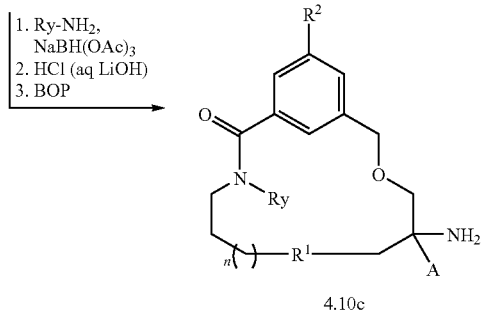

4.10c

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, trifluoroacetic acid and the like. Particularly preferred are citric, hydrobromic, hydrochloric, maleic, phosphoric, sulfuric, fumaric, tartaric and trifluoroacetic acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phpsphorylation inhibitors; M1 receptor positive allosteric modulators; blockers of Aβ oligomer formation; 5-HT modulators, such as PRX-03140, GSK 742467, SGS-518, FK-962, SL-65.0155, SRA-333 and xaliproden; p25/CDK5 inhibitors; NK1/NK3 receptor antagonists; COX-2 inhibitors; HMG-CoA reductase inhibitors; NSAIDs including ibuprofen; vitamin E; anti-amyloid antibodies, including anti-amyloid humanized monoclonal antibodies; anti-inflammatory compounds such as (R)-flurbiprofen, nitroflurbiprofen, rosiglitazone, ND-1251, VP-025, HT-0712 and EHT-202; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ antagonists such as ABT-834, ABT 829 and GSK 189254; AMPA agonists or AMPA modulators, such as CX-717, LY 451395 and S-18986; PDE IV inhibitors; $GABA_A$ inverse agonists; neuronal nicotinic agonists; selective M1 agonists; microtobubule affinity regulating kinase (MARK) ligands; P-450 inhibitors, such as ritonavir, or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating Alzheimer's disease or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of α-secretase enzyme activity may be demonstrated by methodology known in the art. Enzyme inhibition may be determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency of compounds, solutions of inhibitor in DMSO (four concentrations of the inhibitors are prepared: 1 mM, 100 μM, 10 μM, 1 μM) are included in the reactions mixture (final DMSO concentration is 0.8%). All experiments are conducted at rt using the standard reaction conditions described above. To determine the $IC_{50}$ of the compound, competitive equation $V0/Vi=1+[I]/[IC50]$ is used to predict the inhibitory potency of the compounds. The errors in reproducing the dissociation constants are typically less than two-fold.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by FRET) are included in the reaction mixture (final DMSO concentration is 10%). All experiments are conducted at rt using the standard reaction conditions described above. To determine the $IC_{50}$ of the compound, four parameters equation is used for curve fitting. The errors in reproducing the dissociation constants are typically less than two-fold.

In particular, the compounds of the following examples had activity in inhibiting the beta-secretase enzyme in one or both of the aforementioned assays, generally with an $IC_{50}$ from about 1 nM to 100 μM. Such a result is indicative of the intrinsic activity of the compounds in use as inhibitors of the beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Me: methyl
Et: ethyl
Bu: butyl
t-Bu: tert-butyl
Ar: aryl
Ph: phenyl
Ac: acetyl
Bn: benzyl
Boc: tert-butyloxy carbonyl
TFA: trifluoroacetic acid
DCM: dichloromethane
DMF: N,N'-dimethyl formamide
TBAF: tetra-n-butylammonium fluoride
HMDS: hexamethyldisilazane
THF: tetrahydrofuran
DMSO: dimethylsulfoxide
EDTA: ethylene diamine tetraacetic acid
BOP: Benzotriazol-1-yloxy-tris(dimethylamino)phosphonium hexafluorophosphate
TMS: trimethylsilyl
TBS: tert-butyl silyl
TMAD: N,N,N',N'-Tetramethylazocarboxamide
DIAD: Diisopropylazodicarboxylate
HOAt: 1-hydroxy-7-azabenzotriazole
EDC: 1-Ethyl-3-(3-dimethylaminopropyl)-carbodiimide
DPPA: diphenylphosphorylazide
TPAP: tetrapropylammonium perruthenate
BSA: bovine serum albumin
CHAPS: 3-[(3-cholamidopropyl)dimethylammonio]-2-hydroxy-1-propanesulfonate
rt: room temperature
HPLC: high performance liquid chromatography Intermediate I.1.a.1 (Scheme 1.1)

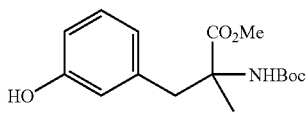

To a suspension of alphamethyl m-tyrosine methyl ester hydrochloride monohydrate (10.4 g, 39.4 mmol) in THF (300 mL) was added diisopropylethyl amine (7.6 mL, 43.4 mmol) and ditertbutyldicarbonate (9.1 g, 41.4 mmol) and the reaction mixture was stirred at rt for 24 h. The reaction mixture was concentrated in vacuo to ½ volume, diluted with EtOAc and diethyl ether, washed with 10% aq $KHSO_4$, and then alternatively with water and brine until aq pH=7, dried over $Na_2SO_4$, concentrated in vacuo, and purified by flash chromatography (300 g silica, 0-60% EtOAc in hexanes) to provide intermediate I.1.a.1. $^1$H NMR (400 MHz, $CDCl_3$) δ 7.12 (app. t, J=8 Hz, 1H), 6.72 (dd, J=8, 2.4 Hz, 1H), 6.63 (d, J=8 Hz, 1H), 6.58 (dd, J=2.5, 2.4 Hz, 1H), 5.35 (br s, 1H), 5.16 (br s, 1H), 3.75 (s, 3H), 3.28 (m, 1H), 3.15 (B of AB, d, J=13.3 Hz, 1H), 1.55 (br s, 3H), 1.47 (s, 9H).

Intermediate I.1.b.1 (Scheme 1.1)

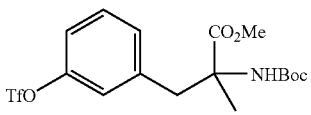

To a solution of intermediate I.1.a.1 (6.62 g, 21.4 mmol) in DCM (50 mL) cooled to 0° C. was added 2,6-lutidine (2.9 mL, 24.6 mmol) and triflic anhydride (4 mL, 23.5 mmol) dropwise. The reaction mixture was stirred at 0° C. for 10 min, diluted with water, extracted with DCM twice. The combined organic fraction was dried over $Na_2SO_4$, concentrated in vacuo, and purified by flash chromatography (300 g silica, 0-30% EtOAc in hexanes) to provide intermediate I.1.b.1. $^1$H NMR (400 MHz, $CDCl_3$) δ 7.35 (app. t, J=8 Hz, 1H), 7.15 (dd, J=8, 2.4 Hz, 1H), 7.11 (d, J=8 Hz, 1H), 7.0 (dd, J=2.5; 2.4 Hz, 1H), 5.19 (br s, 1H), 3.77 (s, 3H), 3.52 (A of AB, br d, J=13.6 Hz, 1H), 3.27 (B of AB, d, J=13.6 Hz, 1H), 1.56 (s, 3H), 1.48 (s, 9H).

Intermediate I.1.b.2 (Scheme 1.1)

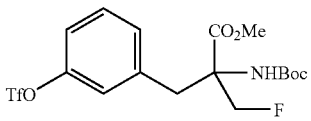

Step A: 1-((3-(Bromomethyl)phenoxy)methyl)benzene

To a solution of 3-benzyloxybenzyl alcohol (2 g, 9.3 mmol) and carbon tetrabromide (4 g, 12.1 mmol) in $CH_2Cl_2$ (70 mL), cooled to 0° C., was added a solution of triphenylphosphine (2.9 g, 11.2 mmol) in $CH_2Cl_2$ (20 mL). The reaction was stirred at rt for 3 h and concentrated. Purification by flash chromatography (silica gel, 0-8% EtOAc/hexanes) gave 1-((3-(bromomethyl)phenoxy)methyl)benzene. $^1$H NMR (400 MHz, $CDCl_3$) δ 7.39 (m, 5H), 7.25 (m, 1H), 7.00 (m, 2H), 6.92 (m, 1H), 5.06 (s, 2H), 4.46 (s, 2H).

Step B: 2-Amino-3-(3-benzyloxy)phenyl)-2-(fluoromethyl)propanenitrile

To a suspension of magnesium (0.46 g, 0.019 mol) and iodine (cat amt) in THF (42 mL) was added a solution of 1-((3-(bromomethyl)phenoxy)methyl)benzene (4.5 g, 0.016 mol) in THF (21 mL) dropwise over 45 min. The reaction was stirred at rt for 1.5 h, cooled to −40° C. and a solution of fluoroacetonitrile (0.83 mL, 0.015 mol) in THF (5 mL) was added dropwise. The reaction mixture was stirred at −40° C. for 15 min and then added via cannula to a solution of sodium cyanide (1.6 g, 0.032 mol) and ammonium chloride (1.6 g, 0.029 mol) in $H_2O$ (32 mL). After stirring at rt for 1 h, sodium chloride (6.3 g) was added and the mixture was extracted with ether. Drying and solvent evaporation gave 2-amino-3-(3-benzyloxy)phenyl)-2-(fluoromethyl)propanenitrile. $^1$H NMR (400 MHz, $CDCl_3$) δ 7.43-7.28 (m, 6H), 6.95 (m, 3H), 5.07 (s, 2H), 4.38 (ABX, J=46 Hz, J=9 Hz, 2H), 2.99 (d, J=14 Hz, 1H), 2.77 (d, J=14 Hz, 1H).

Step C: 2-Amino-2-(fluoromethyl)-3-(3-hydroxyphenyl) propanoic acid

A solution of 2-amino-3-(3-benzyloxy)phenyl)-2-(fluoromethyl)propanenitrile (4.5 g, 0.016 mol) in aqueous HCl (6N, 60 mL) was heated to 90° C. for 96 h. the reaction mixture was diluted with $H_2O$ and extracted with ether. The pH of the aqueous phase was brought to 5.5 and solid impurities were filtered. Concentration of the aqueous layer gave 2-amino-2-(fluoromethyl)-3-(3-hydroxyphenyl)propanoic acid. $^1$H NMR (400 MHz, $CD_3OD$) δ 7.15 (m, 2H), 6.74 (m, 2H), 4.69 (m, 2H), 3.19 (d, J=14 Hz, 1H), 2.96 (d, J=14 Hz, 1H).

Step D: Methyl 2-amino-2-(fluoromethyl)-3-(3-hydroxyphenyl)propanoate

To a solution of 2-amino-2-(fluoromethyl)-3-(3-hydroxyphenyl)propanoic acid (1 g, 4.7 mmol) in MeOH (10 mL) was added thionyl chloride (3.9 mL, 54 mmol) dropwise and the reaction mixture was heated to 60° C. for 48 h. Additional thionyl chloride (2 mL) was added and the reaction continued for 48 h. Quenching with $H_2O$, concentration and trituration from MeCN gave methyl 2-amino-2-(fluoromethyl)-3-(3-hydroxyphenyl)propanoate. $^1$H NMR (400 MHz, $CDCl_3$) δ 7.20 (m, 2H), 6.66 (m, 2H), 4.83-4.37 (ABX, J=46 Hz, J=8.8 Hz, 2H), 3.76 (s, 3H), 3.04 (d, J=13 Hz, 1H), 2.69 (d, J=13 Hz, 1H).

Step E: Methyl 2-tert-butoxycarbonylamino-2-(fluoromethyl)-3-(3-hydroxyphenyl)propanoate To a suspension of methyl 2-amino-2-(fluoromethyl)-3-(3-hydroxyphenyl)propanoate (1 g, 3.8 mmol) in DMF/tert-butanol (1:1, 2.6 mL) was added a solution of di-tert-butyl dicarbonate (1.6 g, 7.6 mmol) in DMF/tert-butanol (0.9 mL) followed by sodium bicarbonate (1.1 g, 13.3 mmol). The reaction was heated to 60° C. for 1.5 h, quenched with 10% citric acid solution and extracted with EtOAc. Drying, solvent evaporation and flash chromatography (silica gel, 0-25% EtOAc/hexanes) gave methyl 2-tert-butoxycarbonylamino-2-(fluoromethyl)-3-(3-hydroxyphenyl)propanoate. $^1$H NMR (400 MHz, $CDCl_3$) δ 7.13 (t, J=7.9 Hz, 1H), 6.72 (dd, J=8 Hz, J=2.2 Hz, 1H), 6.63 (d, J=7.6 Hz, 1H), 6.58 (s, 1H), 5.36 (bs, 1H), 5.26 (bs, 1H), 5.07-4.64 (ABX, J=47 Hz, J=8 Hz, 2H), 3.78 (s, 3H), 3.36 (d, J=13 Hz, 1H), 2.96 (d, J=13 Hz, 1H), 1.46 (s, 9H).

Step F: 3-(2-(Methoxycarbonyl)-2-tert-butoxycarbonylamino-3-fluoropropyl)phenyl trifluoromethanesulfonate To a solution of methyl 2-tert-butoxycarbonylamino-2-(fluoromethyl)-3-(3-hydroxyphenyl)propanoate (87 mg, 0.26 mmol) and DIEA (0.056 mL, 0.32 mmol) in MeCN (4.6 mL) was added N-phenyltrifluoromethanesulfonimide (114 mg, 0.32 mmol). The reaction was stirred at rt overnight, concentrated, diluted with EtOAc and washed with H₂O and brine. Drying, solvent evaporation and flash chromatography (silica gel, 0-25% EtOAc/hexanes) gave 3-(2-(methoxycarbonyl)-2-tert-butoxycarbonylamino-3-fluoropropyl)phenyl trifluoromethanesulfonate. ¹H NMR (400 MHz, CDCl₃) δ 7.39-7.03 (m, 4H), 5.45 (bs, 1H), 5.11-4.62 (ABX, J=46 Hz, J=8.7 Hz, 2H), 3.79 (s, 3H), 3.55 (d, J=13 Hz, 1H), 3.04 (d, J=13 Hz, 1H), 1.48 (s, 9H).

Intermediate I.1.c.1 (Scheme 1.1)

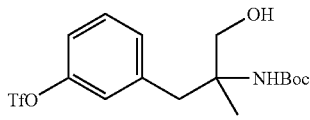

To a solution of intermediate I.1.b.1 (1.00 g, 2.27 mmol) in 20 mL anhydrous THF cooled to 0° C. under an atmosphere of argon was added lithium borohydride (0.236 mL, 0.473 mmol, 2.0M solution in THF). After warming to rt over 2 hr., the reaction was cooled back down to 0° C. and quenched with MeOH. It was diluted with water (50 mL) and extracted with EtOAc (2×50 µL). The organic layers were combined, washed with brine (2×50 mL), dried over sodium sulfate, and concentrated in vacuo. Purification by flash chromatography (90 g silica, 0-45% EtOAc in hexanes) gave intermediate I.1.c.1 as a white solid. ¹H NMR (400 MHz, CDCl₃) δ 7.38 (app t, J=7.9 Hz, 1H), 7.23 (d, J=7.9 Hz, 1H), 7.18-7.15 (m, 1H), 7.12 (s, 1H), 4.46 (s, 1H), 4.06 (br s, 1H), 3.72 (A of ABX, dd, JAB=11.5 Hz, JAX=3.9 Hz, 1H), 3.63 (B of ABX, dd, JAB=11.5 Hz, JBX=8.4 Hz, 1H), 3.30 (A of AB, d, J=13.5 Hz, 1H), 2.89 (B of AB, d, J=13.5 Hz, 1H), 1.48 (s, 9H), 1.03 (s, 3H).

Intermediate I.1.b.2 (Scheme 1.1)

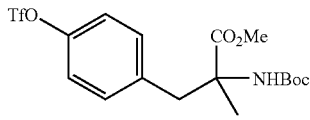

Prepared from alphamethyl p-tyrosine methyl ester using a similar procedure as described for the preparation of intermediate I.1.b.1 ¹H NMR (400 MHz, CDCl₃) δ 7.08 (s, 4H), 5.17 (br s, 1H), 3.64 (s, 3H), 3.35 (A of AB, br d, J=13.4 Hz, 1H), 3.20 (B of AB, d, J=13.4 Hz, 1H), 1.43 (s, 3H), 1.38 (s, 9H).

Intermediate I.1.b.3 (Scheme 1.1)

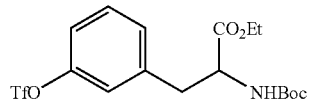

Prepared from m-tyrosine methyl ester using a similar procedure as described for the preparation of intermediate I.1.b.1. ¹H NMR (400 MHz, CDCl₃) δ 7.38 (app. t, J=8.0 Hz, 1H), 7.21-7.14 (m, 2H), 7.06 (s, 1H), 5.04 (d, J=7.2 Hz, 1H), 4.62-4.54 (m, 1H), 4.23-4.10 (m, 2H), 3.19 (A of ABX, dd, JAB=13.7 Hz, JAX=5.8 Hz, 1H), 3.10 (B of ABX, dd, JAB=13.7 Hz, JBX=5.8 Hz, 1H), 1.43 (s, 9H), 1.24 (t, J=7.1 Hz, 3H).

Intermediate I.1.c.1 (Scheme 1.1)

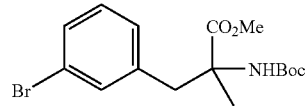

To a solution of methyl N-(diphenylmethylene)alaninate (2.6 g, 9.7 mmol) in DMF (20 mL) cooled to 0° C. was added NaHMDS (12.2 mL, 12.2 mmol, 1M in THF) slowly via syringe and the reaction mixture was stirred at 0° C. for 15 min at which point 3-bromo-benzyl bromide (2.55 g, 10.2 mmol) in DMF (10 mL) was added slowly via syringe. The reaction mixture was allowed to warm to rt over 16 h, quenched with aq NH₄Cl and water, extracted with EtOAc, washed with aq LiCl (×3), dried over Na₂SO₄, concentrated in vacuo, and purified by flash chromatography (120 g silica, 0-15% EtOAc in hexanes) to provide methyl 3-bromo-N-(diphenylmethylene)-α-methylphenylalaninate.

To a solution of methyl 3-bromo-N-(diphenylmethylene)-α-methylphenylalaninate (2.95 g, 6.76 mmol) in MeOH (25 mL) and THF (25 mL) was added 6N HCl (3.4 mL, 20.3 mmol) and the reaction mixture was stirred at RT for 5 min, concentrated in vacuo and purified by ion exchange chromatography (SCX, 25 g, then 50 g, MeOH then 2M NH₃ in MeOH) to provide methyl 3-bromo-α-methylphenylalaninate.

To a solution of methyl 3-bromo-α-methylphenylalaninate (1.67 g, 6.1 mmol) in THF (30 mL) and MeOH (5 mL) was added ditertbutyldicarbonate (1.61 g, 7.4 mmol) and the reaction mixture was stirred at 50° C. for 6 h and at rt for 16 h, concentrated in vacuo, and purified by flash chromatography (90 g silica, 0-20% EtOAc in hexanes) to provide Intermediate I.1.c.1. ¹H NMR (400 MHz, CDCl₃) δ 7.36 (d, J=7.6 Hz, 1H), 7.24 (s, 1H), 7.13 (t, J=7.6 Hz, 1H), 6.98 (d, J=7.6 Hz, 1H), 5.16 (br s, 1H), 3.77 (s, 3H), 3.39 (A of AB, br d, J=13.5 Hz, 1H), 3.19 (B of AB, d, J=13.5 Hz, 1H), 1.56 (br s, 3H), 1.49 (s, 9H).

Intermediate I.1.c.2 (Scheme 1.1)

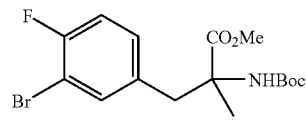

Prepared from methyl N-(diphenylmethylene)alaninate and 3-bromo-4-fluoro-benzyl bromide as described for the preparation of Intermediate I.1.c.1. MS M+1=390.

Intermediate I.1.c.3 (Scheme 1.1)

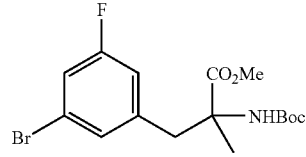

Prepared from methyl N-(diphenylmethylene)alaninate and 3-bromo-5-fluoro-benzyl bromide as described for the preparation of Intermediate I.1.c.1. MS M+1=390.

Intermediate I.1.c.4 (Scheme 1.1)

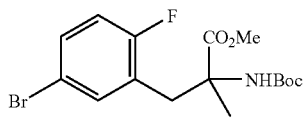

Prepared from methyl N-(diphenylmethylene)alaninate and 5-bromo-2-fluoro-benzyl bromide as described for the preparation of Intermediate I.1.c.1. MS M+1=390.

Intermediate I.1.c.5 (Scheme 1.1)

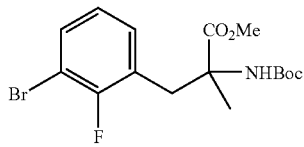

Prepared from methyl N-(diphenylmethylene)alaninate and 3-bromo-2-fluoro-benzyl bromide as described for the preparation of Intermediate I.1.c.1. MS M+1=390.

Intermediate II.1.a.1 (Scheme 2.1)

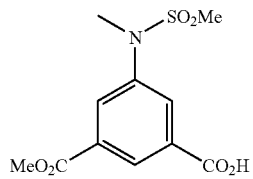

Step A: Sulfonylation

To a stirred slurry of dimethyl 5-aminoisophthalate (5.0 g, 23.90 mmol) in 100 mL $CH_2Cl_2$/pyridine (3:1) at 0° C. was added methanesulfonyl chloride (1.85 mL, 23.90 mmol). The resulting mixture was stirred for 4 h at rt. The solvent was removed in vacuo and ethyl acetate (100 mL) was added resulting in precipitate formation. The product was collected by filtration to give the sulfonamide as a white solid. $^1$H NMR (400 MHz, $DMSO_{d6}$) δ 8.15 (s, 1H), 8.02 (s, 2H), 3.89 (s, 6H), 3.02 (s, 3H) LCMS $[M-OCH_3]^+$=256.16.

Step B: Methylation

To a solution of sodium hydride (0.153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with $H_2O$ (100 mL) and extracted with EtOAc (3×50 mL). The organic extracts were dried over $MgSO_4$ and evaporated to give the product. $^1$H NMR (400 MHz, $DMSO_{d6}$) δ 8.40 (s, 1H), 8.19 (s, 2H), 3.91 (s, 6H), 3.34 (s, 3H), 3.01 (s, 3H). LCMS [M+H]=302.15.

Step C: Hydrolysis

Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to rt over 8 h. The solution was acidified with 1N HCl (30 μL) and extracted with EtOAc (3×50 mL). The combined organic extracts were washed with brine and dried over $MgSO_4$, filtered and concentrated in vacuo. Purification by silica gel chromatography (5% MeOH/$CHCl_3$ containing 1% HOAc) gave the mono acid. $^1$H NMR (400 MHz, $DMSO_{d6}$) δ 8.30 (s, 1H), 8.10 (s, 2H), 3.84 (s, 3H), 3.27 (s, 3H), 2.94 (s, 3H). LCMS (M+H)=288.16.

Intermediate II.1.a.2 (Scheme 2.1)

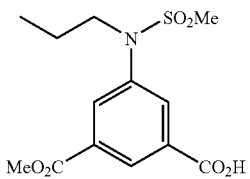

Prepared as described for the preparation of intermediate II.1.a.1 with the use of n-propyl iodide instead of methyl iodide in step B. $^1$H NMR (400 MHz, $DMSO_{d6}$) δ 13.58 (s, 1H), 8.42 (s, 1H), 8.16-8.11 (m, 2H), 3.91 (s, 3H), 3.69 (t, J=7.0 Hz, 2H), 3.02 (s, 3H), 1.40-1.30 (m, 2H), 0.83 (t, J=7.3 Hz, 3H).

Intermediate II.1.c.1 (Scheme 2.1)

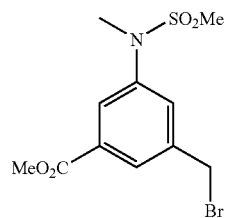

Step A: Borane Reduction

To a solution of intermediate II.1.a.1 (1.00 g, 3.48 mmol) in 30 mL anhydrous THF cooled to 0° C. under an atmosphere of argon was added borane-tetrahydrofuran complex (17.40 mL, 17.40 mmol, 1.0M solution in THF) slowly via syringe. After warming to rt slowly over 15 hr, the reaction was cooled back down to 0° C. and quenched with MeOH. After warming to rt, it was concentrated to half its original volume, diluted with water, and extracted with EtOAc (2×50 mL). The organic extracts were combined, washed with bicarb and brine, dried over $Na_2SO_4$ and evaporated to give methyl 3-(hydroxymethyl)-5-[methyl(methylsulfonyl)amino]benzoate as a white solid.

Step B: Bromination

To a solution of alcohol (0.710 g, 2.60 mmol) from Step A and carbon tetrabromide (1.12 g, 3.38 mmol) in 25 mL anhydrous $CH_2Cl_2$ under an atmosphere of argon was added a solution of triphenylphosphine (0.818 g, 3.12 mmol) in 5 mL anhydrous $CH_2Cl_2$ slowly via syringe. After 2 hr, additional carbon tetrabromide (0.224 g, 0.675 mmol) and triphenylphosphine (0.164 g, 0.623 mmol) were added. After an additional 1 hr, it was concentrated in vacuo. Purification by silica gel chromatography (90 g silica, 0-45% EtOAc in hexanes) gave the bromide, Intermediate II.1.c.1, as a white solid. $^1$H NMR (400 MHz, $CDCl_3$) δ 8.00 (s, 1H), 7.92 (s, 1H), 7.67 (s, 1H), 4.50 (s, 2H), 3.94 (s, 3H), 3.37 (s, 3H), 2.87 (s, 3H).

Intermediate II.1.c.2 (Scheme 2.1)

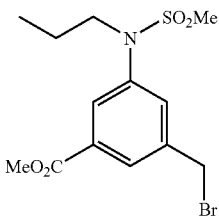

Prepared from intermediate II.1.a.2 using a similar procedure as described for the preparation of intermediate II.1.c.1. $^1$H NMR (400 MHz, CDCl$_3$) δ 8.04 (s, 1H), 7.91 (s, 1H), 7.61 (s, 1H), 4.50 (s, 2H), 3.94 (s, 3H), 3.67 (t, J=7.2 Hz, 2H), 2.90 (s, 3H), 1.56-1.46 (m, 2H), 0.92 (t, J=7.3 Hz, 3H).

Intermediate II.1.c.3 (Scheme 2.1)

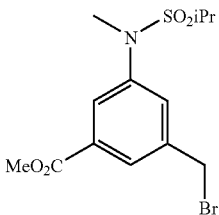

Prepared as described for the preparation of intermediate II.1.a.1 with the use of isopropyl sulfonyl chloride instead of mesyl chloride in step A. $^1$H NMR (400 MHz, CDCl$_3$) δ 8.00-7.90 (m, 2H), 7.71 (t, J=1.8 Hz, 1H), 4.50 (s, 2H), 3.94 (s, 3H), 3.41 (s, 3H), 3.38-3.26 (m, 1H), 1.37 (d, J=6.8 Hz, 6H).

Intermediate II.1.e.1 (Scheme 2.1)

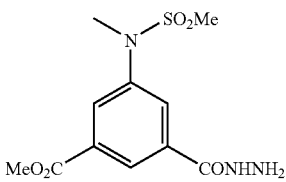

Step A: Coupling

To a solution of intermediate II.1.a.1 (0.520 g, 1.810 mmol) and Boc-hydrazine (0.359 g, 2.715 mmol) in 8 mL CH$_2$Cl$_2$ was added Hunig's base (0.950 mL, 5.43 mmol) and BOP-reagent (0.881 g, 1.991 mmol). After 30 min, the reaction was poured onto a silica gel column and purified by normal phase chromatography (5->75% EtOAc/hexanes) to afford the desired product as a white foam.

Step B: Boc Deprotection

Gaseous HCl was bubbled through a solution of product from Step A in 20 mL CH$_2$Cl$_2$ at 0° C. for 5 min. The reaction was warmed to rt for 20 min, then concentrated to afford intermediate II.1.e.1 as a white solid. $^1$H NMR (100 MHz, CD$_3$OD) δ 8.42 (m, 1H), 8.29 (m, 1H), 8.17 (m, 1H), 3.95 (s, 3H), 3.38 (s, 3H), 2.95 (s, 3H).

Intermediate II.2.c.1 (Scheme 2.2)

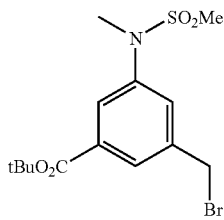

Prepared from intermediate II.a.1 using a similar procedure as described for the preparation of intermediate II.2.c.2. $^1$H NMR (400 MHz, CDCl$_3$) δ 7.91 (br s, 1H), 7.86 (br s, 1H), 7.64 (br s, 1H), 4.50 (s, 2H), 3.35 (s, 3H), 2.87 (s, 3H), 1.61 (s, 9H).

Intermediate II.2.c.2 (Scheme 2.2)

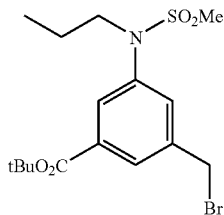

Step A: tBu Ester Installment

To a solution of intermediate II.1.a.2 (3 g, 9.5 mmol) in DMF (50 mL) was added carbonyl diimidazole (1.78 g, 10.97 mmol) and the reaction mixture was stirred at 50° C. for 30 min. DBU (1.64 mL, 10.9 mmol) and tBuOH (2 mL, 20.9 mmol) were added and the reaction mixture was stirred at 50° C. for 5 h 30 and at RT for 16 h. The reaction mixture was diluted with EtOAc, washed with water, with 10% KHSO$_4$, with aq NaHCO$_3$ with aq LiCl (×3), dried over Na$_2$SO$_4$, and concentrated in vacuo to provide the Me-tBu diester.

Step B: Me Ester Hydrolysis

To a solution of the previous Me-tBu diester (3.3 g, 8.9 mmol) in MeOH (40 mL) and THF (40 mL) was added 1N NaOH (8.9 mL, 8.9 mmol) and the reaction mixture was stirred at RT for 16 h. 1N HCl (9 mL, 9 mmol) was added, the reaction mixture was extracted with DCM, dried over Na$_2$SO$_4$, concentrated in vacuo, and purified by flash chromatography (120 g silica, 50-100% (0.5% HOAc in EtOAc) in hexanes) to provide the corresponding tBu ester-carboxylic acid.

Step C: Borane Reduction

Performed as described in the preparation of intermediate II.1.c.1

Step D: Bromination

Performed as described in the preparation of intermediate II.1.c.1 to provide intermediate II.2.c.2. $^1$H NMR (400 MHz, CDCl$_3$) δ 7.95 (br s, 1H), 7.85 (br s, 1H), 7.56 (br s, 1H), 4.50 (s, 2H), 3.66 (t, J=7.1 Hz, 2H), 2.90 (s, 3H), 1.61 (s, 9H), 1.58-1.44 (m, 2H), 0.92 (t, J=7.3 Hz, 3H).

Intermediate II.2.c.3 (Scheme 2.2)

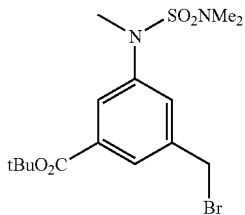

Step A: Cbz Protection

To a solution of dimethylisopthalate (3.00 g, 14.3 mmol) in 75 mL 1,2-dichloroethane and 20 mL water was added $K_2CO_3$ (4.95 g, 35.9 mmol), followed by Cbz-Cl (2.69 g, 15.8 mmol). After 6 h, the reaction was concentrated then diluted with EtOAc and water until the layers were homogeneous. The layers were separated, and the organics were washed with 0.5M $KHSO_4$ (2×) and brine. Dried over $Na_2SO_4$, filtered and concentrated. Used product without further purification. LC/MS (M+H)=344.

Step B: Methylation

To a solution of product from Step A (2.71 g, 7.89 mmol) in 20 mL DMF was added $CS_2CO_3$ (5.14 g, 15.78 mmol), followed by MeI (0.98 mL, 15.78 mmol). The reaction was allowed to proceed at room temperature for 16 h, then diluted with EtOAc and 3M LiCl. The layers were separated, and the organics were washed with 3M LiCl (2×) and brine, dried over $Na_2SO_4$, filtered and concentrated. The residue was purified using normal phase silica gel chromatography (10->60% EtOAc/hex) to afford the desired methylation product. LC/MS (M+H)=358.

Step C: Monhydrolysis

Performed using a procedure as described in Step C of Intermediate II.1.a.1 synthesis. LC/MS (M+H)=344

Step D: t-Bu Ester Installation

Performed using a procedure as described in Step A of Intermediate II.2.c.2 synthesis. LC/MS (M-t-Bu+H)=344

Step E: Cbz Hydrogenolysis

To a solution of Cbz aniline (1.38 g, 3.45 mmol) in 15 mL EtOAc was added 10% Pd/C (0.368 g, 0.345 mmol). The vessel was evacuated/opened to $H_2$ (3×), then stirred over an atmosphere of $H_2$ (from balloon) for 4.5 h. The flask was evacuated/opened to Ar (3×), and the reaction was filtered through a pad of celite, rinsing with fresh EtOAc. The organics were concentrated, and used without further purification. LC/MS (M+$CH_3$CN)=307

Step F: Sulfonylation

To a solution of aniline from Step E (0.360 g, 1.357 mmol) in 5 mL $CH_2Cl_2$ was added pyridine (0.55 mL, 6.78 mmol), followed by dimethylsulfamoyl chloride (0.290 mL, 2.71 mmol) The reaction was heated at 45° C. for 72 h, then further aliquots of pyridine (0.55 mL, 6.78 mmol) and dimethylsulfamoyl chloride (0.290 mL, 2.71 mmol) were added, and the reaction was heated for a further 24 h. The reaction was cooled to RT and quenched by the addition of satd. $NaHCO_3$ and EtOAc. The layers were separated, and the organics were washed with 0.5M $KHSO_4$ (2×) and brine, dried over $Na_2SO_4$, filtered and concentrated. The residue was purified by normal phase silica gel chromatography (5->45% EtOAc/hex) to afford the desired product. LC/MS (M+H)=373.

Step G: Lithium Borohydride Reduction

To a solution of material from Step F (0.235 g, 0.632 mmol) in 1.8 mL THF at RT was added 2.0M $LiBH_4$ (1.25 mL, 2.50 mmol), and the reaction was allowed to proceed overnight. The reaction was cooled to 0° C., quenched with satd. $NaHCO_3$ and dilute with EtOAc. The layers were separated, the organics were washed with brine, dried over $Na_2SO_4$, filtered and concentrated. The residue was purified by normal phase silica gel chromatography (20->85% EtOAc/hex) to afford the desired product. LC/MS (M+H)=345.

Step H: Bromination

Performed as described in the preparation of intermediate II.1.c.1 to provide intermediate II.2.c.3. LC/MS (M+H)=407, 409 (Br pattern)

Intermediate II.2.c.4 (Scheme 2.2)

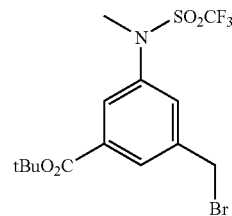

Step A: Sulfonylation

To a solution of dimethyl amino isophthalate (0.500 g, 2.39 mmol) in 12 mL $CH_2Cl_2$ at 0° C. was added diisopropylethylamine (2.1 mL, 11.95 mmol) and triflic anhydride (1.0 mL, 5.97 mmol). The reaction was allowed to warm to RT over 20 h, then quenched by adding 0.5M $KHSO_4$ and diluted with EtOAc. The layers were separated, the organics were washed with 0.5M $KHSO_4$ and brine, dried over $Na_2SO_4$, filtered and concentrated. The residue was purified by preparative HPLC to afford the desired product. LC/MS (M+H)=342.

Step B-Step H: methylation, monhydrolysis, t-Bu ester installation, lithium borohydride reduction, bromination: Performed as described in the synthesis of Intermediate II.2.c.3. LC/MS for title compound Intermediate II.2.c.4 (M+H)=432, 434 (Br pattern).

Intermediate II.2.c.5 (Scheme 2.2)

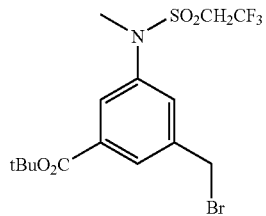

Prepared from 2,2,2-trifluoroethanesulfonyl chloride and dimethyl aminoisophthalate using a similar procedure as described for the preparation of intermediate II.2.c.3. LC/MS (M+H)=446.

Intermediate II.2.c.6 (Scheme 2.2)

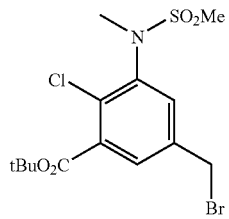

Step A: Iodination

To a solution of 2-chloro-3-nitro-benzoic acid (10 g, 49.6 mmol) in triflic acid (45 mL) cooled to 0° C. was added N-iodosuccinimide (12.3 g, 54.6 mmol) by portions. The reaction mixture was stirred at 40° C. for 4 h, additional N-iodosuccinimide (1.2 g) was added and the reaction mixture was stirred at 40° C. for 16 h. Ice was slowly added to the reaction mixture and the resulting mixture was poured on ice and water. The precipitated solid was filtered, washed with water, taken in EtOAc, washed with aqueous $NaHSO_3$/$KHSO_4$, with water, with brine, dried over sodium sulfate, and concentrated in vacuo to give a 1:3 mixture of 2-chloro-3-nitro-5-iodo-benzoic acid and 2-chloro-3-nitro-benzoic acid.

Step B: Esterification

The mixture from step A was taken in HCl(g) saturated MeOH and stirred at 60° C. for 4 h. Concentration in vacuo and purification by flash chromatography (300 g silica gel, 0 to 25% EtOAc in hexane) yielded methyl 2-chloro-5-iodo-3-nitrobenzoate as a white solid. $^1$H NMR (400 MHz, $CDCl_3$) δ 8.24 (d, J=2 Hz, 1H), 8.11 (d, J=2 Hz, 1H), 3.98 (s, 3H).

Step C: Allylation

A solution of methyl 2-chloro-5-iodo-3-nitrobenzoate (3 g, 8.8 mmol) and vinyl tributyltin (3.6 g, 11.4 mmol) in DMF (50 mL) was degassed with argon. $PdCl_2$/$(PPh_3)_2$ (308 mg, 0.44 mmol) was added, the reaction vessel was sealed under argon and the reaction mixture was stirred at 90° C. for 16 h. The reaction mixture was cooled to RT and treated with aqueous KF (1.5 g in 20 mL water) for 2 h30. The mixture was diluted with water and EtOAc filtered on cellite. The organic layer was separated, washed with aq LiCl (×3), dried over sodium sulfate, concentrated in vacuo and purified by flash chromatography (120 g silica gel, 0 to 20% EtOAc in hexane) to give methyl 2-chloro-3-nitro-5-vinylbenzoate as a pale yellow solid. $^1$H NMR (400 MHz, $CDCl_3$) δ 7.94 (d, J=2 Hz, 1H), 7.83 (d, J=2 Hz, 1H), 6.69 (dd, J=17.4 Hz, 10.8 Hz, 1H), 5.89 (d, J=17.4 Hz, 1H), 5.52 (d, J=10.8 Hz, 1H), 3.99 (s, 3H).

Step D: Nitro Reduction

A solution of methyl 2-chloro-3-nitro-5-vinylbenzoate (1.75 g, 7.2 mmol) and $SnCl_2$ (4.1 g, 18.1 mmol) in EtOH (50 mL) was stirred at 75° C. for 16 h. The reaction mixture was cooled to RT, diluted with water and EtOAc, stirred at RT for 10 min, and filtered on cellite. The organic layer was separated, washed with brine, dried over sodium sulfate, concentrated in vacuo and purified by flash chromatography (120 g silica gel, 0 to 25% EtOAc in hexane) to give methyl 2-chloro-3-amino-5-vinylbenzoate as a yellow oil. MS M+1=212.

Step E: Mesylation

As described in the preparation of intermediate II.1.a.1, step A.

Step F: Methylation

As described in the preparation of intermediate II.a.1, step B.

Step G: Hydrolysis

As described in the preparation of intermediate II.2.c.2, step B.

Step H: tBu Ester Installation

As described in the preparation of intermediate II.2.c.2, step A, to give tert-butyl 2-chloro-3-[methyl(methylsulfonyl)amino]-5-vinylbenzoate. $^1$H NMR (400 MHz, $CDCl_3$) δ 7.67 (d, J=2 Hz, 1H), 7.60 (d, J=2 Hz, 1H), 6.65 (dd, J=17.6 Hz, 10.9 Hz, 1H), 5.81 (d, J=17.6 Hz, 1H), 5.39 (d, J=10.9 Hz, 1H), 3.30 (s, 3H), 3.05 (s, 3H) 1.62 (s, 9H).

Step I: Reductive Ozonolysis

Through a solution of tert-butyl 2-chloro-3-[methyl(methylsulfonyl)amino]-5-vinylbenzoate (700 mg, 2 mmol) in DCM (7 mL) and MeOH (3 mL) cooled to −78° C. was bubbled ozone until the solution remained blue. After 5 min stirring at −78° C., MeOH (4 mL) and $NaBH_4$ (115 mg, 3 mmol) were added and the reaction mixture was allowed to warm to RT. The reaction mixture was diluted with EtOAc, washed with 10% $KHSO_4$, brine, dried over sodium sulfate and concentrated in vacuo to provide tert-butyl 2-chloro-5-hydroxymethyl)-3-[methyl(methylsulfonyl)amino]benzoate, used crude in the bromination step.

Step J: Bromination

As described in the preparation of intermediate II.1.c.1, step B, to provide tert-butyl 5-(bromomethyl)-2-chloro-3-[methyl(methylsulfonyl)amino]benzoate. $^1$H NMR (400 MHz, $CDCl_3$) δ 7.69 (d, J=2 Hz, 1H), 7.61 (d, J=2 Hz, 1H), 4.40 (s, 2H), 3.30 (s, 3H), 3.05 (s, 3H).

Intermediate II.2.g.1 (Scheme 2.2)

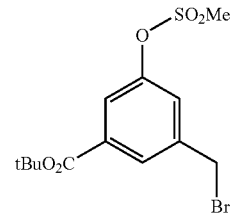

Step A: Sulfonylation

To a 0° C. solution of dimethyl 5-hydroxyisophthalate (2.0 g, 9.5 mmol) in 3:1 dichloromethane:pyridine (100 mL) was added methanesulfonyl chloride (3.6 g, 31.4 mmol). The reaction warmed to room temperature over 18 h. The reaction mixture was concentrated in vacuo. The crude material was diluted with DCM and washed with 1N HCl, $H_2O$ (2×), brine, dried with $MgSO_4$, filtered, concentrated and purified by flash chromatography (40 g silica, 25-40% EtOAc/hexanes) to give 1.37 g (50%) of dimethyl 5-[(methylsulfonyl)oxy]isophthalate. $^1$H NMR (400 MHz, $CDCl_3$) δ 8.66 (s, 1H), 8.12 (s, 2H), 3.97 (s, 6H), 3.23 (s, 3H).

Step B: Monohydrolysis

To a 0° C. solution of dimethyl 5-[(methylsulfonyl)oxy]isophthalate (1.37 g, 4.75 mmol) in THF (150 mL) was added 0.1 N NaOH solution (46.6 mL, 4.66 mmol) dropwise in an addition funnel. Reaction stirred at 0° C. for 2 hours and then warmed to room temperature. Reaction was concentrated in vacuo. Crude material was acidified with 1N HCl and extracted with EtOAc (3×). The combined organics were dried with $MgSO_4$, filtered, concentrated and purified by flash chromatography (40 g silica, 0-5% MeOH/DCM/1% acetic acid) to give 0.74 g (57%) of 3-(methoxycarbonyl)-5-[(methylsulfonyl)oxy]benzoic acid. $^1$H NMR (400 MHz, CDCl$_3$) δ 8.72 (m, 1H), 8.18 (m, 2H), 3.98 (s, 3H), 3.25 (s, 3H).

Step C: Tert-Butyl Installment

To a solution of 3-(methoxycarbonyl)-5-[(methylsulfonyl) oxy]benzoic acid (0.74 g, 2.7 mmol) in DCM (25 mL) was added dimethylaminopyridine (0.165 g, 1.35 mmol) and tert-butanol (0.226 g, 3.05 mmol). The reaction mixture was cooled to 0° C. To the reaction was added EDC (0.569 g, 2.97 mmol). The reaction stirred at 0° C. for 2 h and then warmed to room temp over 16 h. The reaction mixture was washed with 1N HCl, H$_2$O, dried with MgSO$_4$, filtered, concentrated and purified by flash chromatography (25 g silica, 10-30% EtOAc/hexanes) to give 0.74 g (83%) of tert-butyl methyl 5-[(methylsulfonyl)oxy]isophthalate. $^1$H NMR (400 MHz, CDCl$_3$) δ 8.58 (m, 1H), 8.09 (m, 1H), 8.05 (m, 1H), 3.96 (s, 3H), 3.23 (s, 3H) 1.61 (s, 9H).

Step D: Lithium Borohydride Reduction

To a 0° C. solution of tert-butyl 3-(hydroxymethyl)-5-[(methylsulfonyl)oxy]benzoate (0.330 g, 0.99 mmol) in THF (15 mL) was added 2 M lithium borohydride solution (0.524 mL, 1.05 mmol). After 1 hour, added 2 more equivalents LiBH$_4$ solution and warmed reaction to room temp over 18 h. Quenched reaction dropwise with MeOH and then concentrated reaction mixture in vacuo. The crude material was diluted with EtOAc and washed with sat. NaHCO$_3$ solution (2×), H$_2$O, dried with MgSO$_4$, filtered, concentrated and purified by flash chromatography (25 g silica, 30-50% EtOAc/hexanes) to give 0.22 g (73%) of tert-butyl 3-(hydroxymethyl)-5-[(methylsulfonyl)oxy]benzoate. $^1$H NMR (400 MHz, CDCl$_3$) δ 7.93 (s, 1H), 7.76 (s, 1H), 7.51 (s, 1H), 4.78 (s, 2H), 3.19 (s, 3H), 1.60 (s, 9H).

Step E: Bromination

To a solution of tert-butyl 3-(hydroxymethyl)-5-[(methylsulfonyl)oxy]benzoate (0.284 g, 0.939 mmol) in DCM (5 mL) was added triphenylphosphine (0.370 g, 1.41 mmol) and carbon tetrabromide (0.467 g, 1.41 mmol). After 2 hours, reaction mixture was concentrated in vacuo and purified by flash chromatography (25 g silica, 0-20% EtOAc/hexanes) to give 0.21 g (61%) of tert-butyl 3-(bromomethyl)-5-[(methylsulfonyl)oxy]benzoate. $^1$H NMR (400 MHz, CDCl$_3$) δ 7.96 (s, 1H), 7.78 (s, 1H), 7.51 (s, 1H), 4.50 (s, 2H), 3.20 (s, 3H), 1.60 (s, 9H).

Intermediate II.2.g.2 (Scheme 2.2)

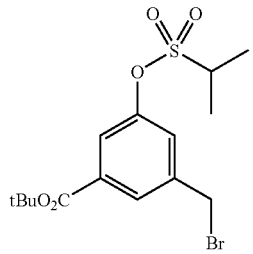

Prepared from dimethyl 5-hydroxyisophthalate and isopropylsulfonyl chloride as described in the preparation of intermediate II.2.g.1.

Intermediate II.2.g.3 (Scheme 2.2)

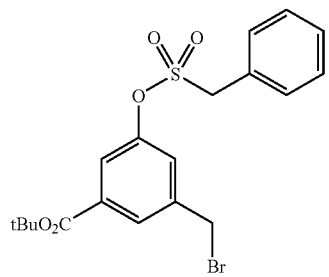

Prepared from dimethyl 5-hydroxyisophthalate and benzylsulfonyl chloride as described in the preparation of intermediate II.2.g.1.

Intermediate II.2.g.4 (Scheme 2.2)

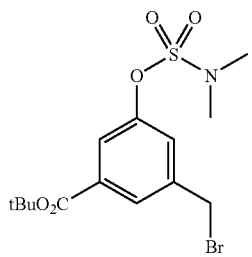

Prepared from dimethyl 5-hydroxyisophthalate and dimethylsulfamoyl chloride as described in the preparation of intermediate II.2.g.1.

Intermediate II.3.c (Scheme 2.3)

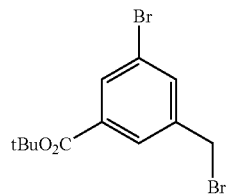

Step A: Bis Hydrolysis

To a solution of dimethyl 5-bromoisophthalate (10 g, 36.6 mmol) in MeOH (200 mL) and THF (200 mL) was added 1N NaOH (91.5 mL, 91.5 mmol) and the reaction mixture was stirred at rt for 5 h, quenched with 1N HCl (92 mL), concentrated in vacuo to ca. 250 mL. The white solid was filtered, washed with water and dried over P$_2$O$_5$, under high vacuum, at 50° C.

Step B: Mono tBu Esterification

To a solution of the previous diacid (3 g, 12.2 mmol) in DMF (100 mL) was added carbonyl diimidazole (1.98 g, 12.2 mmol) and the reaction mixture was stirred at 50° C. for 85 min. DBU (1.83 mL, 12.2 mmol) and tBuOH (2.3 μL, 24.5 mmol) were added and the reaction mixture was stirred at 50° C. for 16 h. Carbonyl diimidazole (2 g) and 4 A sieves were added and the reaction mixture was stirred at 50° C. for 30 min. DBU (2 mL) and tBuOH (10 mL) were added and the reaction mixture was stirred at 50° C. for 4.5 h. The reaction mixture was diluted with 10% KHSO$_4$, filtered on celite, extracted with EtOAc, washed with aq LiCl (×3), dried over Na$_2$SO$_4$, and concentrated in vacuo to provide the corresponding mono tBu ester.

Step C: Borane Reduction
Performed as described in the preparation of intermediate II.1.c.1

Step D: Bromination
Performed as described in the preparation of intermediate II.1.c.1 to provide intermediate II.3.c. $^1$H NMR (400 MHz, CDCl$_3$) δ 8.03 (br s, 1H), 7.92 (br s, 1H), 7.70 (br s, 1H), 4.44 (s, 2H), 1.60 (s, 9H).

Intermediate II.3.f.1 (Scheme 2.3)

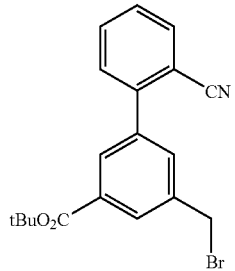

Step A: Pd$^0$ Coupling
To a solution of dimethyl 5-bromo-isophthalate (5.75 g, 21.1 mmol) in THF (50 ml) was added 2-cyanophenylzinc bromide (50.5 ml, 25.3 mmol) followed by tetralis(triphenylphosphine)palladium (0) (0.122 g, 0.105 mmol). The solution was stirred overnight at 50° C. The next day the solution was cooled, filtered, and concentrated in vacuo. Purification by flash chromatography on silica gel (25% EtOAc in Hexanes) afforded 3.8 g'. $^1$H NMR (400 MHz, CDCl$_3$) δ 8.41 (d, J=1.6 Hz, 1H), 7.85-7.80 (m, 1H), 7.74-7.68 (m, 2H), 7.59-7.48 (m, 3H).

Step B-F: hydrolysis, tBu ester installation, Me ester hydrolysis, borane reduction, bromination, as described above. $^1$H NMR (400 MHz, CDCl$_3$) δ 8.07 (d, J=1.6 Hz, 2H), 7.81-7.77 (m, 2H), 7.70-7.67 (m, 1H), 7.57-7.48 (m, 2H).

Intermediate II.3.g.1 (Scheme 2.3)

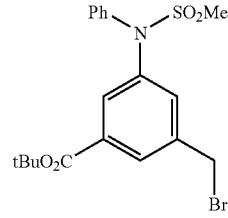

Step A: Pd coupling of Aniline to Tert-Butyl Methyl 5-Bromoisophthalate
To a solution of tert-butyl methyl 5-bromoisophthalate (0.200 g, 0.635 mmol) in 1.2 mL dimethylacetamide was added aniline (0.090 mL, 0.952 mmol) and K$_3$PO$_4$ (0.404 g, 1.90 mmol). The reaction was degassed, and Pd(t-Bu$_3$P)$_2$ (0.032 g, 0.063 mmol) was added. The reaction was heated at 100° C. for 16 h, cooled to RT, quenched by adding H$_2$O and 0.5M KHSO$_4$ and diluted with EtOAc. The layers were separated, and the organics were washed with brine, dried over Na$_2$SO$_4$, filtered and concentrated. The residue was purified by normal phase silica gel chromatography (2->30% EtOAc/hex) to afford the desired product. LC/MS (M+H)=328.

Step B: NaHMDS and MsCl
To a solution of aniline (0.356 g, 1.87 mmol) from Step A in 6 mL DMF at 0° C. was added 1.0M NaHMDS (1.41 mL, 1.41 mmol). After 5 min, MsCl (0.210 mL, 2.79 mmol) was added. After 20 min, the reaction was quenched by adding sat. NH$_4$Cl and H$_2$O, and diluted with EtOAc. The layers were separated, and the organics were washed with brine, dried over Na$_2$SO$_4$, filtered and concentrated. The residue was purified by normal phase silica gel chromatography (2->40% EtOAc/hex) to afford the desired product. LC/MS (M+H)=406.

Steps C and Step D: lithium borohydride reduction and bromination, as described in the preparation of intermediate II.2.g.1. LC/MS for title compound II.3.g.1 (M+H)=440, 442 (Br pattern).

Intermediate II.4.c.1 (Scheme 2.4)

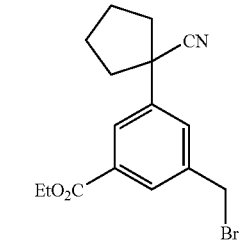

Step A: Bromination
To a solution of diethyl 5-(hydroxymethyl)benzene-1,3-dioate (3.5 g, 0.014 mol) and carbon tetrabromide (5.0 g, 0.015 mol) in 30 mL CH$_2$Cl$_2$, cooled to 0° C., was added dropwise a solution of triphenylphosphine (3.9 g, 0.015 mol) in 20 mL CH$_2$Cl$_2$. The reaction was stirred at 0° C. for 1.5 h, diluted with CHCl$_3$, and washed with water and brine. Drying, solvent evaporation and flash chromatography (silica gel, 0-30% EtOAc/hexanes) gave diethyl-5-(bromomethyl)benzene-1,3-dioate. $^1$H NMR (400 MHz, CDCl$_3$) δ 8.61 (s, 1H), 8.25 (app d, J=1.6 Hz, 2H), 4.55 (s, 2H), 4.42 (q, J=7.1 Hz, 4H), 1.42 (t, J=7.1 Hz, 6H).

Step B: Cyanation
To a solution of diethyl-5-(bromomethyl)benzene-1,3-dioate (1.9 g, 6.0 mmol) in 69 mL MeCN was added trimethylsilyl cyanide (1.2 mL, 9.0 mmol) and tetrabutylammonium fluoride (1M in THF, 9.0 mL, 9.0 mmol). The reaction was stirred for 0.5 h and concentrated. Flash chromatography (silica gel, 0-30% EtOAc/hexanes) gave diethyl 5-(cyanomethyl)benzene-1,3-dioate. $^1$H NMR (400 MHz, CDCl$_3$) δ 8.65 (s, 1H), 8.20 (app t, J=0.7 Hz, 2H), 4.43 (q, J=7.1 Hz, 4H), 3.86 (s, 2H), 1.43 (t, J=7.1 Hz, 6H).

Step C: Alkylation
To a solution of diethyl 5-(cyanomethyl)benzene-1,3-dioate (500 mg, 1.9 mmol) in 18.6 mL THF was added potassium bis(trimethylsilyl)amide (1.1 g, 5.7 mmol) and the reaction was stirred at rt for 5 min. 1,4-Dibromobutane (0.25 mL, 2.1 mmol) was added, the mixture was stirred for 45 min and then quenched with 1N HCl. Ethyl acetate was added, the layers separated and the organic layer was washed with water and brine. Drying, solvent evaporation and flash chromatography (silica gel, 0-15% EtOAc/hexanes) gave diethyl 5-(1-cyanocyclopentyl)benzene-1,3-dioate. $^1$H NMR (400 MHz, CDCl$_3$) δ 8.63 (m, 1H), 8.31 (m, 2H), 4.43 (q, J=7.1 Hz, 4H), 2.56 (m, 2H), 2.14-1.99 (m, 6H), 1.43 (t, J=7.1 Hz, 6H).

Step D: Ester Hydrolysis

A solution of diethyl 5-(1-cyanocyclopentyl)benzene-1,3-dioate (0.33 g, 1.05 mmol) and NaOH (1N in H$_2$O, 0.945 mL, 0.945 mmol) in 5 mL THF and 5 mL EtOH was stirred at rt overnight. The reaction mixture was concentrated, diluted with H$_2$O and extracted with ether. The aqueous phase was made acidic with 1N HCl, extracted with EtOAc and the combined organic layers were washed with brine. Drying and solvent evaporation gave 3-(ethoxycarbonyl)-5-(1-cyanocyclopentyl)benzoic acid. $^1$H NMR (400 MHz, CD$_3$OD) δ 8.58 (m, 1H), 8.35 (m, 2H), 4.43 (q, J=7.1 Hz, 2H), 2.51 (m, 2H), 2.18 (m, 2H), 2.05 (m, 4H), 1.42 (t, J=7.1 Hz, 3H).

Step E: Acid Reduction and Bromination

To a solution of 3-(ethoxycarbonyl)-5-(1-cyanocyclopentyl)benzoic acid (0.4 g, 1.4 mmol) in 14 mL THF, cooled to 0° C., was added borane-tetrahydrofuran complex (1M in THF, 5.6 mL, 5.6 mmol) dropwise. The reaction was stirred at 0° C. for 1.5 h and then at rt for 3.5 h. The mixture was quenched with MeOH, concentrated, diluted with EtOAc and washed with water and brine. Drying and solvent evaporation gave ethyl 3-(1-(aminomethyl)cyclopentyl)-5-(hydroxymethyl)benzoate and ethyl 3-(1-cyanocyclopentyl)-5-(hydroxymethyl)benzoate. The crude mixture was dissolved in 6.6 mL CH$_2$Cl$_2$, cooled to 0° C. and treated with carbon tetrabromide (0.56 g, 1.7 mmol). A solution of triphenylphosphine (0.42 g, 1.6 mmol) in 6.6 mL CH$_2$Cl$_2$ was added and the reaction was stirred at 0° C. for 1 h. Concentration and flash chromatography (silica gel, 0-20% EtOAc/hexanes) gave ethyl 3-(bromomethyl)-5-(1-cyanocyclopentyl)benzoate. $^1$H NMR (400 MHz, CDCl$_3$) δ 8.02 (t, J=1.9 Hz, 2H), 7.70 (t, J=1.7 Hz, 1H), 4.52 (s, 2H), 4.41 (q, J=7.1 Hz, 2H), 2.53 (m, 2H), 2.12-1.97 (m, 6H), 1.41 (t, J=7.1 Hz, 3H).

Intermediate II.5.d.1 (Scheme 2.5)

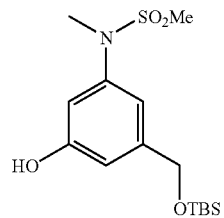

Step A: Bn Ether

To a solution of dimethyl 5-hydroxyisophthalate (20 g, 95.2 mmol) in DMF (200 mL) was added cesium carbonate (18.6 g, 57.1 mmol) and benzyl bromide (11.4 mL, 95.2 mmol) and the reaction mixture was stirred at rt for 24 h. Cesium carbonate (7.8 g) and benzyl bromide (4.6 mL) were added and the reaction mixture was stirred at rt for 24 h. The reaction mixture was diluted with water, the pH was adjusted to pH 7-8 with 1N HCl, the resulting mixture was extracted with EtOAc, washed with aq LiCl (×3), dried over Na$_2$SO$_4$, and concentrated in vacuo to provide the corresponding benzyl ether Step B: Monohydrolysis Monohydrolysis of the previous diester with 1N NaOH in MeOH/THF, according to preparation of intermediate II.1.a.1, step C, followed by purification by flash chromatography (300 g silica, 0-50% (0.5% HOAc in EtOAc) in hexanes) provided the corresponding monoacid.

Step C: Curtius Rearrangement

The previous monoacid (5.98 g, 20.9 mmol), triethyl amine (16.1 mL, 31.3 mmol), and diphenyphosphoryl azide (8.62 g, 31.3 mmol) were dissolved in anhydrous tert-butyl alcohol (200 mL) and allowed to stir under reflux, 110° C., for 16 hours. The crude reaction mixture is then concentrated in vacuo, then diluted with EtOAc and washed with deionized water (×3), brine (×3), dried over sodium sulfate, and concentrated in vacuo. The crude mixture was then purified using flash chromatography (145 g silica, 0-30% EtOAc in hexanes) to afford the corresponding ester carbamate.

Step D: Alkylation and Debocing

The previous ester carbamate (7.3 g, 20.5 mmol) was dissolved in DMF (40 mL) and cooled to 0° C., the 1.0 M solution of NaHMDS (22.5 mL, 22.5 mmol) was then added dropwise via syringe. After stirring 0.5 h at 0° C., the MeI (1.53 mL, 24.5 mmol) was added dropwise via syringe and the reaction was allowed to warm slowly to rt and stir for an additional 16 h. The crude reaction mixture was quenched with deionized water and diluted with DCM. The biphasic system was washed with DI water (×3), brine (×3), dried over sodium sulfate, and concentrated in vacuo. The crude mixture was then purified using flash chromatography (145 g silica, 0-25% EtOAc in hexanes) to afford the corresponding N-methyl carbamate. The N-methyl carbamate (6.5 g, 17.5 mmol) was then dissolved in a 4.0 M of HCl in 1,4-dioxane (43.8 mL, 175 mmol) and allowed to stir at rt for 16 h, the reaction was then concentrated in vacuo to afford to corresponding N-methyl amino ester.

Step E: Sulfonylation

The previous N-methyl amino ester (4.7 g, 17.3 mmol) was dissolved in anhydrous DCM (40 mL) and Hunig's base (10.6 mL, 60.6 mmol) was added via syringe. Methanesulfonyl chloride (1.48 mL, 19.1 mmol) was then added via syringe and the reaction was allowed to stir at rt for 16 h. The crude reaction mixture was then concentrated in vacuo and purified using flash chromatography (145 g silica, 0-35% EtOAc in hexanes) to afford the corresponding N-methyl-N-mesyl ester.

Step F: Ester Reduction and TBS Installation

The previous N-methyl-N-mesyl ester (3.45 g, 9.9 mmol) was place in an oven dried round bottom flask under argon and dissolved in 10 mL anhydrous THF. A 2.0 M solution of lithium borohydride (50.0 mL, 98.7 mmol) was added via syringe and the reaction was raised to 40° C. The reaction was allowed to stir at this temperature for 16 h. Upon completion the crude reaction mixture was quenched with 6 mL methanol, followed by a 10 mL solution 1:1 mixture of acetone and DI water. The mixture was then extracted with EtOAc (×3), dried over sodium sulfate, concentrated in vacuo and purified using flash chromatography (145 g silica, 15-75% EtOAc in hexanes) to afford the corresponding N-methyl-N-mesyl alcohol. The alcohol was then dissolved in anhydrous DCM, followed by the addition of imidazole and tert-butyldimethylsilyl chloride. The reaction was allowed to stir at RT for 16 h. The crude reaction mixture was washed with KHSO$_4$ (×3), NaHCO$_3$ (×3), DI water (×3), brine (×3), concentrated in vacuo and purified using flash chromatography (120 g silica, 0-20% EtOAc in hexanes) to afford the corresponding silyl ether.

Step G: Hydrogenolysis of Bn Ether

The previous silyl ether (3.14 g, 7.2 mmol) was dissolved in 120 mL of degassed EtOAc and placed under argon and Pd/C (0.08 g, 0.73 mmol) was added in one portion. Hydrogen (144 mmol) was added via a three way adaptor and the system was purged under reduced pressure, then exposed to hydrogen. This process of purging and exposure to hydrogen was repeated three times. The reaction was allowed to stir at rt for 16 h. The crude reaction mixture was filtered over celite and washed with EtOAc, dried over sodium sulfate, and concentrated in vacuo. The crude material was purified using flash chromatography (145 g silica, 0-30% EtOAc in hexanes) to afford the corresponding phenol. $^1$H NMR (400 MHz, CDCl$_3$) δ 7.03 (s, 1H), 6.76 (s, 1H), 6.66 (s, 1H), 4.57 (s, 2H), 3.15 (s, 3H), 2.75 (s, 3H), 0.83 (s, 9H), 0.01 (s, 6H).

Intermediate II.5.e.1 (Scheme 2.5)

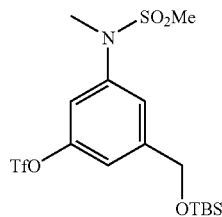

Prepared from intermediate II.5.d.1 using a similar procedure as described in the preparation of intermediate I.1.b.1 $^1$H NMR (400 MHz, CDCl$_3$) δ 7.26 (s, 1H), 7.10 (s, 1H), 7.05 (s, 1H), 4.66 (s, 2H), 3.23 (s, 3H), 2.74 (s, 3H), 0.82 (s, 9H), 0.02 (s, 6H).

Intermediate III.1.c.1 (Scheme 3.1)

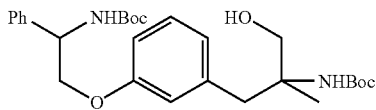

Step A: Allylation

To a solution of intermediate I.1.a.1 (0.050 g, 0.162 mmol) and 2-bromoacetophenone (0.032 g, 0.162 mmol) in 1 mL anhydrous DMF under an atmosphere of argon was added Cs$_2$CO$_3$ (0.029 g, 0.089 mmol). After 24 hr, the crude reaction mixture was purified by reverse phase preparative HPLC (5->95% CH$_3$CN/H$_2$O, 0.1% added TFA, C18 PRO YMC 20×150 mm) to afford methyl N-(tert-butoxycarbonyl)-alpha-methyl-3-(2-oxo-2-phenylethoxy)phenylalaninate as a pale yellow oil.

Step B: Reductive Amination

To a solution of methyl N-(tert-butoxycarbonyl)-alpha-methyl-3-(2-oxo-2-phenylethoxy)phenylalaninate (0.600 g, 1.40 mmol), 4 Å sieves (spatula tip), acetic acid (0.089 mL, 1.54 mmol), and benzylamine (0.184 mL, 1.68 mmol) in 10.0 mL dichloroethane was added sodium triacetoxyborohydride (0.357 g, 1.68 mmol). After 16 hr, additional benzylamine (0.092 mL, 0.840 mmol), sodium triacetoxyborohydride (0.178 g, 0.840 mmol), and acetic acid (0.045 mL, 0.770 mmol) were added. After an additional 16 hr, the temperature was raised to 50° C. for 30 hr., and additional amounts of 4 Å sieves, acetic acid, benzylamine, and sodium triacetoxyborohydride were added over 72 hr to achieve full conversion. The reaction was quenched with bicarb. and filtered, washing with water and EtOAc. The layers of the filtrate were separated, and the aqueous layer was back extracted with EtOAc. The organic layers were combined, washed with bicarb. and brine (×2), dried over sodium sulfate, and concentrated in vacuo. Purification by flash chromatography (90 g silica, 0-30% EtOAc in hexanes) gave methyl 3-[2-(benzylamino)-2-phenylethoxy]-N-(tert-butoxycarbonyl)-alpha-methylphenylalaninate as a yellow foam.

Step C: Hydrogenolysis

To a degassed solution of methyl 3-[2-(benzylamino)-2-phenylethoxy]-N-(tert-butoxycarbonyl)-alpha-methylphenylalaninate (0.457 g, 0.881 mmol) in 10 mL EtOAc was added palladium hydroxide (0.198 g, 1.41 mmol). The resulting mixture was hydrogenated under 1 atm at rt. After 60 hr., the reaction mixture was filtered over celite and concentrated in vacuo to give the corresponding amine as a yellow foam.

Step D: Boc Protection

To a solution of amine (0.371 g, 0.866 mmol) from Step C in 5.0 mL tetrahydrofuran was added di(tert-butyl) dicarbonate (0.227 g, 1.04 mmol). After 16 hr, it was concentrated in vacuo and purified by flash chromatography (40 g silica, 0-25% EtOAc in hexanes) to afford methyl N-(tert-butoxycarbonyl)-3-{2-[(tert-butoxycarbonyl)amino]-2-phenylethoxy}-alpha-methylphenylalaninate as a peach foam.

Step E: Ester Reduction

To a solution of methyl N-(tert-butoxycarbonyl)-3-{2-[(tert-butoxycarbonyl)amino]-2-phenylethoxy}-alpha-methylphenylalaninate (0.050 g, 0.095 mmol) in 0.500 mL anhydrous tetrahydrofuran under an atmosphere of argon was added lithium borohydride (0.236 mL, 0.473 mmol, 2.0M solution in THF). After 3 hr., the reaction was quenched with MeOH and concentrated in vacuo. Purification by flash chromatography (20 g silica, 0-40% EtOAc in hexanes) gave intermediate III.1.c.1 as a colorless oil. $^1$H NMR (two diastereomers) (400 MHz, CDCl$_3$) δ 7.40-7.32 (m, 8H), 7.31-7.24 (m, 2H), 7.19 (app. t, J=7.8 Hz, 2H), 6.80-6.75 (m, 4H), 6.73 (s, 2H), 5.29 (br. s, 2H), 5.04 (br. s, 2H), 4.52 (s, 2H), 4.26-4.05 (m, 6H), 3.72-3.61 (m, 4H), 3.16 (A of AB, d, J=13.4 Hz, 1H), 3.14 (A of AB, d, J=13.5 Hz, 1H), 2.77 (B of AB, d, J=13.5 Hz, 1H), 2.75 (B of AB, d, J=13.4 Hz, 1H), 1.44 (s, 18H), 1.43 (s, 18H), 1.06 (s, 3H), 1.05 (s, 3H).

Intermediate III.2.b.1.1 (Scheme 3.2)

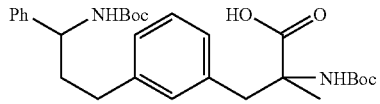

Step A-D: conversion of benzaldehyde to tert-butyl (1-phenylprop-2-en-1-yl)carbamate was performed using vinyl Grignard as described in D. A. Cogan et al. Tetrahedron 55 (1999) 8883-8904, followed by standard Boc installation. Separation of the 2 diastereoisomers at the Grignard-sulfimine product stage by flash chromatography on silica gel allowed the preparation of R— tert-butyl (1-phenylprop-2-en-1-yl)carbamate and S— tert-butyl (1-phenylprop-2-en-1-yl)carbamate separately, which could be carried separately in the following steps.

Step E: Hydroboration and Pd$^0$ Coupling

Solid tert-butyl (1-phenylprop-2-en-1-yl)carbamate (0.436 g, 1.87 mmol) was placed in an oven-dried flask under an atmosphere of argon and dissolved in 9-borabicyclo[3.3.1] nonane (3.91 mL, 1.95 mmol, 0.5M solution in THF) and heated to 70° C. After 45 min, the reaction was allowed to cool to rt and was added in one portion via syringe to a separate oven dried flask containing intermediate I.1.b.1 (0.785 g, 1.78 mmol), Pd(PPh$_3$)$_4$ (0.103 g, 0.089 mmol), 3.2N NaOH (0.834 mL, 2.67 mmol), and 3 mL degassed toluene. The resulting solution was allowed to stir at 85° C. After 16 hr, the crude reaction was diluted with water and filtered over celite, washing with EtOAc. The layers were separated, and the resulting organic layer was washed with brine, dried over sodium sulfate, and concentrated in vacuo. Purification by flash chromatography (40 g silica, 0-20% EtOAc in hexanes) gave methyl 2-[(tert-butoxycarbonyl)amino]-3-(3-{3-[(tert-butoxycarbonyl)amino]-3-phenylpropyl}phenyl)-2-methylpropanoate as a light tan foam.

Step F: Ester Hydrolysis

To a solution of methyl 2-[(tert-butoxycarbonyl)amino]-3-(3-{3-[(tert-butoxycarbonyl)amino]-3-phenylpropyl}phenyl)-2-methylpropanoate (0.296 g, 0.562 mmol) in MeOH (8 mL) and THF (8 mL) was added 1N LiOH (5.62 mL, 5.62 mmol). After stirring at rt for 16 hr., the reaction was heated to 45° C. After 2 hr. at 45° C., 1N HCl (5.7 mL, 5.7 mmol) was added. The reaction mixture was diluted with water and extracted with CHCl$_3$ (×2), dried over sodium sulfate, and concentrated in vacuo to give intermediate III.2.b.1.1 as a white foam. $^1$H NMR (400 MHz, CD$_3$OD) δ 7.32-7.12 (m, 6H), 7.03 (d, J=6.2 Hz, 1H), 6.99-6.94 (m, 2H), 4.51-4.44 (m, 1H), 3.26 (A of AB, d, J=13.4 Hz, 1H), 3.14 (B of AB, br d, J=13.4 Hz, 1H), 2.68-2.48 (m, 2H), 2.07-1.89 (m, 2H), 1.52-1.20 (m, 21H).

Intermediate III.2.c.1.1 (Scheme 3.2)

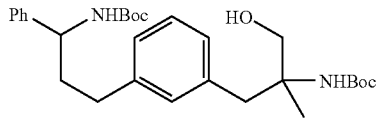

Prepared from LiBH$_4$ reduction of ester obtained in intermediate II.2.b.1.1, step E, using a similar procedure as described in intermediate III.1.c.1 preparation, step E. $^1$H NMR (two diastereomers) (400 MHz, CDCl$_3$) δ 7.38-7.31 (m, 4H), 7.29-7.15 (m, 8H), 7.04-6.97 (m, 6H), 4.87-4.08 (m, 6H), 3.72-3.63 (m, 4H), 3.21 (A of AB, d, J=13.6 Hz, 1H), 3.14 (A of AB, d, J=13.3 Hz, 1H), 2.80 (B of AB, d, J=13.3 Hz, 1H), 2.73 (B of AB, d, J=13.6 Hz, 1H), 2.67-2.52 (m, 4H), 2.23-1.98 (m, 4H), 1.46 (s, 9H), 1.44 (s, 9H), 1.41 (br s, 18H), 1.09 (s, 3H), 1.05 (s, 3H).

Intermediate III.2.c.1.2 (Scheme 3.2)

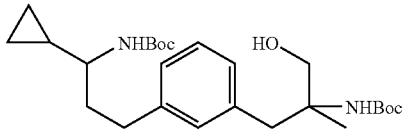

Prepared from tert-butyl (1-cyclopropylprop-2-en-1-yl)carbamate (prepared from cyclopropyl carboxaldehyde and vinyl Grignard) and intermediate I.1.b.1 using a similar procedure as described for the preparation of intermediates III.2.b.1.1 and III.2.c.1.1

Intermediate III.2.b.1.3 (Scheme 3.2)

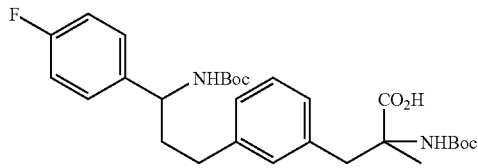

Prepared from tert-butyl (1-(4-fluorophenyl)-prop-2-en-1-yl)carbamate (prepared from 4-fluorobenzaldehyde and vinyl Grignard) and intermediate I.1.b.1 using a similar procedure as described for the preparation of intermediates II.2.b.1.1. MS M+1=531.

Intermediate III.2.c.1.3 (Scheme 3.2)

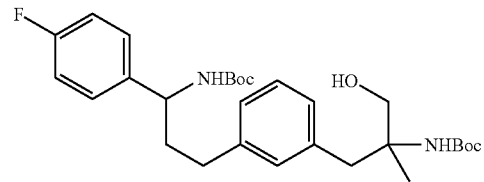

Prepared from intermediate III.2.b.1.3 methyl ester precursor using a similar procedure as described for the preparation of intermediate III.2.c.1.1. MS M+1=517.

Intermediate III.2.b.1.4 (Scheme 3.2)

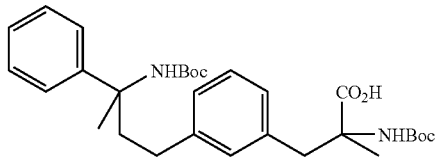

Prepared from tert-butyl (1-methyl-1-phenylprop-2-en-1-yl)carbamate (prepared from Boc protection of 2-phenylbut-3-en-2-amine, Synth. Comm 2000, 30(9), 1643-1650) and intermediate I.1.c.1 using a similar procedure as described for the preparation of intermediates III.2.b.1.1. MS M+1=527.

Intermediate III.2.b.2.1 (Scheme 3.2)

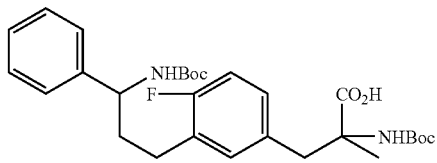

Prepared from tert-butyl (1-phenyl)-prop-2-en-1-yl)carbamate (prepared from benzaldehyde and vinyl Grignard) and intermediate I.1.c.2 using a similar procedure as described for the preparation of intermediate III.2.b.1.1. MS M+1=531.

Intermediate III.2.b.2.3 (Scheme 3.2)

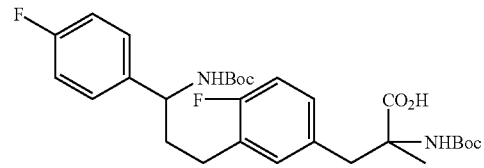

Prepared from tert-butyl (1-(4-fluorophenyl)-prop-2-en-1-yl)carbamate (prepared from 4-fluorobenzaldehyde and vinyl Grignard) and intermediate I.1.c.2 using a similar procedure as described for the preparation of intermediate II.2.b.1.1. MS M+1=550.

Intermediate III.2.b.3.1 (Scheme 3.2)

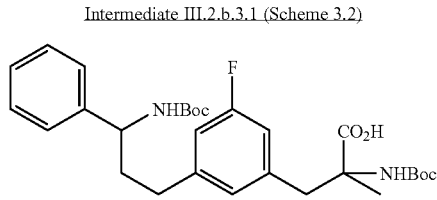

Prepared from tert-butyl (1-phenyl)-prop-2-en-1-yl)carbamate (prepared from benzaldehyde and vinyl Grignard) and intermediate I.1.c.3 using a similar procedure as described for the preparation of intermediate III.2.b.1.1. MS M+1=531.

Intermediate III.2.b.3.3 (Scheme 3.2)

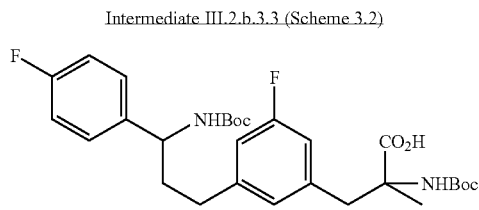

Prepared from tert-butyl (1-(4-fluorophenyl)-prop-2-en-1-yl)carbamate (prepared from 4-fluorobenzaldehyde and vinyl Grignard) and intermediate I.1.c.3 using a similar procedure as described for the preparation of intermediate III.2.b.1.1. MS M+1=550.

Intermediate III.2.b.4.1 (Scheme 3.2)

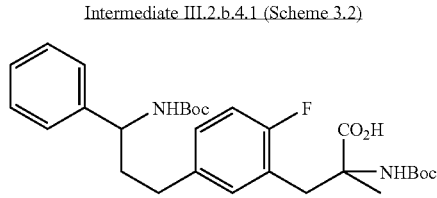

Prepared from tert-butyl (1-phenyl)-prop-2-en-1-yl)carbamate (prepared from benzaldehyde and vinyl Grignard) and intermediate I.1.c.4 using a similar procedure as described for the preparation of intermediate III.2.b.1.1. MS M+1=531.

Intermediate III.2.b.4.3 (Scheme 3.2)

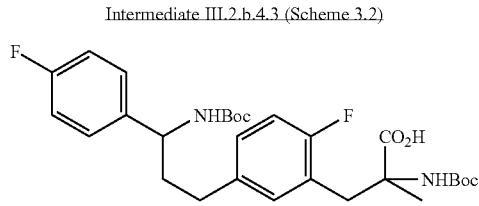

Prepared from tert-butyl (1-(4-fluorophenyl)-prop-2-en-1-yl)carbamate (prepared from 4-fluorobenzaldehyde and vinyl Grignard) and intermediate I.1.c.4 using a similar procedure as described for the preparation of intermediate III.2.b.1.1. MS M+1=550.

Intermediate III.2.b.5.1 (Scheme 3.2)

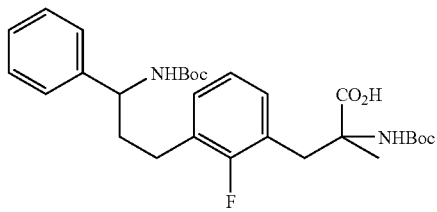

Prepared from tert-butyl (1-phenyl)-prop-2-en-1-yl)carbamate (prepared from benzaldehyde and vinyl Grignard) and intermediate I.1.c.5 using a similar procedure as described for the preparation of intermediate III.2.b.1.1. MS M+1=531.

Intermediate III.2.b.5.3 (Scheme 3.2)

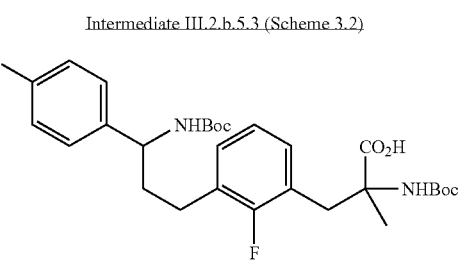

Prepared from tert-butyl (1-(4-fluorophenyl)-prop-2-en-1-yl)carbamate (prepared from 4-fluorobenzaldehyde and vinyl Grignard) and intermediate I.1.c.5 using a similar procedure as described for the preparation of intermediate III.2.b.1.1. MS M+1=550.

Intermediate III.2.c.1.1.F (Scheme 3.2)

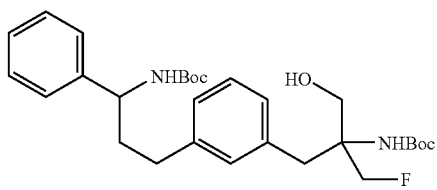

Prepared from tert-butyl (1-phenylprop-2-en-1-yl)carbamate (prepared from benzaldehyde and vinyl Grignard) and intermediate I.1.b.2 using a similar procedure as described for the preparation of intermediates III.2.b.1.1 and III.2.c.1.1. $^1$H NMR (400 MHz, CDCl$_3$) δ 7.34 (m, 2H), 7.25 (m, 4H), 7.05 (m, 3H), 4.86 (m, 2H), 4.57-4.28 (m, 3H), 3.88 (bs, 1H), 3.71 (m, 2H), 3.08 (m, 1H), 2.89 (t, J=14 Hz, 1H), 2.59 (t, J=5 Hz, 2H), 2.07 (m, 2H), 1.46 (s, 9H), 1.45 (s, 9H).

Intermediate III.2.c.1.1.H (Scheme 3.2)

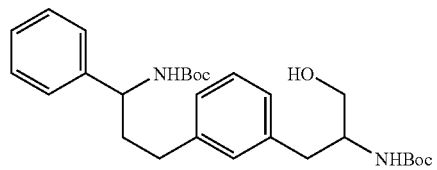

Prepared from tert-butyl (1-phenylprop-2-en-1-yl)carbamate (prepared from benzaldehyde and vinyl Grignard) and intermediate I.1.b.3 using a similar procedure as described for the preparation of intermediates III.2.b.1.1 and II.2.c.1.1. $^1$H NMR (400 MHz, CDCl$_3$) δ 7.36-7.28 (m, 2H), 7.28-7.16 (m, 4H), 7.16-7.06 (m, 2H), 7.02-6.96 (m, 1H), 5.14-4.96 (m, 1H), 4.92-4.78 (m, 1H), 4.60-4.46 (m, 1H), 3.90-3.74 (m, 1H), 3.66-3.48 (m, 2H), 3.24-3.14 (m, 1H), 2.96-2.76 (m, 2H), 2.62 (app t, J=7.2 Hz, 2H), 2.20-2.06 (m, 1H), 2.06-1.94 (m, 1H), 1.44 (s, 18H).

Intermediate III.2.c.1.4 (Scheme 3.2)

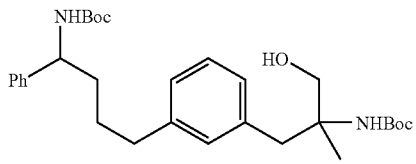

Prepared from tert-butyl (1-phenylbut-3-en-1-yl)carbamate (prepared from benzaldehyde and allyl Grignard) and intermediate I.1.b.1 using a similar procedure as described for the preparation of intermediates III.2.b.1.1 and III.2.c.1.1 $^1$H NMR (400 MHz, CDCl$_3$) δ 7.32-7.29 (m, 2H), 7.26-7.17 (m, 4H), 7.02-6.95 (m, 3H), 4.90-4.82 (br d, 1H), 4.60 (s, 1H), 4.57 (s, 1H), 4.25-4.20 (br d, 1H), 3.66-3.60 (m, 2H), 3.12 (A of AB, d, J=13.1 Hz, 1H). 2.78 (B of AB, d, J=13.1 Hz, 1H), 2.65-2.55 (m, 2H), 1.87-1.57 (m, 4H), 1.75 (s, 3H), 1.46-1.42 (br s, 18H).

Intermediate III.2.c.1.5 (Scheme 3.2)

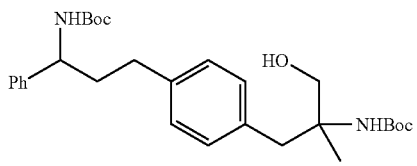

Prepared from tert-butyl (1-phenylprop-2-en-1-yl)carbamate (prepared from benzaldehyde and vinyl Grignard) and intermediate I.1.b.2 using a similar procedure as described for the preparation of intermediates III.2.b.1.1 and III.2.c.1.1 $^1$H NMR (400 MHz, CDCl$_3$) δ 7.34-7.22 (m, 5H), 7.08 (s, 4H), 4.98 (apparent d, 1H), 4.71-4.65 (br s, 1H), 4.61-4.58 (br s, 1H), 4.35-4.23 (br s, 1H), 3.69-3.59 (m, 2H), 3.12 (A of AB, d, J=13.2 Hz, 1H). 2.75 (B of AB, d, J=13.2 Hz, 1H), 2.68-2.61 (m, 1H), 2.58-2.51 (m, 1H), 2.15-2.0 (br s, 2H), 1.75 (s, 3H), 1.5-1.4 (br s, 18H), 1.05 (s, 3H).

Intermediate III.2.c.1.6 (Scheme 3.2)

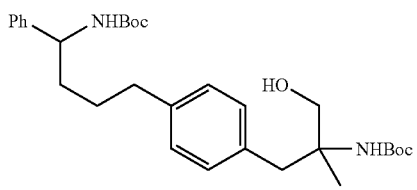

Prepared from tert-butyl (1-phenylbut-3-en-1-yl)carbamate (prepared from benzaldehyde and allyl Grignard) and intermediate I.1.b.2 using a similar procedure as described for the preparation of intermediates III.2.b.1.1 and III.2.c.1.1 $^1$H NMR (400 MHz, CDCl$_3$) δ 7.30-7.25 (m, 2H), 7.24-7.18 (m, 3H), 7.07-7.02 (m, 4H), 4.92 (apparent d, 1H), 4.63-4.60 (br s, 1H), 4.58 (s, 1H), 4.33-4.21 (br s, 1H), 3.63-3.61 (m, 2H), 3.09 (A of AB, d, J=13.1 Hz, 1H). 2.75 (B of AB, d, J=13.1 Hz, 1H), 2.59-2.55 (m, 2H), 1.82-1.51 (br m, 4H), 1.4-1.3 (br s, 18H), 1.04 (s, 3H).

Intermediate III.2.e.1 (Scheme 3.2)

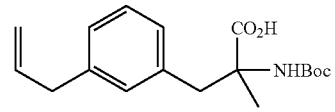

Step A: Stille Coupling to Intermediate I.1.c.1

To a solution of I.1.c.1 (1.5 g, 4.02 mmol) in toluene (10 ml) was added allyltributyltin (1.06 ml, 5.23 mmol) and tetrakis(triphenylphosphine)palladium (0) (0.465 g, 0.402 mmol). Degas and stir overnight at 90° C. Dilute with EtOAc and wash with water five times. The organic layer was added water (100 ml) and KF (5 g) and stirred for 1 hour. The organic layer was dried, concentrated and purified by flash column chromatography (30% EtOAc/Hex) affording 1.08 g desired product. $^1$H NMR (400 MHz, CDCl$_3$) δ 7.19 (t, J=7.5 Hz, 1H), 7.06 (d, J=7.5 Hz, 1H), 6.91 (d, J=8.6 Hz, 2H), 5.97-5.89 (m, 1H), 5.18-5.12 (br s, 1H), 5.07-5.02 (m, 2H), 3.75 (s, 3H), 3.34 (d, J=6.6 Hz, 3H), 3.16 (d, J=13.3 Hz, 1H), 1.46 (s, 9H).

Step B: Hydrolysis

Performed as described in the preparation of intermediate III.2.b.1.1, step F. $^1$H NMR (400 MHz, CDCl$_3$) δ 7.21 (d, J=7.5 Hz, 1H), 7.09 (d, J=7.3 Hz, 1H), 7.01-6.97 (m, 2H), 6.02-5.92 (m, 1H), 5.07-5.03 (m, 2H), 4.93 (s, 1H), 3.37-3.32 (m, 3H), 3.20 (d, J=13.3 Hz, 1H), 1.52 (s, 3H), 1.48 (s, 9H).

Intermediate III.2.f.1 (Scheme 3.2)

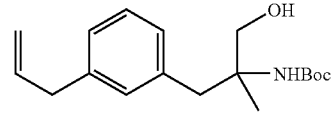

Prepared by lithium borohydride reduction of the methyl ester of intermediate III.2.e.1 (Step A) as described in the preparation of intermediate I.1.c.1. MS M+1=306.

Intermediate III.3.a.1 (Scheme 3.3)

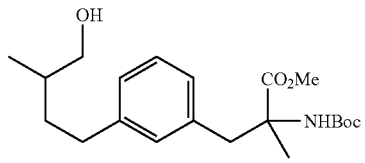

Prepared from 2-methyl-3-buten-1-ol via O-benzylation, hydroboration, Pd$^0$ coupling to intermediate I.1.b.1 (using similar procedures as described in the preparation of intermediate III.2.b.1.1) and hydrogenolysis of the benzyl ether under standard conditions. $^1$H NMR (400 MHz, CDCl$_3$) δ 7.16-7.12 (m, 1H), 7.04-7.02 (m, 1H), 6.87-6.84 (m, 2H), 5.20-5.15 (br, 1H), 3.72 (s, 3H), 3.49-3.45 (m, 1H), 3.42-3.39 (m, 1H), 3.36-3.29 (br, 1H), 3.19-3.15 (m, 1H), 2.69-2.61 (m, 1H), 2.58-2.50 (m, 1H), 1.74-1.69 (m, 2H), 1.63-1.55 (m, 1H), 1.48 (s, 3H), 1.43 (s, 9H), 0.93 (d, J=7 Hz, 1H).

Intermediate III.4.a.1.1 (Scheme 3.4)

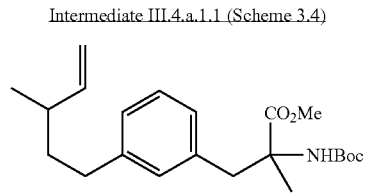

3-Methyl-1,4-pentadiene (1.39 g, 16.9 mmol) was placed in an oven dried round bottom flask and dissolved in 0.5 M solution of 9-BBN (5.43 mL, 2.78 mmol) and the reaction was allowed to stir at 75° C. for 45 minutes. The reaction was then allowed to cool to rt and was added in one portion via syringe to another oven dried round bottom flask containing the intermediate I.1.b.1 (1.0 g, 2.27 mmol), Pd(PPh$_3$)$_4$ (0.26 g, 0.23 mmol), 3.2 M NaOH (1.06 µL, 3.40 mmol), and 2 µL of degassed toluene. This solution was then allowed to stir at 85° C. for 16 h. The crude reaction was filtered over celite using EtOAc to wash. The resulting organic layer was washed with DI water (×3), brine (×3), dried over sodium sulfate and concentrated in vacuo. The crude material was purified using flash chromatography (145 g silica, 0-20% EtOAc in hexanes) to afford the corresponding intermediate III.4.a.1.1. $^1$H NMR (400 MHz, CDCl$_3$) δ 7.19-7.15 (m, 1H), 7.05 (app d, J=7.5 Hz, 1H), 6.89 (s, 1H), 6.87 (s, 1H), 5.76-5.67 (m, 1H), 5.15-5.10 (br s, 1H), 5.00-4.95 (m, 2H), 3.75 (s, 3H), 3.38-3.28 (br s, 1H), 3.16 (B of AB, d, J=13.3 Hz, 1H), 2.62-2.48 (m, 1H), 2.42-2.39 (m, 1H), 2.18-2.05 (m, 1H), 1.91-1.85 (m, 1H), 1.60-1.4 (m, 12H), 1.02 (d, J=6.8 Hz, 3H).

Intermediate III.5.a.1 (Scheme 3.5)

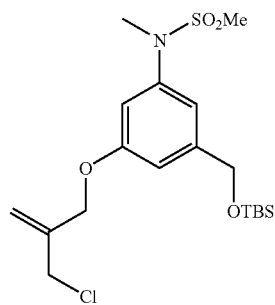

Intermediate I.1.a.1 (0.5 g, 1.45 mmol) and 3-chloro-2-chloromethyl propene (0.84 mL, 7.24 mmol) were dissolved in 5 mL of anhydrous DMF. Cesium carbonate (0.52 g, 1.52 mmol) was added in one portion and the reaction was allowed to stir at rt for 24 h. The crude reaction was extracted with EtOAc (×3), washed with DI water (×3), saturated LiCl (×3), dried over sodium sulfate and concentrated in vacuo. The crude material was purified using flash chromatography (20 g silica, 0-30% EtOAc in hexanes) to afford intermediate III.5.a.1. $^1$H NMR (400 MHz, CDCl$_3$) δ 6.83 (s, 1H), 6.76 (s, 2H), 5.29 (s, 1H), 5.26 (s, 1H), 4.60 (s, 2H), 4.53 (s, 2H), 4.08 (s, 2H), 3.19 (s, 3H), 2.73 (s, 3H), 0.84 (s, 9H), 0.00 (s, 6H).

Intermediate IV.4.e.2 (Scheme 4.4)

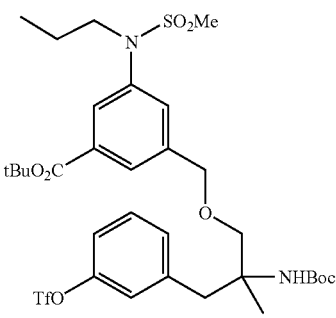

To a slurry of poly(2,6-di-tert-butyl-4-vinylpyridine (1.52 g, 2.73 mmol, loading=1.8 mmol N/g) and 4 A sieves (spatula tip) in 15 mL anhydrous dichloroethane at rt under an atmosphere of argon was added intermediate I.1.c.1 (0.565 g, 1.37 mmol). After stirring for 15 min., a solution of intermediate II.2.c.2 (0.666 g, 1.64 mmol) in 7 mL anhydrous dichloroethane was added followed by silver trifluoromethanesulfonate (0.527 g, 2.05 mmol). After 16 hr., additional silver trifluoromethanesulfonate (0.527 g, 2.05 mmol) was added. After an additional 16 hr, it was filtered over celite, washing with dichloromethane and methane, and concentrated in vacuo. Purification by flash chromatography (120 g silica, 0-40% EtOAc in hexanes) gave intermediate IV.4.e.2 as a white foam. $^1$H NMR (400 MHz, CDCl$_3$) δ 7.91 (s, 1H), 7.85 (s, 1H), 7.53 (s, 1H), 7.35 (app t, J=7.9 Hz, 1H), 7.21-7.12 (m, 2H), 7.10 (s, 1H), 4.64-4.54 (m, 3H), 3.66 (t, J=7.2 Hz, 2H), 3.49 (A of AB, d, J=8.9 Hz, 1H), 3.45 (B of AB, d, J=8.9 Hz, 1H), 3.24 (A of AB, d, J=13.2 Hz, 1H), 3.02 (B of AB, d, J=13.2 Hz, 1H), 2.89 (s, 3H), 1.60 (s, 9H), 1.55-1.45 (m, 2H), 1.46 (s, 9H), 1.26 (s, 3H), 0.91 (t, J=7.3 Hz, 3H).

Intermediate IV.9.b.1 (Scheme 4.9)

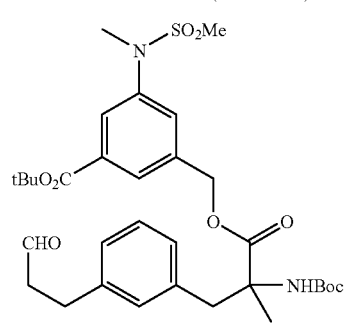

Step A: Coupling of Intermediates II.2.c.1 and III.2.e.1

To a solution of intermediate II.2.c.1 (0.100 g, 0.264 mmol) and intermediate III.2.e.1 (0.084 g, 0.264 mmol) in 1 mL DMF was added cesium carbonate (0.095 g, 0.291 mmol). After 1.5 hr., the reaction was diluted with LiCl (aq) (25 mL) and extracted with EtOAc (2×25 mL). The organic layers were combined, washed with LiCl (aq) and brine, dried over sodium sulfate, and concentrated in vacuo. Purification by flash chromatography (10% EtOAc in chloroform) gave 3-(tert-butoxycarbonyl)-5-[methyl(methylsulfonyl)amino] benzyl 3-allyl-N-(tert-butoxycarbonyl)-alpha-methylphenylalaninate. MS M+1=517 (—BOC).

Step B: Hydroboration

The olefin (0.122 g, 0.198 mmol) in THF (10 ml) was added borane THF (0.396 ml, 0.396 mmol). Stir at RT for 1 hr 45 minute. The solution was carefully added water (8 ml) followed by sodium perborate (0.091 g, 0.593 mmol). The solution stirred for 2 hours at room temperature. Extract 3× with EtOAc and wash with brine. The organics were dried and concentrated affording crude 3-(tert-butoxycarbonyl)-5-[methyl(methylsulfonyl)amino]benzyl N-(tert-butoxycarbonyl)-3-(3-hydroxypropyl)-alpha-methylphenylalaninate. MS M+1=535 (—BOC).

Step C: Oxidation

The alcohol (0.105 g, 0.165 mmol) in CH$_2$Cl$_2$ (2 ml) was added 4 A (0.025 g) sieves and 4-methylmorpholine N-oxide (0.034 g, 0.248). Stir for 10 minutes then added tetrapropylammonium perruthenate (0.003, 0.008 mmol). After 1 hour the solution was filtered, concentrated, and purified on silica gel (50% EtOAc/Hex). MS M+1=533.3 (—BOC).

Intermediate IV.10.b.1 (Scheme 4.9)

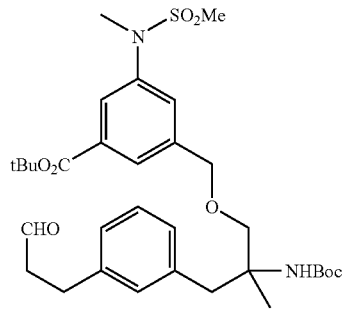

Prepared from the silver triflate coupling of intermediates II.2.c.1 and III.2.f.1 as described in the preparation of intermediate IV.4.e.2, followed by hydroboration and oxidation as described in the preparation of intermediate IV.9.b.1. MS M+1=619.

Intermediate IV.9.b.2 (Scheme 4.9)

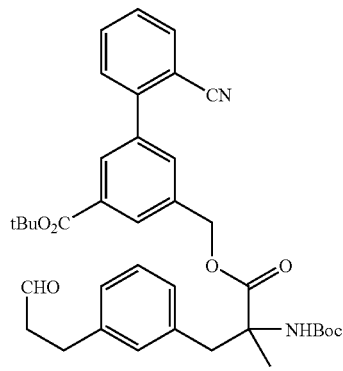

Prepared from intermediates II.3.f.1 and III.2.e.1 as described for the preparation of intermediate IV.6.b.1. MS M+1=627.

EXAMPLE 1 (Scheme 4.2)

EXAMPLE 1

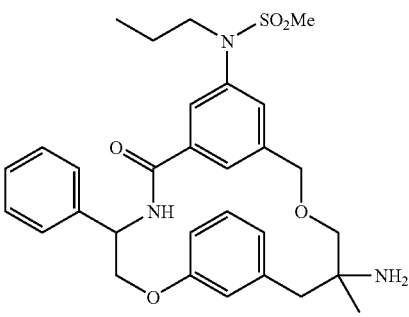

Step A: Ether Formation

Ether formation with intermediates II.1.c.2 and III.1.c.1 was performed using a similar procedure as described in the preparation of intermediate IV.4.e.2 to give methyl 3-{[2-[(tert-butoxycarbonyl)amino]-3-(3-{2-[(tert-butoxycarbonyl)amino]-2-phenylethoxy}phenyl)-2-methylpropoxy]methyl}-5-[(methylsulfonyl)(propyl)amino]benzoate as a colorless oil.

Step B: Boc Removal, Hydrolysis.

Methyl 3-{[2-[(tert-butoxycarbonyl)amino]-3-(3-{2-[(tert-butoxycarbonyl)amino]-2-phenylethoxy}phenyl)-2-methylpropoxy]methyl}-5-[(methylsulfonyl)(propyl)amino] benzoate (0.027 g, 0.034 mmol) from step A was taken up in 5.0 mL of an HCl saturated solution of dichloromethane. After 60 hr, the reaction was concentrated in vacuo. The resulting deprotected material was taken up in 1.5 mL tetrahydrofuran, and 1N LiOH (0.350 mL, 0.350 mmol) was added. After 6 hr., it was acidified to pH 4 with 1N HCl (0.380 mL, 0.380 mmol) and concentrated under reduced pressure to give the resulting acid.

Step C: BOP Cyclization

To a solution of acid from step B (0.010 g, 0.018 mmol) in 5 mL DMF was added diisopropylethylamine (0.005 mL, 0.026 mmol) and benzotriazol-1-yloxytris(dimethylamino)-phosphonium hexafluorophosphate (0.009 g, 0.021 mmol). After 1 hr, the crude reaction mixture was purified by preparative HPLC (5->95% CH$_3$CN/H$_2$O, 0.1% added TFA, C18 PRO YMC 20×150 mm) to afford Example 1 as a white solid. $^1$H NMR (400 MHz, CD$_3$OD) δ 8.82 (d, J=8.4 Hz, 1H), 7.71 (s, 1H), 7.69 (s, 1H), 7.58 (s, 1H), 7.56 (s, 1H), 7.43-7.38 (m, 3H), 7.35-7.23 (m, 3H), 7.04 (, J=8.2 Hz, 1H), 6.88 (d, J=7.6 Hz, 1H), 5.61-5.55 (m, 1H), 5.04 (A of AB, d, J=13.8 Hz, 1H), 4.58-4.51 (m, 3H), 3.72-3.60 (m, 2H), 3.37 (A of AB, d, J=10.7 Hz, 1H), 5.17 (A of AB, d, J=13.2 Hz, 1H), 3.04 (B of AB, d, J=10.7 Hz, 1H), 2.92 (s, 3H), 2.85 (B of AB, d, J=13.2 Hz, 1H), 1.48 (m, 2H), 1.26 (s, 3H), 0.88 (t, J=7.4 Hz, 3H).

Separation of the corresponding 4 diastereoisomers (RS, RR, SS, SR) was performed by preparative chiral HPLC.

EXAMPLE 2 (Scheme 4.3)

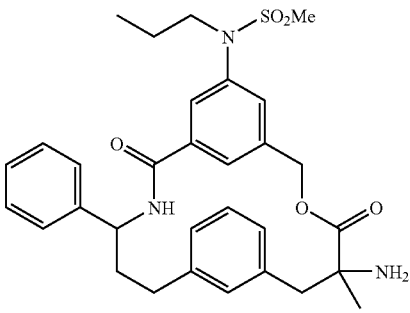

Step A: Ester Formation

To a solution of intermediate II.2.c.2 (0.228 g, 0.562 mmol) and intermediate III.2.b.1.1 (0.288 g, 0.562 mmol) in 3 mL DMF was added cesium carbonate (0.220 g, 0.674 mmol). After 1.5 hr., the reaction was diluted with LiCl (aq) (25 mL) and extracted with EtOAc (2×25 mL). The organic layers were combined, washed with LiCl (aq) and brine, dried over sodium sulfate, and concentrated in vacuo. Purification by flash chromatography (20 g silica, 0-40% EtOAc in hexanes) gave tert-butyl 3-({[2-[(tert-butoxycarbonyl)amino]-3-(3-{3-[(tert-butoxycarbonyl)amino]-3-phenylpropyl}phenyl)-2-methylpropanoyl]oxy}methyl)-5-[(methylsulfonyl)(propyl)amino]benzoate as a white foam.

Step B: Boc and tBu Ester Removal

Tert-butyl 3-({[2-[(tert-butoxycarbonyl)amino]-3-(3-{3-[(tert-butoxycarbonyl)amino]-3-phenylpropyl}phenyl)-2-methylpropanoyl]oxy}methyl)-5-[(methylsulfonyl)(propyl)amino]benzoate (0.386 g, 0.461 mmol) was taken up in 2.0 mL HCl in dioxane (2.00 mL, 8.01 mmol, 4.0M solution). After 16 hr., the reaction was concentrated in vacuo, taken up in dichloromethane, and concentrated again (×2) to give 3-[({2-amino-3-[3-(3-amino-3-phenylpropyl)phenyl]-2-methylpropanoyl}oxy)methyl]-5-[(methylsulfonyl)(propyl)amino]benzoic acid dihydrochloride as a white solid.

Step C: BOP Cyclization

Cyclization of 3-[({2-amino-3-[3-(3-amino-3-phenylpropyl)phenyl]-2-methylpropanoyl}oxy)methyl]-5-[(methylsulfonyl)(propyl)amino]benzoic acid dihydrochloride was performed as described in the preparation of Example 1 to provide Example 2 as a white solid. $^1$H NMR (400 MHz, CD$_3$OD) δ 7.53 (s, 1H), 7.37-7.34 (m, 3H), 7.33-7.27 (m, 3H), 7.23-7.18 (m, 1H), 7.07 (d, J=7.4 Hz, 1H), 6.82 (t, J=7.5 Hz, 1H), 6.76 (d, J=7.7 Hz, 1H), 6.08 (s, 1H), 5.56 (A of AB, d, J=14.4 Hz, 1H), 5.23 (d, J=10.0 Hz, 1H), 4.77 (B of AB, d, J=14.4 Hz, 1H), 3.64-3.56 (m, 2H), 3.16-3.07 (m, 2H), 2.88 (s, 3H), 2.86-2.78 (m, 2H), 2.50-2.38 (m, 1H), 2.28-2.20 (m, 1H), 1.62 (s, 3H), 1.47-1.33 (m, 2H), 0.87 (t, J=7.4 Hz, 3H).

Separation of the corresponding 4 diastereoisomers (RS, RR, SS, SR) was performed by preparative chiral HPLC.

EXAMPLE 3 (Scheme 4.3)

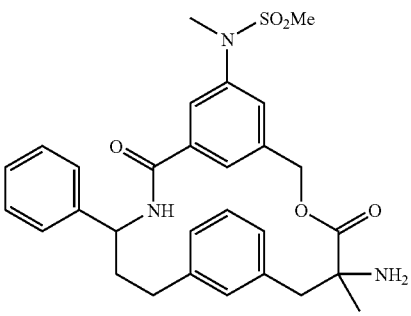

Step A: Ester formation (intermediates II.3.c and III.2.b.1.1), using a similar procedure as described in the preparation of Example 2.

Step B: Boc and tBu ester removal, macrolactamization, using a similar procedure as described in the preparation of Example 2.

Step C: Boc Installation

To a solution of 5-amino-19-bromo-5-methyl-14-phenyl-3-oxa-15-azatricyclo[15.3.1.1$^{7,11}$]docosa-1(21),7(22),8,10,17,19-hexaene-4,16-dione from Step B (1.35 g, 2.66 mmol) in THF (10 mL) was added ditertbutyldicarbonate (700 mg, 3.19 mmol) and the reaction mixture was stirred at 50° C. for 2 h 30 min. Additional ditertbutyldicarbonate (100 mg) was added and the reaction mixture was stirred at 60° C. for 1 h 30 min. The reaction mixture was concentrated in vacuo and purified by flash chromatography (145 g silica, 0-35% EtOAc in hexanes) to provide the corresponding Boc derivative. Separation of the diastereomeric pairs by flash chromatography were possible at this stage.

Step D: Pd$^0$ Coupling of MeNMs

A suspension of bromide from Step C (50 mg, 0.08 mmol), anhydrous potassium phosphate tribasic (24 mg, 0.12 mmol), 9,9-dimethyl-4,5-bis(diphenylphosphino)xanthene (7 mg, 0.01 mmol), Pd$_2$ dba$_3$ (4 mg, 0.004 mmol) and N-methyl-methylsulfonamide (11 mg, 0.1 mmol) in dioxane (0.5 mL) was stirred at 125° C. for 2 h. The reaction mixture was allowed to cool to Rt, diluted with DCM, filtered and purified by flash chromatography (40 g silica, 20-60% EtOAc in hexanes) to provide the corresponding aryl sulfonamide.

Step E: Boc Removal

The aryl sulfonamide from Step D was treated with 4N HCl in dioxane (5 mL) for 1 h 45, concentrated in vacuo and purified by ion exchange chromatography (2 g SCX, MeOH then 2M NH$_3$ in MeOH) to provide Example 3 as a white solid. $^1$H NMR (400 MHz, CD$_3$OD) δ 7.54 (s, 1H), 7.40-7.26 (m, 7H), 7.24-7.18 (m, 1H), 7.06 (d, J=7.1 Hz, 1H), 6.82 (t, J=7.4 Hz, 1H), 6.75 (d, J=7.4 Hz, 1H), 6.03 (s, 1H), 5.56 (A of AB, d, J=14.3 Hz, 1H), 5.23 (d, J=10.7 Hz, 1H), 4.77 (13 of AB, d, J=14.3 Hz, 1H), 3.25 (s, 3H), 3.16-3.06 (m, 2H), 2.86 (s, 3H), 2.84-2.76 (m, 2H), 2.50-2.36 (m, 1H), 2.28-2.18 (m, 1H), 1.62 (s, 3H).

Separation of the corresponding 4 diastereoisomers (RS, RR, SS, SR) was performed by preparative chiral HPLC.

EXAMPLE 4 (Scheme 4.3)

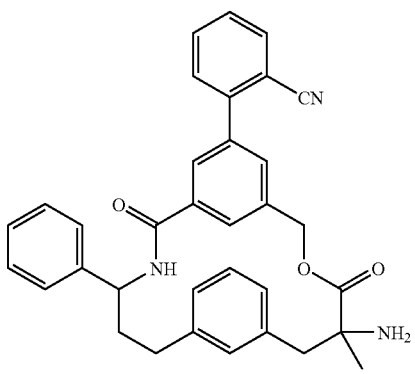

Steps A-C: as described in the preparation of Example 3.

Step D: Pd⁰ Coupling of 2-CN-Ph-ZnI

To a solution of bromide from Example 3, step C (0.190 g, 0.313 mmol) in 1 mL of degassed THF under argon was added 2-cyanophenylzinc bromide solution (0.5 M in THF, 2.50 mL, 1.251 mmol). The solution was degassed, and Pd(PPh$_3$)$_4$ (0.072 g, 0.063 mmol) was added. After the reaction mixture was purged with argon, it was microwaved at 75° C. for 50 min. The reaction was diluted with EtOAc and water. The layers were separated, and the aqueous layer was extracted with EtOAc (2×). The combined organics were washed with brine, dried over Na$_2$SO$_4$, filtered and concentrated. The residue was purified by normal phase chromatography (20->45% EtOAc/hexanes) to obtain the desired biaryl intermediate as a yellow solid. LCMS [M+H]$^+$=630.

Step E: Deprotection

A solution of biaryl intermediate from step D (0.102 g, 0.162 mmol) in 0.5 μL of CH$_2$Cl$_2$ and 0.5 mL of TFA was stirred at rt for 2 hr. The reaction was concentrated, and purified by reverse phase preparative HPLC (5-95% MeCN/H$_2$O containing 0.1% TFA, C18 PRO YMC 20×150 mm) to give the desired Example 4 as white solid. $^1$H NMR (400 MHz, CD$_3$OD) δ 7.84-7.82 (m, 1H), 7.76-7.72 (m, 2H), 7.60-7.54 (m, 3H), 7.36-7.22 (m, 8H), 7.05 (t, J=7.6 Hz, 1H), 6.93 (d, J=7.7 Hz, 1H), 6.10 (s, 1H), 5.74 (d, J=13.9 Hz, 1H), 5.30-5.27 (m, 1H), 5.11 (d, J=13.9 Hz, 1H), 3.41 (d, J=14.3 Hz, 1H), 3.19-3.11 (m, 2H), 2.96-2.89 (m, 1H), 2.39-2.34 (m, 2H), 1.85 (s, 3H). HHRMS exact mass calc for C$_{34}$H$_{31}$N$_3$O$_3$ [M+H]$^+$: 530.2438; observed: 530.2462.

Separation of the corresponding 4 diastereoisomers (RS, RR, SS, SR) was performed by preparative chiral HPLC.

EXAMPLE 5 (Scheme 4.4)

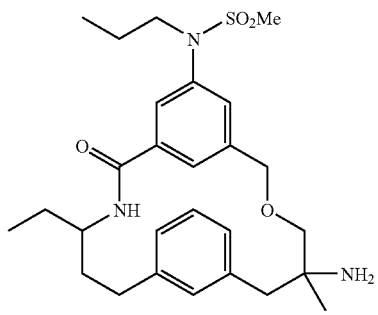

Step A: 9-BBN, Pd⁰ coupling of intermediate IV.4.e.2 and tert-butyl 1-ethylprop-2-enylcarbamate Solid tert-butyl 1-ethylprop-2-enylcarbamate (0.028 g, 0.135 mmol, prepared from propionaldehyde and vinyl Grignard according to D. A. Cogan et al. *Tetrahedron* 55 (1999) 8883-8904, followed by standard Boc installation)) was placed in an oven-dried flask under an atmosphere of argon and dissolved in 9-borabicyclo[3.3.1]nonane (0.532 mL, 0.176 mmol, 0.5M solution in THF) and heated to 70° C. After 1 hr, the reaction was allowed to cool to rt and was added in one portion via syringe to a separate oven dried flask containing intermediate IV.4.e.2 (0.100 g, 0.135 mmol), Pd(PPh$_3$)$_4$ (0.008 g, 0.007 mmol), 3.2N NaOH (0.063 mL, 0.203 mmol), and 0.400 mL degassed toluene. The resulting solution was allowed to stir at 85° C. After 16 hr., the crude reaction was diluted with water and filtered over celite, washing with EtOAc. The layers were separated, and the resulting organic layer was washed with brine, dried over sodium sulfate, and concentrated in vacuo. Purification by flash chromatography (20 g silica, 0-50% EtOAc in hexanes) gave tert-butyl 3-{[2-[(tert-butoxycarbonyl)amino]-3-(3-{3-[(tert-butoxycarbonyl)amino]pentyl}phenyl)-2-methylpropoxy]methyl}-5-[(methylsulfonyl)(propyl)amino]benzoate as a white foam.

Step B: Boc and tBu Ester Removal

Deprotection of 3 tert-butyl 3-{[2-[(tert-butoxycarbonyl)amino]-3-(3-{3-[(tert-butoxycarbonyl)amino]pentyl}phenyl)-2-methylpropoxy]methyl}-5-[(methylsulfonyl)(propyl)amino]benzoate was performed as described in the preparation of Example 2 to provide 3-({2-amino-3-[3-(3-aminopentyl)phenyl]-2-methylpropoxy}methyl)-5-[(methylsulfonyl)(propyl)amino]benzoic acid dihydrochloride as a white solid.

Step C: Bop Cyclization

Cyclization of 3-({2-amino-3-[3-(3-aminopentyl)phenyl]-2-methylpropoxy}methyl)-5-[(methylsulfonyl)(propyl)amino]benzoic acid dihydrochloride was performed as described in the preparation of Example 1 to provide Example 5 as a white solid. $^1$H NMR (400 MHz, CD$_3$OD) δ 7.74 (d, J=9.16 Hz, 1H), 7.63 (s, 1H), 7.30 (s, 1H), 7.24 (s, 1H), 7.09-6.98 (m, 3H), 6.77 (s, 1H), 4.81 (A of AB, d, J=13.7 Hz, 1H), 4.53 (B of AB, d, J=13.7 Hz, 1H), 4.10-4.00 (m, 1H), 3.90 (A of AB, d, J=10.3 Hz, 1H), 3.71-3.59 (m, 2H), 3.45 (B of AB, d, J=10.3 Hz, 1H), 3.20 (A of AB, d, J=13.8 Hz, 1H), 2.95-2.85 (m, 2H), 2.92 (s, 3H), 2.68-2.60 (m, 1H), 2.26-2.17 (m, 1H), 1.91-1.80 (m, 1H), 1.70-1.52 (m, 2H), 1.48-1.37 (m, 2H), 1.33 (s, 3H), 0.97 (t, J=7.4 Hz, 3H), 0.89 (t, J=7.4 Hz, 3H). Separation of the corresponding 4 diastereoisomers (RS, RR, SS, SR) was performed by preparative chiral HPLC.

EXAMPLE 6 (Scheme 4.5)

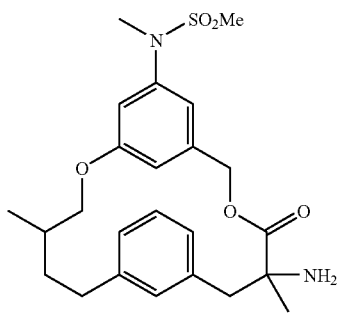

Step A: Mitsunobu etherification (intermediates II.5.d.1 and III.3.a.1)

Intermediate III.3.a.1 (0.22 g, 0.574 mmol), intermediate II.5.d.1 (0.21 g, 0.603 mmol), and tri-n-butyl phosphine (0.22 mL, 0.862 mmol) were dissolved in 10 mL of anhydrous toluene and placed under argon atmosphere. TMAD (0.148 g, 0.862 mmol) was added in one portion and the reaction was allowed to stir at rt for 16 h. The reaction was then concentrated and purified using flash chromatography (40 g silica, 10-40% EtOAc in hexanes) to afford the corresponding phenolic ether.

Step B: TBS Removal and Hydrolysis

The previous phenolic ether (0.247 g, 0.349 mmol) was dissolved in 5 mL of THF. A 1.0 M solution of TBAF (0.52 µL, 0.524 mmol) was added dropwise via syringe. The reaction was allowed to stir at RT for 16 h. The reaction was then concentrated and purified using flash chromatography (40 g silica, 10-70% EtOAc in hexanes) to afford the corresponding benzylic alcohol. The previous benzylic alcohol (0.193 g, 0.326 mmol) was dissolved in 5 mL of THF. A 1.0 M solution of LiOH (3.26 mL, 3.26 mmol) was added in one portion and the reaction was allowed to stir at 50° C. for 16 h. The reaction was then acidified (pH=4) and extracted with EtOAc (×3), dried over sodium sulfate, and the solvent was removed in vacuo to afford the corresponding acid.

Step C: Macrolactonization

The previous acid (0.188 g, 0.33 mmol) and triphenylphosphine (0.128 g, 0.49 mmol) were dissolved in 7 mL of anhydrous THF. DIAD (0.096 mL, 0.49 mmol) was added in one portion via syringe and the reaction was allowed to stir at rt for 5 h. The reaction was then concentrated and purified using flash chromatography (90 g silica, 0-45% EtOAc in hexanes) to afford the corresponding macrolactone.

Step D: Boc Removal

The previous macrolactone (0.205 g, 0.366 mmol) was dissolved in 4.0 M HCl solution in 1,4-dioxane (0.914 mL, 3.65 mmol) and the reaction was allowed to stir at rt for 16 h. The reaction was then concentrated to afford the corresponding macrolactone hydrogen chloride salt, Example 6. $^1$H NMR (two diastereomers) (400 MHz, CD$_3$OD) δ 9.1-9.0 (br s, 2H), 7.16-6.85 (m, 4H), 6.52-6.36 (m, 3H), 5.07 (br s, 2H), 3.85-3.75 (m, 2H), 3.2 (s, 3H), 2.82 (s, 3H), 2.58-2.51 (m, 1H), 2.0-1.8 (m, 4H), 1.89 (s, 3H), 1.35-1.25 (m, 2H), 1.02-0.98 (m, 3H).

EXAMPLE 7 (Scheme 4.6)

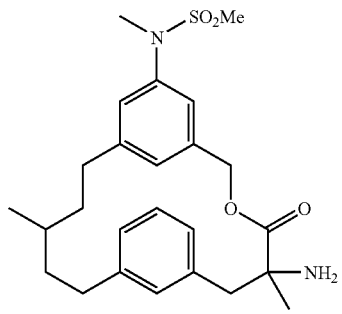

Step A: hydroboration, Pd⁰ coupling (intermediates II.5.e.1 and III.4.a.1.1)

Intermediate III.4.a.1.1 (92 mg, 0.25 mmol) was placed in an oven dried round bottom flask and dissolved in 0.5 M solution of 9-BBN (0.59 mL, 0.29 mmol) and the reaction was allowed to stir at 75° C. for 45 min. The reaction was then allowed to cool to rt and was added in one portion via syringe to another oven dried round bottom flask containing intermediate II.5.e.1 (117 mg, 0.25 mmol), Pd(PPh$_3$)$_4$ (28 mg, 0.02 mmol), 3.2 M NaOH (0.115 mL, 0.37 mmol), and 2 mL of degassed toluene. This solution was then allowed to stir at 85° C. for 16 h. The crude reaction was filtered over celite using EtOAc to wash. The resulting organic layer was washed with DI water (×3), brine (×3), dried over sodium sulfate and concentrated in vacuo. The crude material was purified using flash chromatography (20 g silica, 0-20% EtOAc in hexanes) to afford the corresponding silyl ether.

Step B: TBS removal and hydrolysis, as described in the preparation of Example 6.

Step C: Macrolactonization, as described in the preparation of Example 6.

Step D: Boc removal, as described in the preparation of Example 6 to provide Example 7. $^1$H NMR (two diastereomers) (400 MHz, CD$_3$OD) δ 7.36-7.31 (m, 4H), 7.21-7.05 (m, 4H), 6.96 (d, J=7 Hz, 1H), 6.90 (app triplet, J=7 Hz, 2H), 6.79 (s, 1H), 6.41 (s, 1H), 6.24 (s, 1H), 5.31 (A of AB, d, J=12.2 Hz, 1H). 5.21 (A of AB, d, J=12.4 Hz, 1H), 5.13 (B of AB, d, J=12.4 Hz, 1H), 5.03 (B of AB, d, J=12.2 Hz, 1H), 3.67 (s, 6H), 3.23-3.17 (m, 2H), 3.05-2.99 (m, 2H), 2.91-2.84 (m, 1H), 2.79 (s, 3H), 2.75 (s, 3H), 2.67-2.60 (m, 2H), 2.52-2.45 (m, 1H), 2.40-2.24 (m, 3H), 1.60-1.35 (m, 10H), 1.72 (s, 3H), 1.68 (s, 3H), 0.97 (app triplet, J=6.7 Hz, 6H).

EXAMPLE 8 (Scheme 4.7)

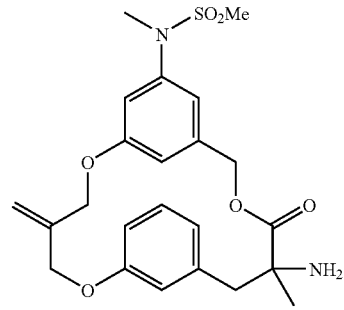

Step A: Phenol alkylation (intermediates I.1.a.1 and I.5.a.1)

Intermediate I.1.a.1 (122 mg, 0.28 mmol) and intermediate III.5.a.1 (87 mg, 0.28 mmol) were dissolved in 5 mL of anhydrous DMF. Cesium carbonate (55 mg, 0.169 mmol) was added in one portion and the reaction was allowed to stir at rt for 24 h. The crude reaction was extracted with EtOAc (×3), washed with DI water (×3), saturated LiCl (×3), dried over sodium sulfate and concentrated in vacuo. The crude material was purified using flash chromatography (20 g silica, 0-25% EtOAc in hexanes) to afford the corresponding alkene.

Step B: TBS removal and hydrolysis, as described in the preparation of Example 6.

Step C: Macrolactonization, as described in the preparation of Example 6.

Step D: Boc removal, as described in the preparation of Example 6 to provide Example 8. $^1$H NMR (400 MHz, CDCl$_3$) δ 7.15 (apparent triplet, J=8 Hz, 1H), 6.93 (s, 1H), 6.89 (s, 1H), 6.79-6.75 (m, 2H), 6.49 (s, 1H), 6.33 (s, 1H), 5.32 (s, 1H), 5.31 (s, 1H), 4.93 (A of AB, d, J=11.9 Hz, 1H), 4.77-4.71 (m, 3H), 4.68 (s, 2H), 3.70 (s, 2H), 3.28 (s, 3H), 3.05 (A of AB, d, J=13.2 Hz, 1H), 2.80 (s, 3H), 2.76 (B of AB, d, J=13.2 Hz, 1H), 1.49 (s, 3H).

EXAMPLE 9 (Scheme 4.7)

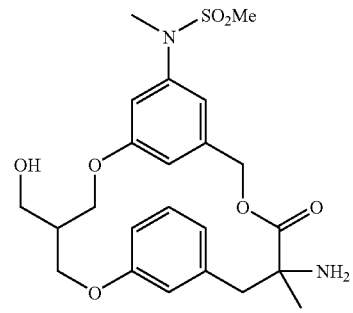

Alkene from Example 8, Step C, (30 mg, 0.054 mmol) was placed in an oven dried round bottom flask and dissolved in anhydrous THF and cooled to 0° C. A 1.0 M solution of $BF_3Et_2O$ (0.064 mL, 0.064=mol) was added dropwise to the solution which was allowed to stir for 1.5 hr at 0° C. The reaction was quenched with a 1 mL solution of a 1:1:1:1 solution of $EtOH:THF:H_2O_2$:pH 7 buffer solution, which was added dropwise at 0° C. The mixture was allowed to stir at rt overnight. The crude reaction mixture was diluted with EtOAc and washed with sodium thiosulfate (×2), DI water (×2), brine (×2), dried over sodium sulfate. Concentration and purification by preparative HPLC (5->95% $CH_3CN/H_2O$, 0.1% added TFA, C18 PRO YMC 20×150 mm) afforded the corresponding alcohol.

Boc removal, as described in the preparation of Example 6 provided Example 9. $^1H$ NMR (two diastereomers) (400 MHz, $CD_3OD$) δ 7.21-1.17 (m, 2H), 7.06-6.98 (m, 4H), 6.86-6.79 (m, 4H), 6.73-6.69 (m, 2H), 6.44-6.29 (m, 2H), 5.36-5.21 (m, 2H), 5.19-5.05 (m, 2H), 4.58-4.24 (m, 3H), 4.25-4.15 (m, 3H), 4.10-3.85 (m, 3H), 3.26 (s, 3H), 3.24 (s, 3H), 3.03-2.97 (m, 2H), 2.82 (s, 3H), 2.80 (s, 3H), 2.75-2.70 (m, 2H), 2.51-2.49 (m, 2H), 2.42 (br s, 2H), 1.65 (s, 3H), 1.64 (s, 3H).

EXAMPLE 10 (Scheme 4.8)

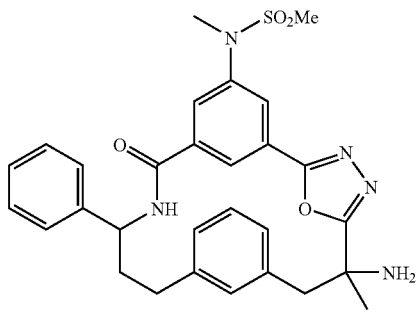

Step A: Coupling of acylhydrazide II.1.e.1 and acid III.2.b.1.1 (EDC, HOAt), followed by cyclodehydration (Burgess reagent, heat).

Step B: Boc and Me ester Removal, as described for the preparation of Example 1.

Step C: BOP Cyclization, as described for the preparation of Example 1. HRMS calculated for $C_{29}H_{31}N_5O_4S$: 546.2170, found: 546.2160.

Separation of the corresponding 4 diastereoisomers (RS, RR, SS, SR) was performed by preparative chiral HPLC.

EXAMPLE 11 (Scheme 4.9)

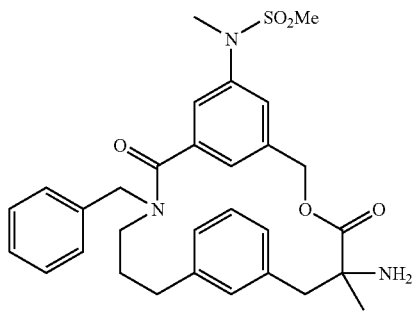

Step A: Reductive Amination

To the aldehyde IV.9.b.1 (0.017 g, 0.027 mmol) in MeOH (2 ml) was added benzylamine (0.003 ml, 0.027 mmol) and acetic acid (0.008 ml, 0.134 mmol). Stir for 30 minutes and added sodiumcyanoborohydride (0.002 g, 0.027 mmol). Stir at room temperature overnight then concentrate, filter, and purify on reverse phase HPLC. MS M+1=724

Step B: Boc and tBu ester removal, as described in example 2, step B.

Step C: BOP cyclization, as described in example 2, step C. MS M+1=550

Additional examples of the compounds of the invention are depicted in Table 1 below. Examples were synthesized, and mass spectrometry data is provided.

TABLE 1

| EX | Scheme and Reference Example | Intermediates | Structure | MS M + 1 |
|---|---|---|---|---|
| 12 | Scheme 4.4 Example 1 | II.1.c.2 III.2.c.1.1 | 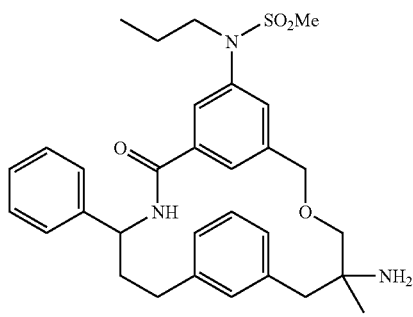 | 550 |

TABLE 1-continued

| EX | Scheme and Reference Example | Intermediates | Structure | MS M + 1 |
|---|---|---|---|---|
| 13 | Scheme 4.4 Example 1 | II.1.c.1 III.2.c.1.1 | 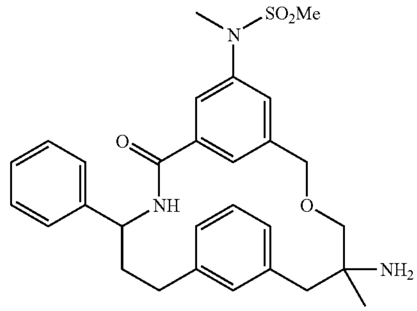 | 522 |
| 14 | Scheme 4.4 Example 1 | II.1.c.3 III.2.c.1.1 | 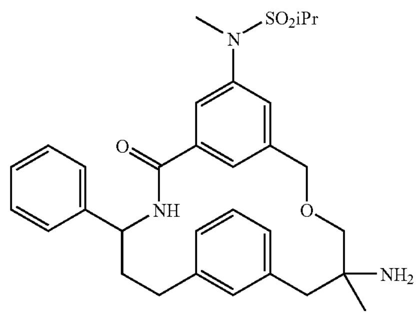 | 550 |
| 15 | Scheme 4.3, 4.4 Example 1, Example 3 | II.3.c III.2.c.1.1 MeNHSO$_2$Et | 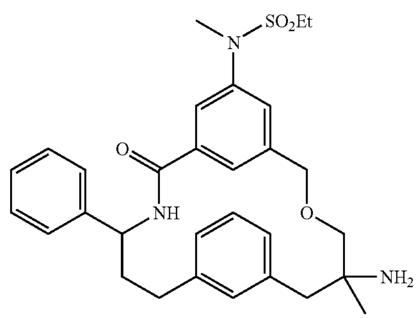 | 536 |
| 16 | Scheme 4.4 Example 1, Example 3 | II.2.c.2 III.2.c.1.1.F | 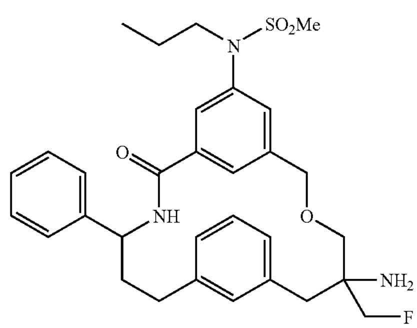 | 568 |

TABLE 1-continued

| EX | Scheme and Reference Example | Intermediates | Structure | MS M + 1 |
|---|---|---|---|---|
| 17 | Scheme 4.3 and 4.4 Examples 2 and 5 | I.1.b.2 hydrolysis then couple to II.2.c.1 Ph—CH(NHBoc)—CH=CH2 9-BBN, Pd⁰, then BOP | 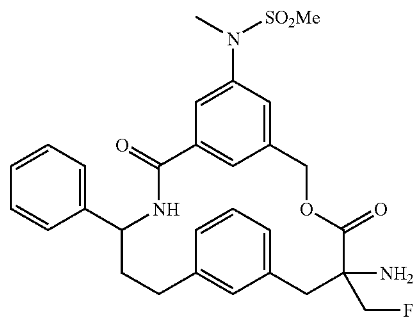 | 554 |
| 18 | Scheme 4.4 Example 2, Example 1 | II.2.c.1 III.2.c.1.1.F | 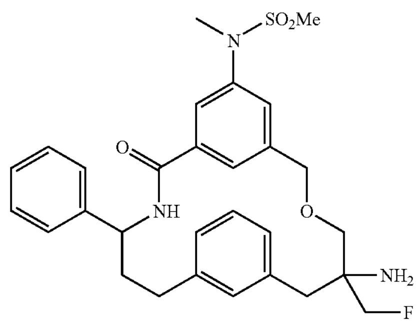 | 540 |
| 19 | Scheme 4.4 Example 2, Example 1 | II.1.c.2 III.2.c.1.1.H | 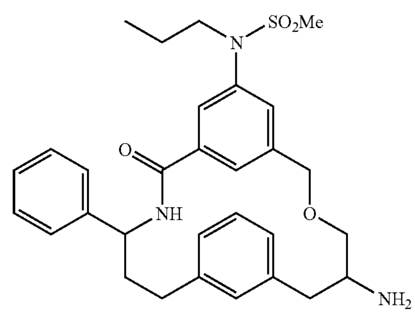 | 536 |
| 20 | Scheme 4.4 Example 1 | II.1.c.3 III.2.c.1.1 | 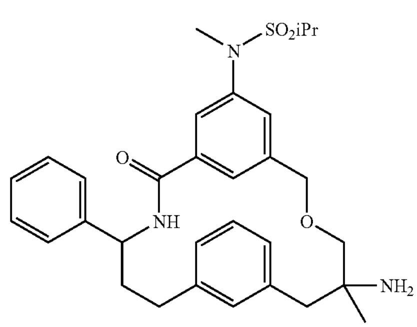 | 550 |

TABLE 1-continued
| EX | Scheme and Reference Example | Intermediates | Structure | MS M + 1 |
|---|---|---|---|---|
| 21 | Scheme 4.4 Example 1 | II.1.c.1 III.2.c.1.2 | 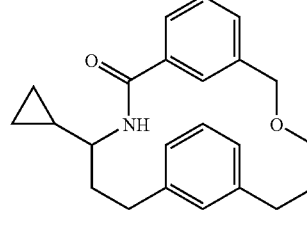 | 486 |
| 22 | Scheme 4.4 Example 1 | II.1.c.1 III.2.c.1.3 | 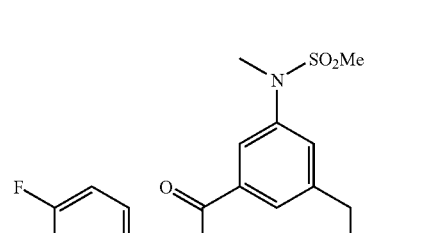 | 540 |
| 23 | Scheme 4.4 Example 5 | IV.4.e.2 acetaldehyde | 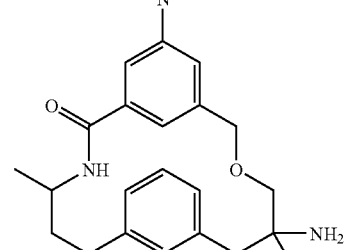 | 488 |
| 24 | Scheme 4.4 Example 5 | IV.4.e.2 isobutyraldehyde | 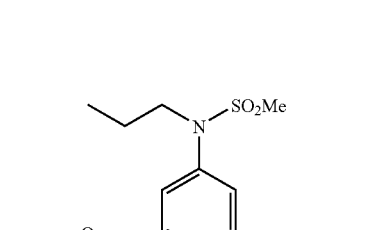 | 516 |

TABLE 1-continued

| EX | Scheme and Reference Example | Intermediates | Structure | MS M + 1 |
|---|---|---|---|---|
| 25 | Scheme 4.4 Example 5 + K₂CO₃ mediated TMS removal | IV.4.e.2 3-trimethyl-silylpropynal | 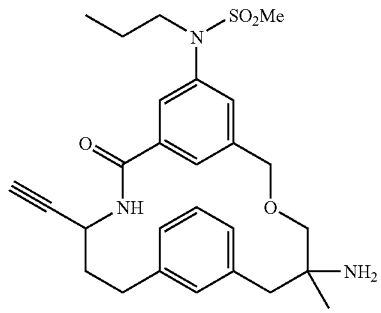 | 498 |
| 26 | Scheme 4.4 Example 1 | II.1.c.2 III.2.c.1.4 | 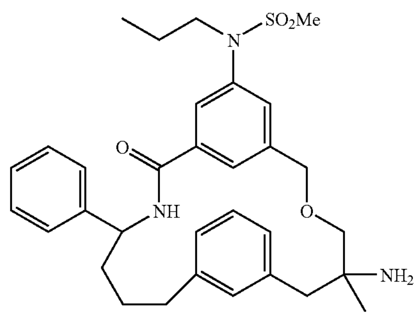 | 564 |
| 27 | Scheme 4.4 Example 1 | II.1.c.2 III.2.c.1.5 | 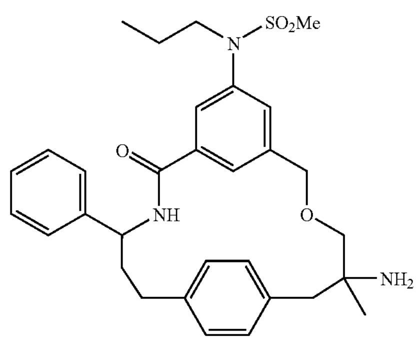 | 550 |
| 28 | Scheme 4.4 Example 1 | II.1.c.2 III.2.c.1.6 | 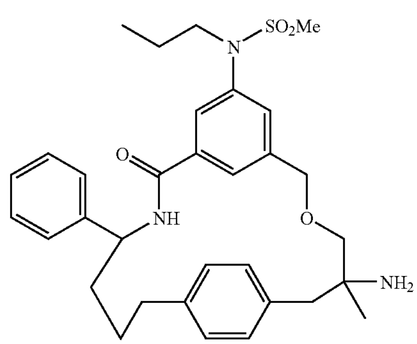 | 564 |

TABLE 1-continued
| EX | Scheme and Reference Example | Intermediates | Structure | MS M + 1 |
|---|---|---|---|---|
| 29 | Scheme 4.3 Example 4 | II.3.c III.2.b.1.1 oxazole, nBuLi, zinc chloride | 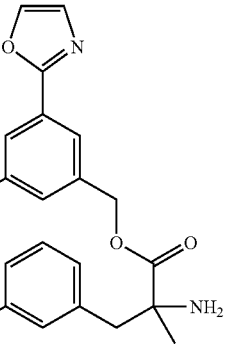 | 496 |
| 30 | Scheme 4.3 Example 4 | II.3.c III.2.b.1.1 2-bromo-3-carbomethoxyfuran, boronpinacolate | 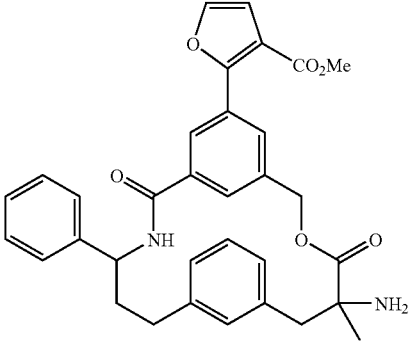 | 553 |
| 31 | Scheme 4.3 Examples 3, 4 | II.3.c III.2.b.2.1 2-CN-Ph-Zn—I | 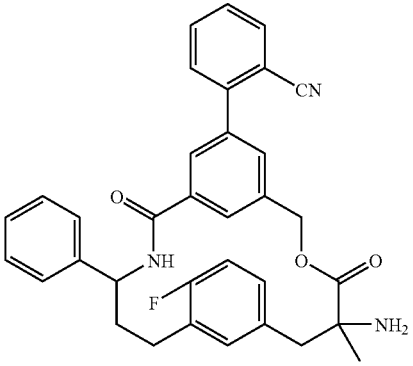 | 548 |
| 32 | Scheme 4.3 Examples 3, 4 | II.3.c III.2.b.2.3 2-CN-Ph-Zn—I | 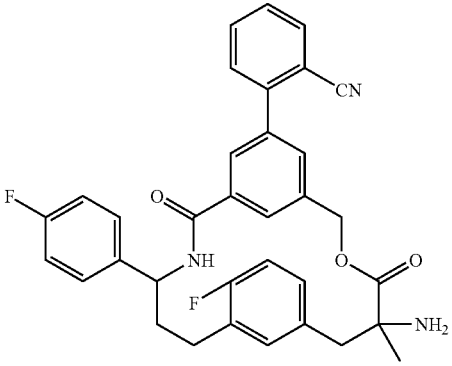 | 566 |

TABLE 1-continued

| EX | Scheme and Reference Example | Intermediates | Structure | MS M + 1 |
|---|---|---|---|---|
| 33 | Scheme 4.3 Example 3, 4 | II.3.c III.2.b.2.1 PhB(OH)$_2$ | 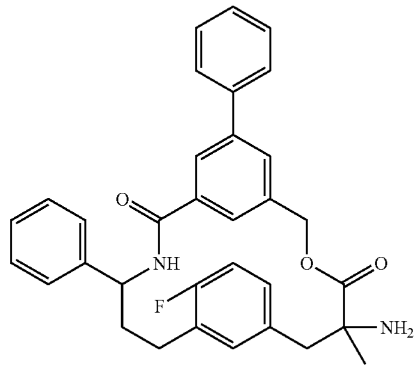 | 523 |
| 34 | Scheme 4.3 Example 3, 4 | II.3.c III.2.b.2.1 2-CN-3-F-Ph-Zn—I | 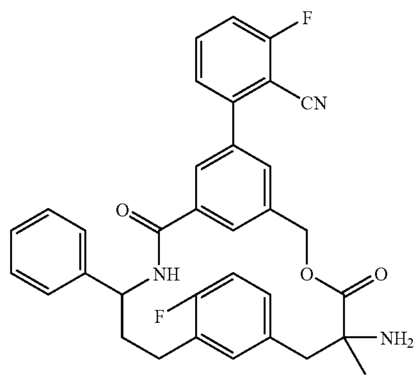 | 566 |
| 35 | Scheme 4.3 Examples 3, 4 | II.3.c III.2.b.2.3 2-CN-3-F-Ph-Zn—I | 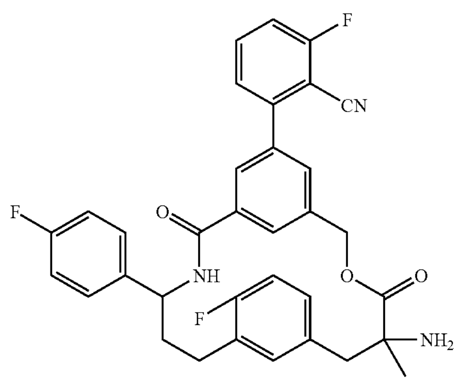 | 584 |
| 36 | Scheme 4.3 Examples 3, 4 | III.3.c III.2.b.1.3 2-CN-Ph-Zn—I | 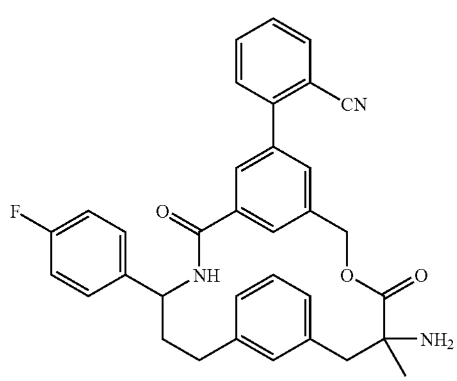 | 548 |

TABLE 1-continued

| EX | Scheme and Reference Example | Intermediates | Structure | MS M + 1 |
|---|---|---|---|---|
| 37 | Scheme 4.3 Examples 3, 4 | II.3.c III.2.b.3.1 2-CN-Ph-Zn—I | 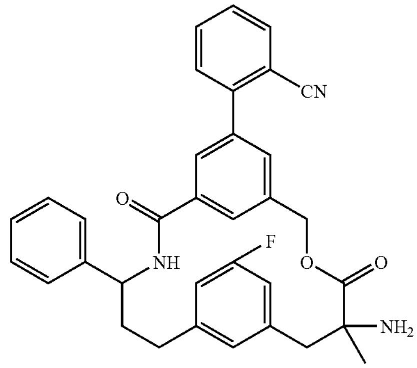 | 548 |
| 38 | Scheme 4.3 Examples 3, 4 | II.3.c III.2.b.3.3 2-CN-Ph-Zn—I | 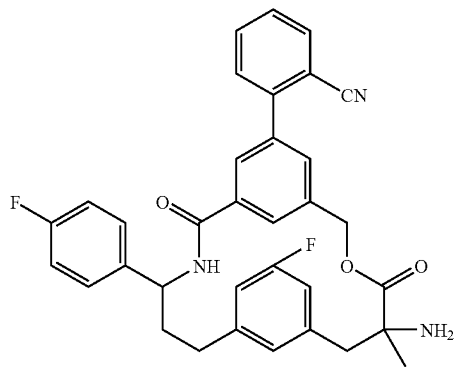 | 566 |
| 39 | Scheme 4.3 Examples 3, 4 | II.3.c III.2.b.3.1 PhB(OH)$_2$ | 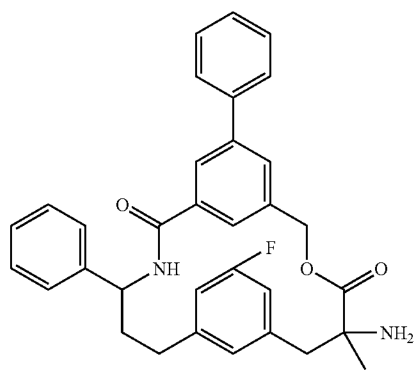 | 523 |
| 40 | Scheme 4.3 Examples 3, 4 | II.3.c III.2.b.3.1 2-CN-3-F-Ph-Zn—I | 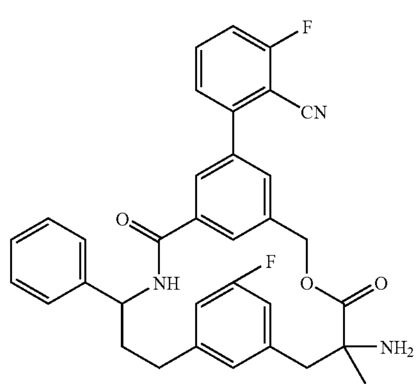 | 566 |

TABLE 1-continued
| EX | Scheme and Reference Example | Intermediates | Structure | MS M + 1 |
|---|---|---|---|---|
| 41 | Scheme 4.3 Examples 3, 4 | II.3.c III.2.b.3.3 2-CN-3-F-Ph-Zn—I | 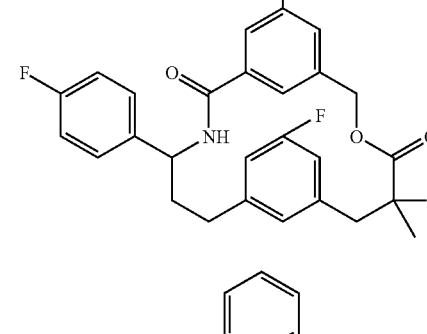 | 621 |
| 42 | Scheme 4.3 Examples 3, 4 | II.3.c III.2.b.4.1 PhB(OH)$_2$ | 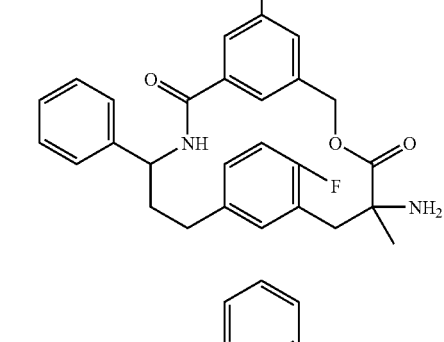 | 523 |
| 43 | Scheme 4.3 Examples 3, 4 | II.3.c III.2.b.4.1 2-CN-Ph-Zn—I | 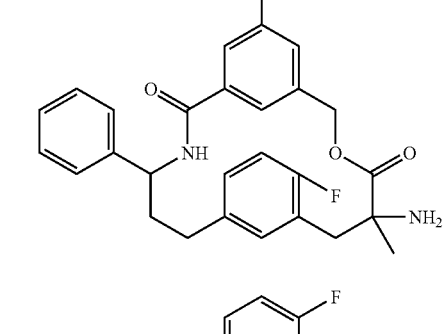 | 548 |
| 44 | Scheme 4.3 Examples 3, 4 | II.3.c III.2.b.4.1 2-CN-3-F-Ph-Zn—I | 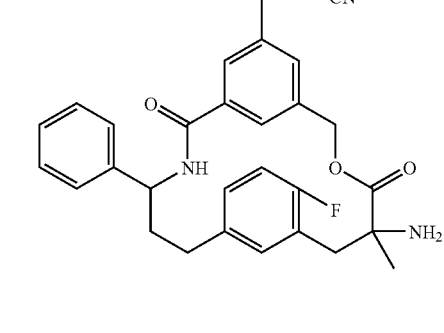 | 566 |

TABLE 1-continued

| EX | Scheme and Reference Example | Intermediates | Structure | MS M + 1 |
|---|---|---|---|---|
| 45 | Scheme 4.3 Examples 3, 4 | II.3.c III.2.b.4.3 2-CN-3-F-Ph-Zn—I | 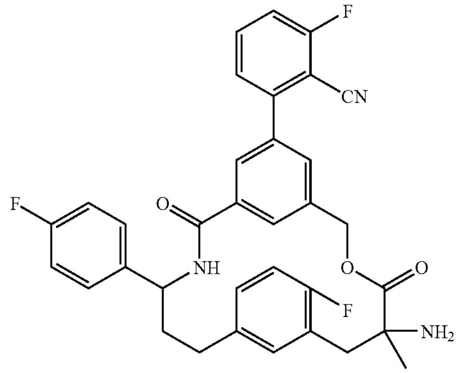 | 584 |
| 46 | Scheme 4.3 Examples 3, 4 | II.3.c III.2.b.1.3 PhB(OH)$_2$ | 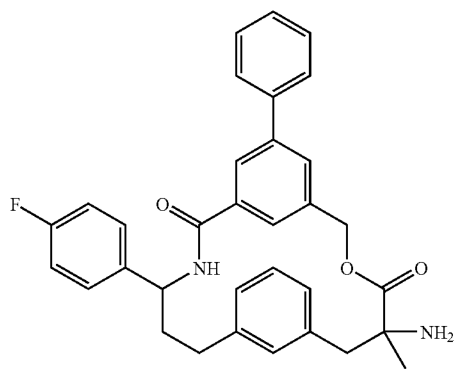 | 523 |
| 47 | Scheme 4.3 Examples 3, 4 | II.3.c III.2.b.1.3 2-CN-3-F-Ph-Zn—I | 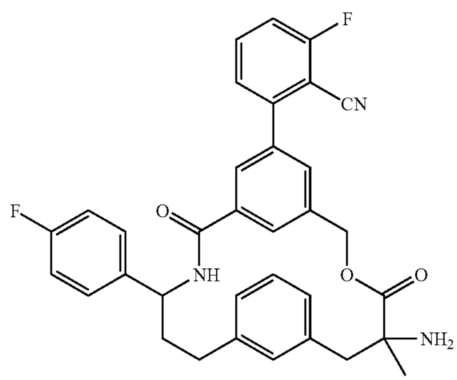 | 566 |
| 48 | Scheme 4.3 Examples 3, 4 | II.3.c III.2.b.5.3 2-CN-Ph-Zn—I | 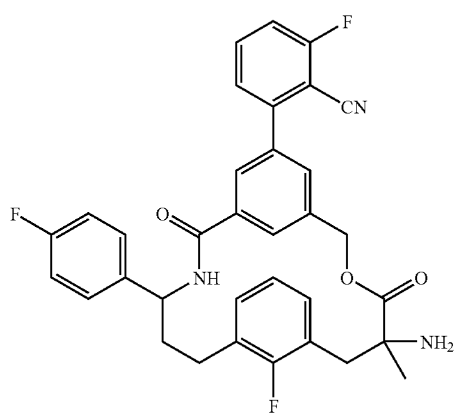 | 584 |

TABLE 1-continued

| EX | Scheme and Reference Example | Intermediates | Structure | MS M + 1 |
|---|---|---|---|---|
| 49 | Scheme 4.3 Examples 3, 4 | II.3.c III.2.b.5.3 2-CN-Ph-Zn—I | 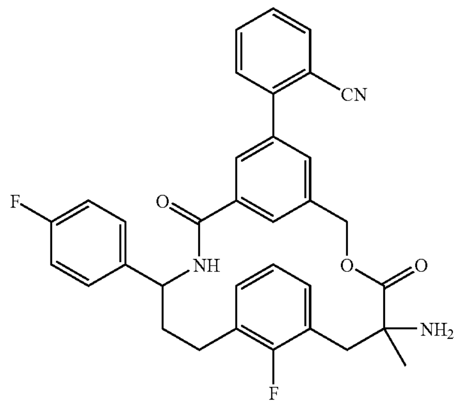 | 566 |
| 50 | Scheme 4.4 Examples 1 | II.4.c.1 III.2.c.1.1 | 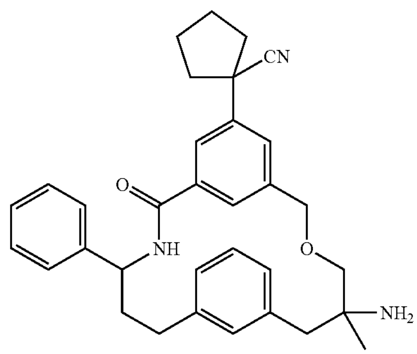 | 508 |
| 51 | Scheme 4.4 Examples 1 | II.2.g.1 III.2.c.1.3 | 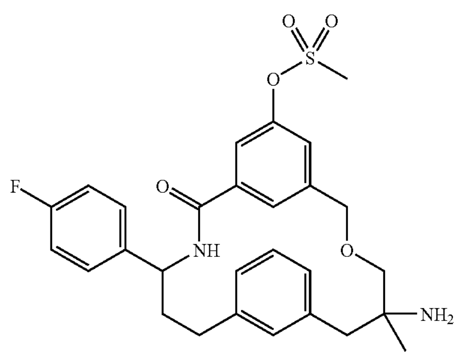 | 527 |
| 52 | Scheme 4.3 Examples 2 | II.2.g.1 III.2.b.1.3 | 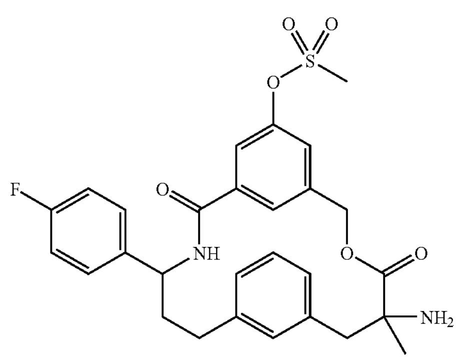 | 541 |

TABLE 1-continued

| EX | Scheme and Reference Example | Intermediates | Structure | MS M + 1 |
|---|---|---|---|---|
| 53 | Scheme 4.3 Examples 2 | II.2.g.2 III.2.b.1.3 | 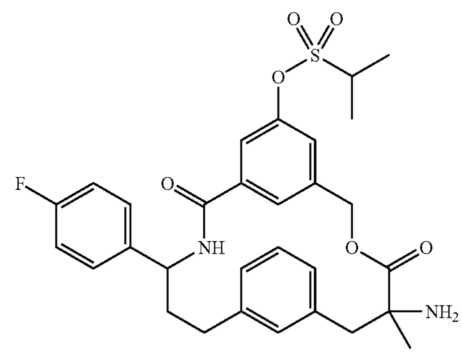 | 569 |
| 54 | Scheme 4.4 Examples 1 | II.2.g.3 III.2.c.1.3 | 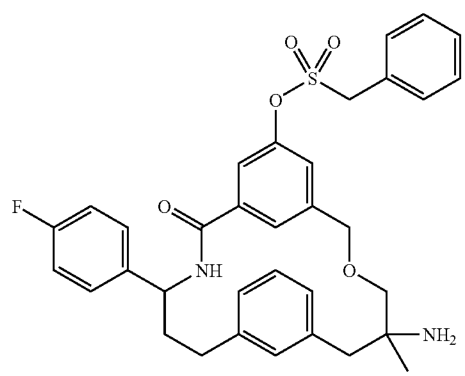 | 603 |
| 55 | Scheme 4.3 Examples 2 | II.2.g.3 III.2.b.1.3 | 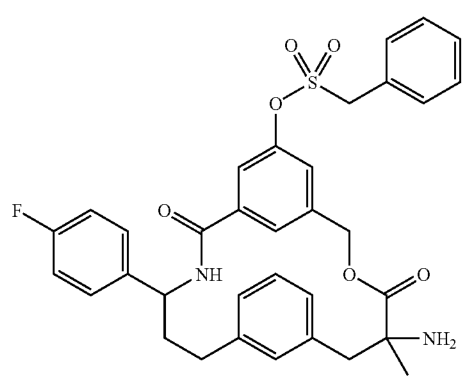 | 617 |
| 56 | Scheme 4.3 Examples 2 | II.2.g.4 III.2.b.1.3 | 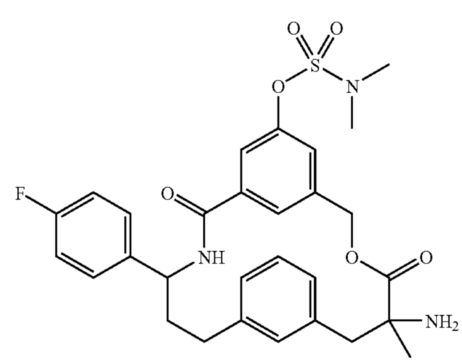 | 570 |

TABLE 1-continued

| EX | Scheme and Reference Example | Intermediates | Structure | MS M + 1 |
|---|---|---|---|---|
| 57 | Scheme 4.9 Example 11 | IV.9.b.1 EtNH$_2$ | 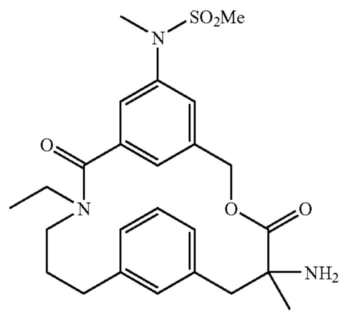 | 488 |
| 58 | Scheme 4.9 Example 11 | IV.9.b.1 PhCHMeNH$_2$ | 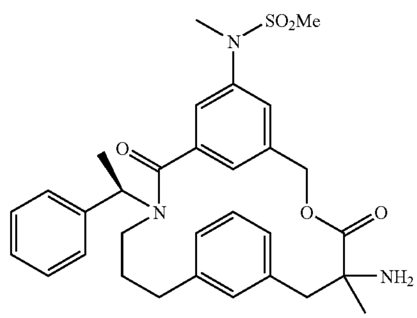 | 564 |
| 59 | Scheme 4.9 Example 11 | IV.9.b.1 3-OMe-PhCHMeNH$_2$ | 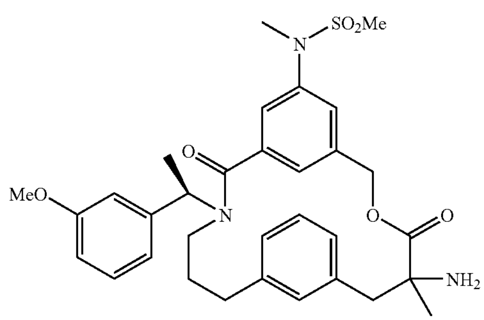 | 594 |
| 60 | Scheme 4.9 Example 11 | IV.9.b.1 4-Me-PhCHMeNH$_2$ | 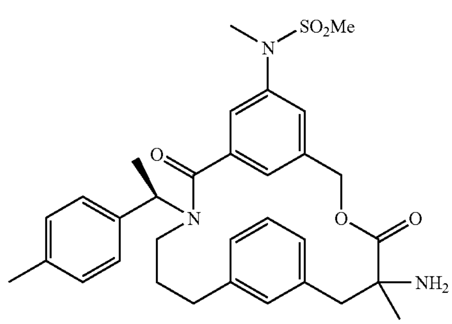 | 578 |

TABLE 1-continued

| EX | Scheme and Reference Example | Intermediates | Structure | MS M + 1 |
|---|---|---|---|---|
| 61 | Scheme 4.9 Example 11 | IV.9.b.1 4-Cl-PhCHMeNH$_2$ | 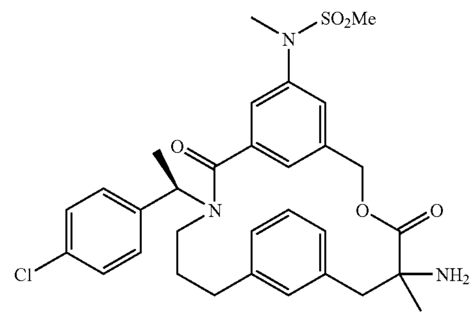 | 599 |
| 62 | Scheme 4.9 Example 11 | IV.9.b.1 4-NO$_2$-PhCHNeNH$_2$ | 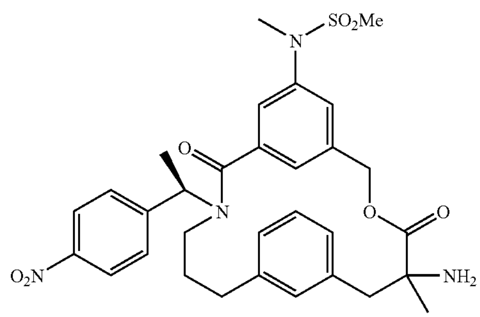 | 609 |
| 63 | Scheme 4.9 Example 11 | IV.9.b.1 4-F-PhCHMeNH$_2$ | 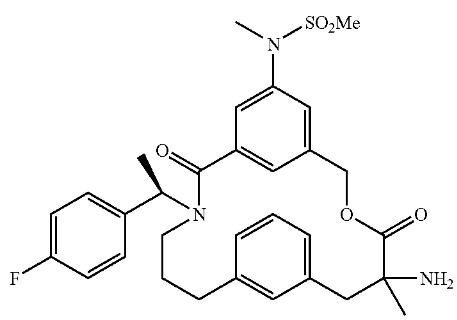 | 536 |
| 64 | Scheme 4.9 Example 11 | IV.9.b.1 PhNH$_2$ | 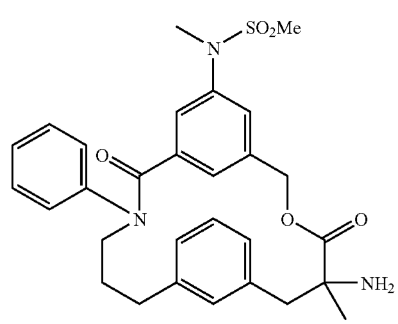 | 536 |

TABLE 1-continued

| EX | Scheme and Reference Example | Intermediates | Structure | MS M + 1 |
|---|---|---|---|---|
| 65 | Scheme 4.9 Example 11 | IV.9.b.1 PhCH$_2$CH$_2$NH$_2$ | 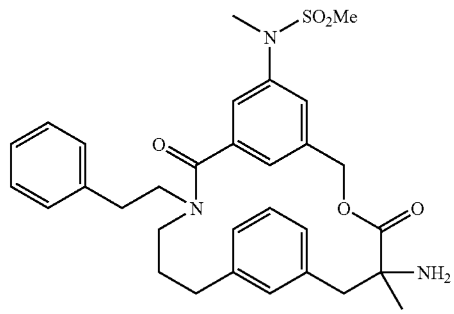 | 564 |
| 66 | Scheme 4.9 Example 11 | IV.9.b.1 cyclopropylNH$_2$ | 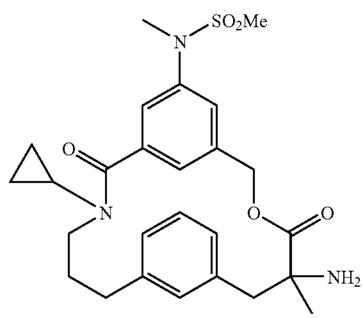 | 500 |
| 67 | Scheme 4.9 Example 11 | IV.9.b.1 nPrNH$_2$ | 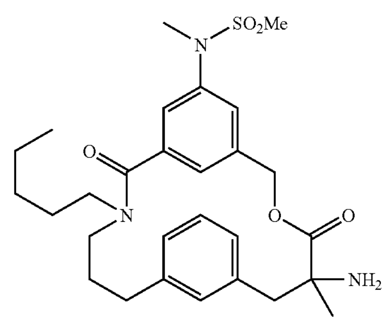 | 500 |
| 68 | Scheme 4.10 Example 11 | IV.10.b.1 CHMe$_2$(CH$_2$)$_2$NH$_2$ | 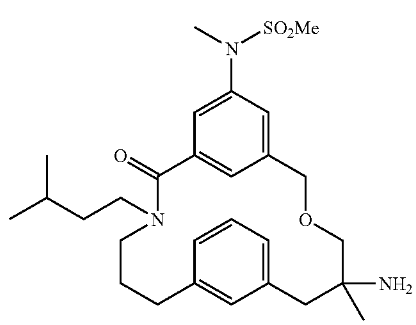 | 516 |

TABLE 1-continued

| EX | Scheme and Reference Example | Intermediates | Structure | MS M + 1 |
|---|---|---|---|---|
| 69 | Scheme 4.10 Example 11 | IV.10.b.1 PhCH$_2$NH$_2$ | 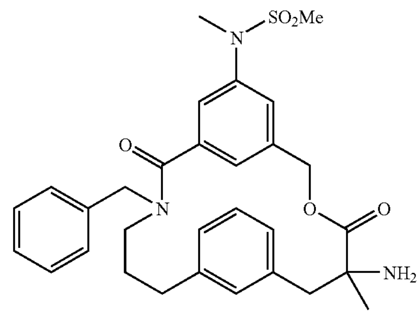 | 536 |
| 70 | Scheme 4.9 Example 11 | IV.9.b.2 PhCH$_2$NH$_2$ | 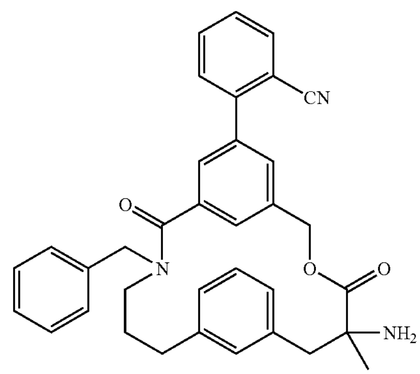 | 544 |
| 71 | Scheme 4.9 Example 11 | IV.9.b.2 nPrNH$_2$ | 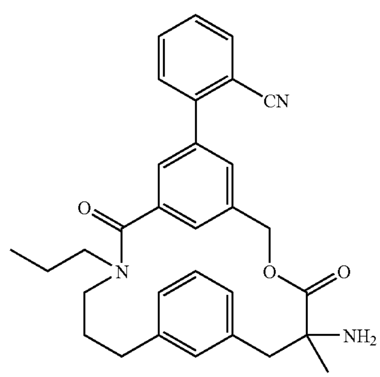 | 610 |
| 72 | Scheme 4.9 Example 11 | IV.9.b.2 MeNH$_2$ | 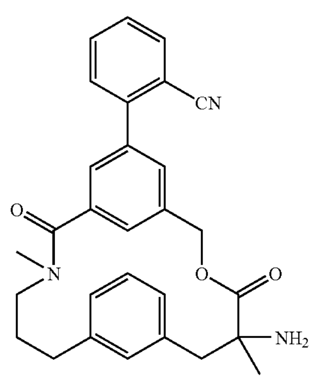 | 468 |

TABLE 1-continued
| EX | Scheme and Reference Example | Intermediates | Structure | MS M + 1 |
|---|---|---|---|---|
| 73 | Scheme 4.9 Example 11 | IV.9.b.2 Cyclopropylmethyl-amine | 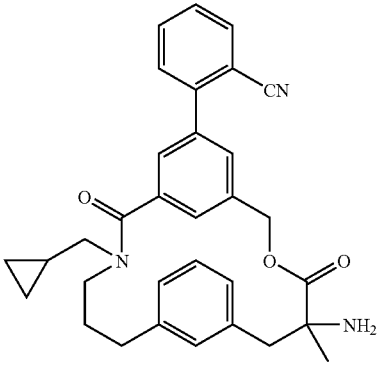 | 508 |
| 74 | Scheme 4.3 Example 2 | II.2.c.4 III.2.b.1.1 | 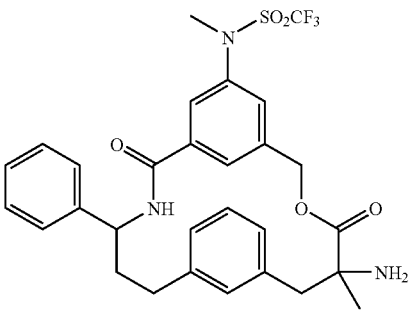 | 590 |
| 75 | Scheme 4.1 Example 1 | II.2.c.4 III.2.c.1.1 | 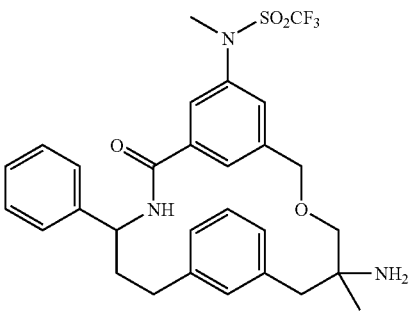 | 576 |

TABLE 1-continued
| EX | Scheme and Reference Example | Intermediates | Structure | MS M + 1 |
|---|---|---|---|---|
| 76 | Scheme 4.3 Example 2 | II.2.c.5 III.2.b.1.1 | 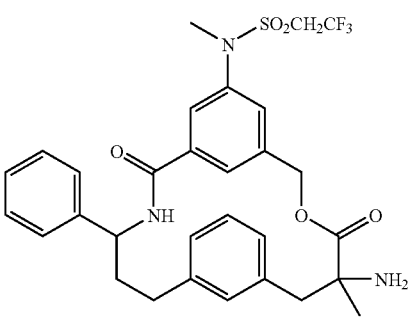 | 604 |
| 77 | Scheme 4.1 Example 1 | II.2.c.5 III.2.c.1.1 | 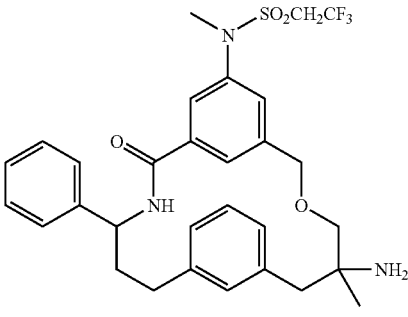 | 590 |
| 78 | Scheme 4.3 Example 2 | II.2.c.3 III.2.b.1.1 | 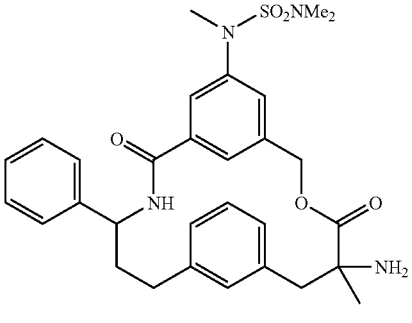 | 565 |

TABLE 1-continued

| EX | Scheme and Reference Example | Intermediates | Structure | MS M + 1 |
|---|---|---|---|---|
| 79 | Scheme 4.1 Example 1 | II.2.c.3 III.2.c.1.1 | 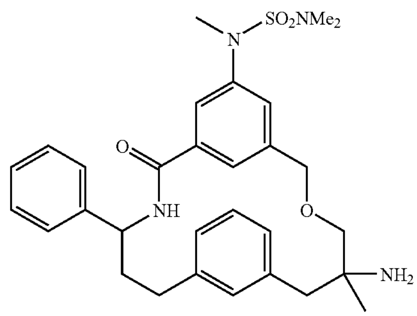 | 551 |
| 80 | Scheme 4.3 Example 2 | II.3.g.1 III.2.b.1.1 | 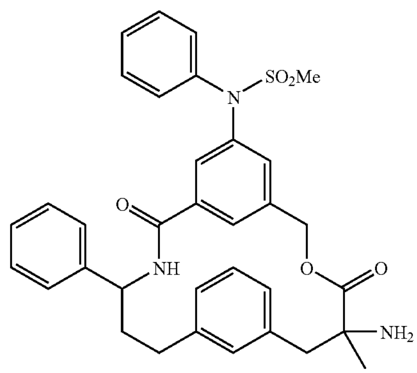 | 598 |
| 81 | Scheme 4.3 Example 2 | II.2.c.4 III.2.b.1.4 | 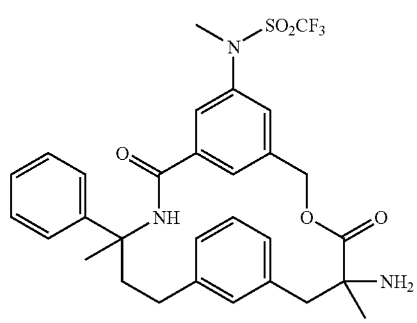 | 604 |
| 82 | Scheme 4.3 Example 2 | II.3.f.1 III.2.b.1.4 | 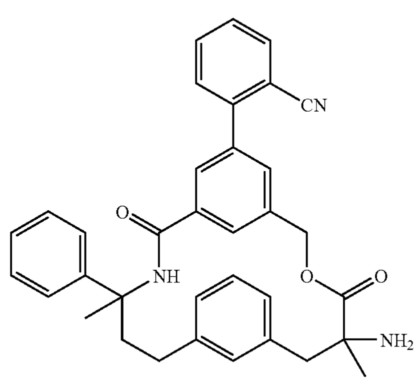 | 544 |

TABLE 1-continued

| EX | Scheme and Reference Example | Intermediates | Structure | MS M + 1 |
|---|---|---|---|---|
| 83 | Scheme 4.3 Example 2 | II.2.c.6 III.2.b.1.1 | 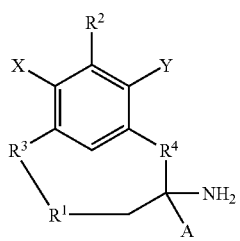 | 570 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

(I)

and pharmaceutically acceptable salts thereof, and individual enantiomers and diastereomers thereof, wherein:

X and Y are selected from the group consisting of
(1) hydrogen,
(2) —$C_{1-3}$ alkyl,
(3) halogen, and
(4) cyano;

A is selected from the group consisting of
(1) hydrogen,
(2) —$C_{1-10}$ alkyl,
(3) —$C_{2-10}$ alkenyl, and
(4) —$C_{2-10}$ alkynyl,
wherein said alkyl, alkenyl or alkynyl is unsubstituted or substituted with one or more
(a) halo,
(b) —$C_{3-8}$ cycloalkyl,
(c) —OH,
(d) —CN,
(e) —O—$C_{1-10}$ alkyl,
(f) —$C_{6-10}$ aryl, or
(g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said aryl and heteroaryl groups are unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(vii) —$C_{2-10}$ alkynyl, or
(viii) —$C_{3-8}$ cycloalkyl;

$R^1$ is phenylene, wherein said phenylene is unsubstituted or substituted with one or more
(a) halo,
(b) —$C_{1-10}$ alkyl,
(c) —$C_{2-10}$ alkenyl,
(d) —$C_{2-10}$ alkynyl,
(e) —OH,
(f) —CN,
(g) —O—$C_{1-10}$ alkyl, or
(h) —$C_{3-8}$ cycloalkyl;

$R^2$ is selected from the group consisting of:
(1) ($R^5$—$SO_2$)N($R^6$)—, wherein $R^5$ is
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
(g) —$NR^7R^8$,
wherein said alkyl, alkenyl, alkynyl, cycloalkyl, aryl and heteroaryl is unsubstituted or substituted with one or more
(i) halo,
(ii) —OH,
(iii) —CN,
(iv) —O—$C_{1-10}$ alkyl, (v) —$C_{1-10}$ alkyl,
(vi) —$C_{2-10}$ alkenyl,
(vii) —$C_{2-10}$ alkynyl,
(viii) —$C_{3-8}$ cycloalkyl,
(ix) —$C_{6-10}$ aryl, or
(x) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said aryl and heteroaryl is unsubstituted or substituted with one or more
(A) halo,
(B) —OH,
(C) —CN,
(D) —O—$C_{1-10}$ alkyl,
(E) —$C_{3-8}$ cycloalkyl,
(F) —$C_{1-10}$ alkyl,
(G) —$C_{2-10}$ alkenyl, or
(H) —$C_{2-10}$ alkynyl;

$R^6$ is selected from the group consisting of
(a) hydrogen,
(b) —$C_{1-10}$ alkyl,
(c) —$C_{2-10}$ alkenyl,
(d) —$C_{2-10}$ alkynyl,
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said alkyl, alkenyl, alkynyl, aryl or heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{6-10}$ aryl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;
wherein said cycloalkyl, aryl or heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) —$C_{6-10}$ aryl,
or $R^5$ and $R^6$ may be linked to form a group —$CH_2(CH_2)_pCH_2$—;

(2) —$C_{6-10}$ aryl, wherein said aryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{1-10}$ alkyl,
(vi) —$C_{6-10}$ aryl, or

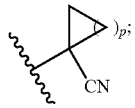

(4) heteroaryl selected from the group consisting of pyrazinyl, pyrazolyl, pyridazinyl,
pyridyl, pyrimidinyl, pyrrolyl, tetrazolyl, furanyl, imidazolyl, triazinyl, pyranyl, thiazolyl,
thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{1-10}$ alkyl,
(vii) —C(=O)—O—$C_{1-10}$ alkyl,
(viii) —C(=O)—OH, and
(ix) —C(=O)—$NR^cR^d$,
(x) —$NR^cR^d$, wherein $R^c$ and $R^d$ are selected from the group consisting of
(A) hydrogen, and
(B) —$C_{1-10}$ alkyl;
(5) hydrogen;
(6) —$CF_3$; and
(7) —O—$SO_2$—$R^9$;

$R^3$ is

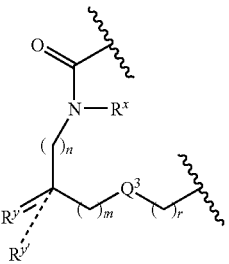

wherein $R^x$ is selected from the group consisting of
(a) hydrogen,
(b) —$C_{1-6}$ alkyl,
(c) —$C_{0-3}$ alkylene-$C_{3-8}$ cycloalkyl,
(d) —$C_{0-3}$alkylene-$C_{6-10}$ aryl
and said $R^x$ alkyl, alkylene, cycloalkyl and aryl groups are unsubstituted or substituted with one or more
(i) halo,
(ii) —$C_{1-10}$ alkyl,
(iii) —OH,
(iv) —CN, or
and if the dotted line leading to $R^y$ is absent, then $R^y$ is selected from the group consisting of
(a) hydrogen,
(b) —$C_{1-10}$ alkyl,
(c) —$C_{2-10}$ alkenyl,
(d) —$C_{2-10}$ alkynyl, (e) —$C_{3-8}$ cycloalkyl,
(f) —$C_{0-6}$ alkylene-$C_{6-10}$ aryl, or
(g) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, and said $R^y$ alkyl, alkylene, alkenyl, alkynyl, cycloalkyl and heteroaryl groups are unsubstituted with one or more
(i) halo,
(ii) —$C_{1-10}$ alkyl,
(iii) —OH,
(iv) —CN, or
(v) —O—$C_{1-10}$ alkyl, and $R^{y'}$ is selected from the group consisting of
(a) hydrogen, and
(b) —$CH_3$, and if the dotted line leading to $R^y$ represents a bond, then $R^{y'}$ is absent and $R^y$ is selected from the group consisting of
(a) =CH—$C_{1-10}$ alkyl,
(b) =CH—$C_{0-6}$ alkylene-$C_{6-10}$ aryl, or
(c) =$CH_2$ wherein said alkyl, alkylene, cycloalkyl, aryl or heteroaryl $R^y$ groups are unsubstituted or substituted with one or more
(i) halo,
(ii) —$C_{1-10}$ alkyl,
(iii) —OH,
(iv) —CN, or
(v) —O—$C_{1-10}$ alkyl, or
(vi) —$C_{3-8}$ cycloalkyl;

$Q^3$ is —$CH_2$—;
$R^4$ is —C(=O)—O—$CH_2$;
$R^7$ and $R^8$ are selected from the group consisting of
(1) —$C_{1-10}$ alkyl, and
(2) —$C_{0-3}$ alkyene-$C_{6-10}$ aryl,
wherein said alkyl, alkylene and aryl is unsubstituted or substituted with one or more
(a) halo,
(b) —$C_{1-10}$ alkyl,
(c) —OH,
(d) —CN,
(e) —O—$C_{1-10}$ alkyl, or
(f) —$C_{3-8}$ cycloalkyl;

$R^9$ is selected from the group consisting of
(1) —$C_{1-10}$ alkyl, and
(2) —$C_{0-3}$ alkylene-$C_{6-10}$ aryl,
wherein said alkyl, alkylene and aryl is unsubstituted or substituted with one or more
(a) halo,
(b) —$C_{1-10}$ alkyl,
(c) —OH,
(d) —CN,
(e) —O—$C_{1-10}$ alkyl, or
(f) —$C_{3-8}$ cycloalkyl, or $R^9$ is $NR^7R^8$;
m is 1;
n is 0;
p is 1, 2, 3, 4 or 5;
q is 2, 3, 4 or 5; and
r is 0.

2. A compound of claim 1 wherein X and Y are both hydrogen.

3. A compound of claim 1 wherein the dotted line leading to $R^y$ is absent and $R^y$ is selected from the group consisting of
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{0-6}$ alkylene-$C_{6-10}$ aryl, or
(f) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, wherein said alkyl, alkylene, alkenyl, alkynyl, cycloalkyl, aryl or heteroaryl are unsubstituted or substituted with one or more
(i) halo,
(ii) —$C_{1-10}$ alkyl,
(iii) —OH,
(iv) —CN,
(v) —O—$C_{1-10}$ alkyl, or
(vi) —$C_{3-8}$ cycloalkyl, and $R^{y'}$ is hydrogen.

4. A compound of claim 1 wherein $R^x$ is hydrogen.

5. A compound of claim 1 wherein A is selected from the group consisting of
(1) hydrogen, and
(2) —$C_{1-10}$ alkyl,
wherein said alkyl is unsubstituted or substituted with one or more
(a) halo,
(b) —$C_{3-8}$ cycloalkyl,
(c) —CN
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl.

6. A compound of claim 1 wherein $R^2$ is ($R^5$—$SO_2$)N($R^6$)—, wherein $R^5$ is —$C_{1-6}$ alkyl, wherein said alkyl is unsubstituted or substituted with one or more
(i) halo,
(ii) —OH,
(iii) —CN,
(iv) —O—$C_{1-6}$ alkyl, or
(v) —$C_{1-6}$ alkyl, and $R^6$ is selected from the group consisting of
(a) hydrogen,
(b) —$C_{1-6}$ alkyl,
(c) —$C_{6-10}$ aryl,
wherein said alkyl and aryl is unsubstituted or substituted with one or more
(i) halo,
(ii) —OH,
(iii) —CN,
(iv) —O—$C_{1-6}$ alkyl or
(v) —$C_{1-6}$ alkyl.

7. A compound of claim 1 wherein $R^2$ is phenyl, unsubstituted or substituted with cyano.

8. A compound of claim 1 which is a compound of formula (II):

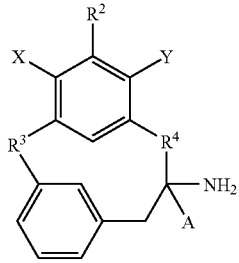

(II)

and pharmaceutically acceptable salts thereof, and individual enantiomers and diastereomers thereof.

9. A compound of claim 1 which is a compound of formula (III):

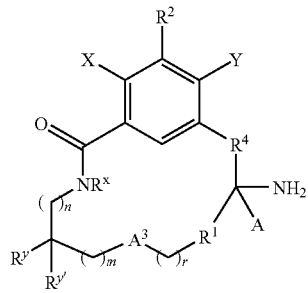

(III)

and pharmaceutically acceptable salts thereof, and individual enantiomers and diastereomers thereof.

10. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,678,783 B2 | |
| APPLICATION NO. | : 11/667913 | |
| DATED | : March 16, 2010 | |
| INVENTOR(S) | : Phillipe G. Nantermet | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 112 days.

Signed and Sealed this

Twenty-sixth Day of October, 2010

David J. Kappos
*Director of the United States Patent and Trademark Office*